United States Patent [19]
Lupski et al.

[11] Patent Number: 6,132,954
[45] Date of Patent: *Oct. 17, 2000

[54] METHODS OF SCREENING FOR AGENTS THAT DELAY A CELL CYCLE AND COMPOSITIONS COMPRISING ERA AND AN ANALOGUE OF WILD-TYPE ERA

[75] Inventors: James R. Lupski, Houston, Tex.; Robert A. Britton, Cambridge, Mass.; Donald L. Court; Bradford S. Powell, both of Frederick, Md.

[73] Assignees: Baylor College of Medicine, Houston, Tex.; The United States of America as represented by the Department of Health and Human Services, Washington, D.C.

[*] Notice: This patent issued on a continued prosecution application filed under 37 CFR 1.53(d), and is subject to the twenty year patent term provisions of 35 U.S.C. 154(a)(2).

[21] Appl. No.: 08/915,498

[22] Filed: Aug. 20, 1997

Related U.S. Application Data

[60] Provisional application No. 60/023,353, Aug. 20, 1996.

[51] Int. Cl.$^7$ .............................. C12Q 1/68; G01N 33/53
[52] U.S. Cl. .................... 435/4; 435/6; 435/7.1; 435/7.21; 435/32; 536/23.1; 536/23.2
[58] Field of Search ........................ 435/4, 32, 6, 7.21, 435/172.3, 7.1; 536/23.1, 23.2

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |

FOREIGN PATENT DOCUMENTS

| | | |
|---|---|---|
| 0 320 308 A2 | 6/1989 | European Pat. Off. . |
| 0 329 822 A2 | 8/1989 | European Pat. Off. . |
| 2 202 328 | 9/1988 | United Kingdom . |
| WO 88/10315 | 12/1988 | WIPO . |
| WO 89/06700 | 7/1989 | WIPO . |
| WO 89/09283 | 10/1989 | WIPO . |
| WO 89/09284 | 10/1989 | WIPO . |

OTHER PUBLICATIONS

Ngo et al Computational Complexity, Protein Structure Prediction, and the Levinthal Paradox. In: The Protein Folding problem and Tertiary Structure Prediction. ed. Merz et al. Birkhauser, Boston, pp. 433–440, 1994.

Lerner et al. Cold-sensitive Growth and Decreased GTP-hydrolytic Activity From Substitution of Pro 17 for Val in Era, an Essential *Escherichia coli* GTPase. FEMS Microbiology Letters vol. 95:137–142, 1992.

Gollop et al. A GTP-Binding Protein (Era) Has an Essential Role in Growth Rate and Cell Cycle Control in *Escherichia coli*. Journal of Bacteriology. vol. 173(7):2265–2270, Apr. 1991.

Versalovic, "Evolution of the macromolecular synthesis operon and analysis of bacterial primase", Ph.D. Thesis, Baylor College of Medicine, Houston, TX, 1994.

Ahnn, et al., "A GTP-binding protein of *Escherichia coli* has homology to yeast RAS proteins", *Proc. Natl. Acad. Sci. USA*, 1986, 83, 8849–8853.

Altuvia, et al., "RNase III stimulates the translation of the cII gene of the bacteriophage λ.", *Proc. Natl. Acad. Sci. USA*, 1987, 84, 6511–6515.

Bardwell et al., "Autoregulation of RNase III operon by mRNA processing", *EMBO J.*, 1989, 8(11), 3401–3407.

Bourne, H. R., et al., "The GTPase superfamily: conserved structure and molecular mechanism", *Nature*, 1991, 349, 117–127.

Bram, R. J., et al., "The ribonuclease III site flanking 23S sequences in the 30S ribosomal precursor RNA of *E. coli*", *Cell*, 1980, 19, 393–401.

Bramhill, D., et al., "GTP-dependent polymerization of *Escherchia coli* FtsZ protein to form tubules", *Proc. Natl. Acad. Sci. USA*, 1994, 91, 5813–5817.

Britton, R.A., et al., "Characterization of Mutations Affecting the *Escherichia coli* Essential GTPase Era That Suppress Two Temperature-Sensitive dnaG Alleles", *J. Bacteriol.*, 1997, 179(14), 4575–4582.

Chen, S. –M., et al., "Expression and characterization of RnaseIII and Era proteins", *J. Biol. Chem.*, 1990. 265(5), 2888–2895.

Clanton, D.J., et al., "Structural Significance of the GTP–Binding Domain of ras p21 Studied by Site–Directed Mutagenesis", *Mol. Cell. Biol.*, 1987, 7(9), 3092–3097.

Cooper, S., et al., "Chromosome replication and the division cycle of *Escherichia coli* B/r", *J. Mol. Biol.*, 1968, 31, 519–540.

Court, D., "RNA Processing and Degradation by RNase III", *Control of Messenger RNA Stability*, Academic Press, Inc., 1993, Chap. 5, 71–116.

De Boer, P., et al., "The essential bacterial cell–division protein FtsZ is a GTPase", *Nature*, 1992, 359, 254–256.

Donachie, W. D., et al., "Chromosome partition in *Escherichia coli* requires post–replication protein synthesis", *J. Bacteriol.*, 1989, 171(10), 5405–5409.

(List continued on next page.)

Primary Examiner—David Guzo
Assistant Examiner—Sean McGarry
Attorney, Agent, or Firm—Woodcock Washburn Kurtz Mackiewicz & Norris LLP

[57] ABSTRACT

The present invention provides for methods of screening for agents which delay the cell cycle and methods of delaying the cell cycle. Analogues of Era having arginine, histidine, or lysine at amino acid codon 17 are embodied by the present invention. Human and other homologs of bacterial Era amino acid and nucleic acid sequences are provided in the present invention. Vectors, host cells, protein preparations, cell cultures, and compositions comprising said analogue are also set forth in the present invention.

25 Claims, 21 Drawing Sheets

OTHER PUBLICATIONS

Downward, "Measurement of Nucleotide Exchange and Hydrolysis Activities in Immunoprecipitates", *Methods in Enzymology*, 1995, 255, 110–125.

Erickson, H. P., "FtsZ, a prokaryotic homolog of tubulin?", *Cell*, 1995, 80, 367–370.

Finkel, T., et al., "Activation of ras genes in human tumors does not affect localization, modification, or nucleotide binding of p21", *Cell*, 1984, 37, 151–158.

Funnel, et al., "Partition of P1 Plasmids in *Escherichia coli* mukB Chromosomal Partition Mutants", 1995, 177(9), 2381–2386.

Gegenheimer, P., et al., "Processing of procaryotic ribonucleic acid", Microbiological Reviews, 1981, 45(4), 502–541.

Gibbs, "Determination of Guanine Nucleotides Bound to Ras in Mammalian Cells", *Methods in Enzymology*, 1995, 255, 110–125.

Gollop, N., et al., "Localization of the membrane binding sites of Era in *Escherichia coli*", Res. Microbiol., 1991, 142, 301–307.

Grompe, M., et al., "Mutations in the dnaG Gene of *Escherichia coli* suggest coupling between DNA replication and chromosome partitioning", *J. Bacteriol.*, 1991, 173(3), 1268–1278.

Hiraga, S., et al., "Chromosome partitioning in *Escherichia coli*: novel mutants producing anucleate cells", *J. Bacteriol.*, 1989, 171(3), 1496–1505.

Hiraga, S., et al., "Positioning of replicated chromosomes in *Escherichia coli*", *J. Bacteriol.*, 1990, 172(1), 31–39.

Inada, T., et al., "Conditionally Lethal Amber Mutations in the Leader Peptidase Gene of *Escherichia coli*", *J. Bacteriol.*, 1989, 171(1), 585–587.

Inada, T., et al., "Temperature–Sensitive Lethal Mutant of Era, a G Protein in *Escherichia coli*", *J. Bacteriol.*, 1989, 171(9), 5017–5024.

Innis, et al., *PCR Protocols*, Academic Press, Inc., San Diego CA, 1990.

Kameyama, L., et al., "RnaseIII activation of bacteriophage λ N synthesis", *Mole. Microbiol.*, 1991, 5(12), 2953–2963.

King, T. C., et al., "Nucleolytic processing of ribonucleic acid transcripts in procaryotes", *Microbiol. Rev.*, 1986, 50(4), 428–451.

Kok, J., et al., "Effects on *Bacillus subtilus* of a conditional lethal mutation in the essential GTP–binding protein Obg", *J. Bacteriol.*, 1994, 176(23), 7155–7160.

Kolonder, R., et al., "Genetic recombination of plasmid DNA: effect of RecF pathway mutations on plasmid recombination in *Escherichia coli*", *J. Bacteriol.*, 1985, 163(3), 1060–1066.

Kornberg, A. and T. A. Baker, *DNA Replication*, Second Edition, 1992, New York, W. H. Freeman and Company.

Krengel, U., et al., "Three–dimensional Structures of H–ras p21 mutants: molcular basis for their inability to function as signal switch molecules", *Cell*, 1990, 62, 539–548.

Kwoh, D., et al., "Transcription–based amplification system and detection of amplified human immunodeficiency virus type 1 with a bead–based sandwich hybridization format", *Proc. Natl. Acad. Sci. U.S.A.*, 1989, 86, 1173–1177.

Lenzen et al., "Analysis of Intrinisic and CDC25–Stimulated Guanine Nucleotide Exchanges of $p21^{ras}$–Nucleotide Complexes by Fluorescence Measurements", *Methods in Enzymology*, 1995, 255, 95–107.

Lerner, C. G., et al., "Pleiotropic changes resulting from depletion of Era, an essential GTP–binding protein in *Escherichia coli*", Mol. Microbiol., 1991, 5(4), 951–957.

Lin, Y. P., et al., "GTPase–dependent signaling in bacteria: characterization of a membrane–binding site for era in *Escherichia coli*", *J. Bacteriol.*, 1994, 176(1), 44–49.

March, P.E., et al., "The *Escherichia coli* Ras–like protein (Era) has GTPase activity and is essential for cell growth", *Oncogene*, 1988, 2, 539–544.

Marshall, C., "Human Oncogenes", In *RNA Tumor Viruses*, R. Weiss, N. Teich, H. Varmus, and J. Coffin (eds.), Cold Spring Harbor NY, Cold Spring Harbor Laboratory, 1985, 487–558.

Moore, J.M., et al., "Kinetic Mechanism of Adenine nucleotide Binding to and Hydrolysis by the *Escherichia coli* Rep Monmer. 1. Use of Fluorescent Nucleotide Analogs", *Biochem.*, 1994, 33, 14550–14564.

Morrison, P.T., et al., "Molecular Analysis of the *Escherichia coli* recO gene", J. Bacteriol., 1989, 171(7), 3641–3649.

Mukherjee, A., et al., "Guanine nucleotide–dependent assembly of FtsZ into filaments", *J. Bacteriol.*, 1994, 176(9), 2754–2758.

Murakami, Y., et al., "Novel dnaG Mutation in a dnaP mutant of *Escherichia coli*", J. Bact., 1985, 162(2), 830–832.

Niki, et al., "The new gene mukB codes for a 177 kd protein with coiled–coil domains involved in chromosome partitioning of *E. coli*", EMBO J., 1991, 10(1), 183–193.

Ohara, O., et al., "One–sided polymerase chain reaction: The amplification of cDNA", *Proc. Natl. Acad. Sci. U.S.A.*, 1989, 86, 5673–5677.

Patterson, T.A., et al., "Improved Bacterial Hosts for Regulated Expression of genes from λ $p_L$ Plasmid Vectors", *Gene*, 1993, 132, 83–87.

Pillutla, R.C., et al., "Cross–species complementation of the indispensable *Escherichia coli* era gene highlights amino acid regions essential for activity", *J. Bacteriol.*, 1995, 177(8), 2194–2196.

Powell, B.S., et al., "Rapid confirmation of single copy lambda prophage integration by PCR", *Nucl. Acids Res.*, 1994, 22(25), 5765–5766.

Powell, B.S., et al., "Novel Proteins of the Phosphotransferase System Encoded within the rpoN Operon of *Escherichia coli*", *J. Biol. Chem.*, 1995, 270(9), 4822–4839.

Powers, S., et al., "Genes in *S. Cerevisiae* Encoding Proteins with Domains Homologous to the Mammalian ras Proteins", *Cell*, 1984, 36, 607–612.

RayChaudhuri, D., et al., "*Escherichia coli* cell–division gene encodes a novel GTP–binding protein", *Nature*, 1992, 359, 251–254.

Sambrook, et al., *Molecular Cloning: A Laboratory Manual*, 2nd ed., Cold Spring Harbor Laboratory Press, Cold Spring Harbor, NY (1989).

Sanger, F., et al., "DNA sequencing with chain–terminating inhibitors", *Proc. Nat'l. Acad. Sci. U.S.A.*, 1977, 74(12), 5463–5467.

Seeburg, P. H., et al., "Biological properties of human c–Ha–ras1 genes mutated at codon 12", *Nature*, 1984, 312, 71–75.

Sood, P., et al., "Characterization of the autophosphorylation of Era, an essential GTPase in *Escherichia coli*", Mol. Microbiol., 1994, 12(2), 201–208.

Takiff, H., et al., "Genetic analysis of the rnc operon of *Escherichia coli*", *J. Bacteriol.*, 1989, 171(5), 2581–2590.

Takiff, H., et al., "Locating essential *Escherichia coli* genes by using mini–Tn10 transposons: the pdxJ operon", *J. Bacteriol.*, 1992, 174(5), 1544–1553.

van Helvoort, J. M. L. M., et al., "Nucleoid partitioning in *Escherichia coli* during steady–state growth and upon recovery from chloramphenicol treatment", *Mol. Microbiol.*, 1994, 13(4), 577–583.

Vidwans, S. J., et al., "Possible role for the essential GTP–binding protein Obg in regulating the initiation of sporulation in *Bacillus subtilus*", *J. Bacteriol.*, 1995, 177(11), 3308–3311.

Walker, G. T., et al., "Isothermal in vitro amplification of DNA by a restriction enzyme/DNA polymerase system", *Proc. Natl. Acad, Sci. U.S.A.*, 1992, 89, 392–396.

Weinstock, G., "General recombination in *Escherichia coli*.", F. C. Neidhardt (ed.), in *Escherichia coli* and *Salmonella typhimurium.* Cellular and Molecular Biology, Washington, D. C., American Society for Microbiology, 1987, 1034–1043.

Welsh, K.M., et al., "Biochemical Characterization of the Essential GTP–binding protein Obg of *Bacillus subtilis*", *J. Bacteriol.*, 1994, 176(23), 7161–7168.

Wu, D. Y., et al., "The Litigation Amplification Reaction (LAR) –Amplification of Specific DNA Sequences Using Sequential Rounds of Template–Dependent Ligation", *Genomics*, 1989, 4, 560–569.

Wu, J., et al., "Expression, purification, and characterization of a novel G protein, SGP, from Streptococcus mutans", *Infect. Immun.*, 1995, 63(7), 2516–2521.

Yamashita, Y., et al., "Molecular characterization of a Streptococcus mutans mutant altered in environmental stress responses", *J. Bacteriol.*, 1993, 175(19), 6220–6228.

Zuber, M., et al., "Analysis of the rnc locus of *Coxiella burnetii*", Mol. Microbiol., 1994, 14(2), 291–300.

Zuber, M., et al., "A *Francisella tularensis* DNA clone complements *Escherichia coli* defective for the production of Era, an essential Ras–like GTP–binding protein", *Gene,* 1997, 189, 31–34.

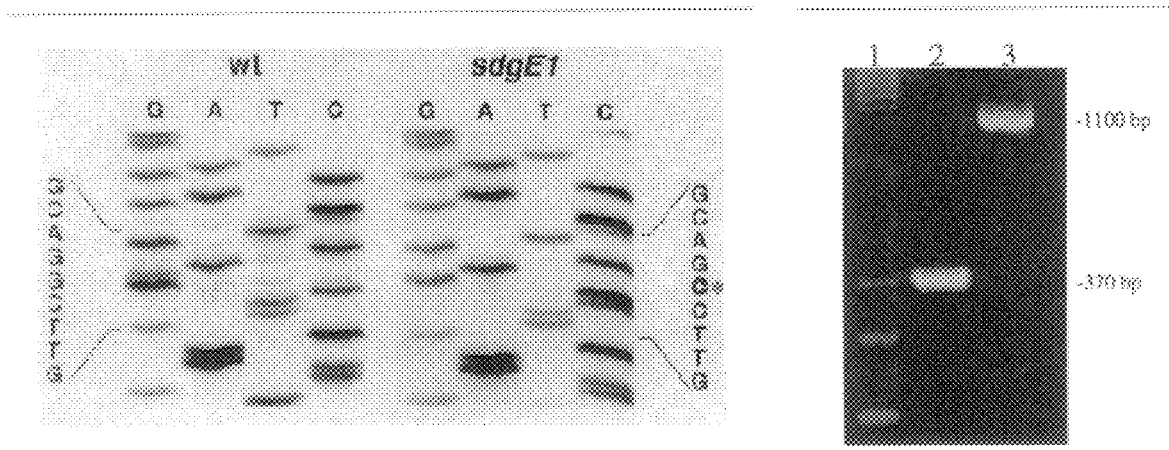
FIG. 2A
FIG. 2B
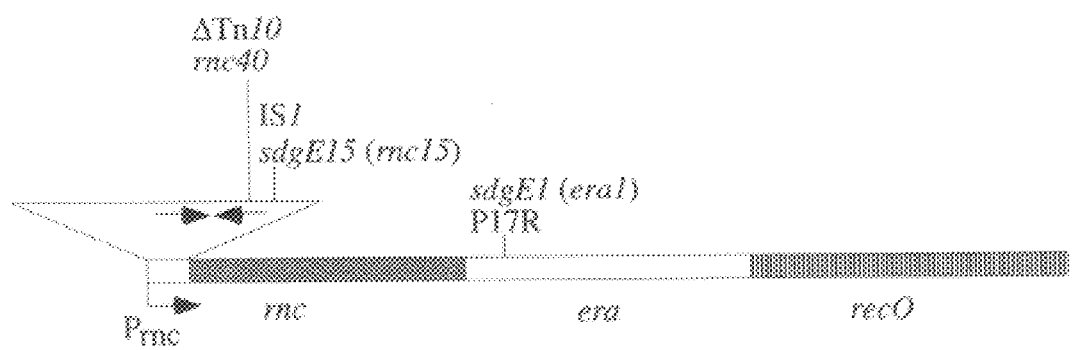
FIG. 2C

| Strain | Doubling Time | | |
|---|---|---|---|
| | 42°C | 37°C | 25°C |
| RABA17 | 29 min. | 28 min. | 85 min. |
| BSP750 | 65 min. | 75 min. | 235 min. |

FIGURE 4

```
                       R in eral
                       |
Era  10 F I A I V G R P N V G K S T L L 24
Ras   5 K I V V V G G G V G K S A L T 20
                     |
                     Mutated in Human Ras
```

FIGURE 6

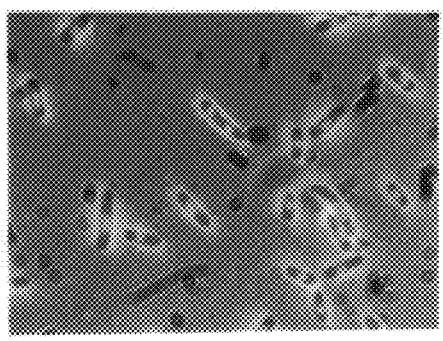
FIG. 12A
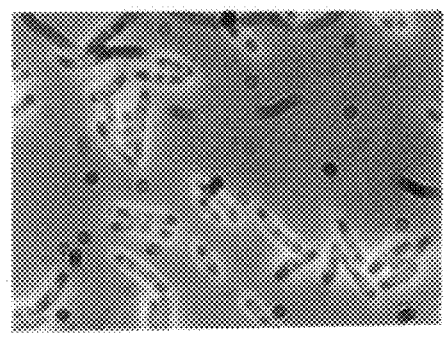
FIG. 12B
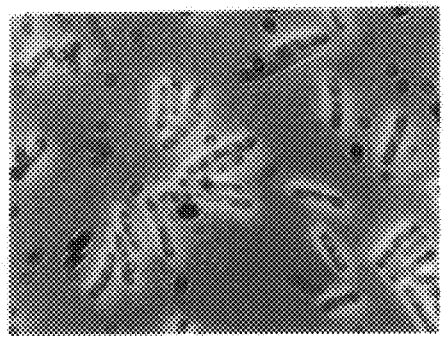
FIG. 12C
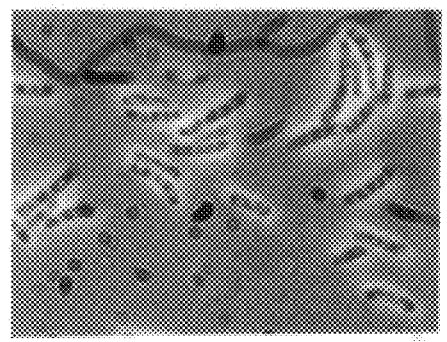
FIG. 12D
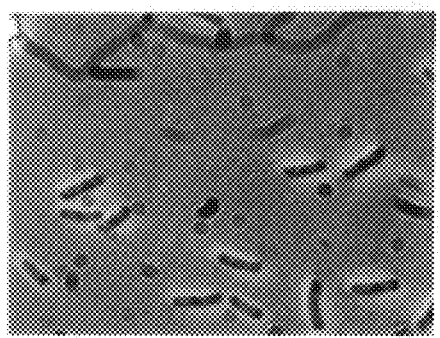
FIG. 12F
FIG. 12E

```
      1                                                                    70
Ftul  ..........  ......mkk.  .c-yis-i--  ----------  nilky-vs--  -r-p----hq  -.tgik-l-d
Cbur  ..........  ......mkpt  yc-ya--i--  ----------  q-le----s--  -r-p----yq  -l.gvk-fkd
Bsub  ..........  ....mtnesf  ks---s-i--  -------f--  rvi----a-m  -d-p----nk  v.qgvl-t-t
Ecol  ..........  ....msidks  yc-i--v--   ----------  k-l----s--  -r-a----hr  -v.qih-e-a
Hinf  ..........  ..mteqfdkt  yc-i--v--   ----------  kil----s--  -r-a----hr  -vgi.k-e-a
Mlep  ..........  ....vdmaef  rs---cli--  --t------t-  a-v-t-va--  -m-p----ht  -rgivhre-n
Smut  ..........  ........msf  ks-----l--  -------f--  hvm----a-m  -d-a----nk  -mgiyt-dke
Syne  mdipnttati  atipqapagf  rs-----v--  --------m-  q-v----a--  -pva----nr  lqgiit-pss
Mgen  ..........  ......mkvl  k...-gvl-p  t-a------i-  f-hnddslmv  -smnn--lls  -stevinqan
Cons  ----------  ----------  --GFVAI-GR  PNVGKSTLLN  -L-GQKI-IT  S-K-QTTR--  I-----T-G-
                                         G-1                     Box A 71                                                                   140
Ftul  t-f-y-----  i-ikepkain  kf---a-ttm  fkd--v-l--  -.....emgk  wtelednive  ..k-khse..
Cbur  i-v-y-----  l-agtertin  ry--rt-rga  lrd--a-v--  i..e.ph...  wesq-awvld  ..n-keie..
Bsub  s-t-fi----  i-kpkhk.lg  df-m-v-qnt  lke----l-m  inae..e..g  ygkg-efiie  ..k-qtms..
Ecol  y-a-y-----  l-meekrain  rl---a-sss  igd-e-vi--  -..e..gtr.  wtpd-emvln  ..k-r..egk
Hinf  y-e-y-----  l-ieekrain  rl--ra-ssa  igd----i--  -...d..gth.  wnad-emvln  ..k-rn..ak
Mlep  f-ivl-----  l-.rprtllg  krl-dlvrdt  yte----glc  ipad..eat.  .gpg-rwivn  ..qirsvapk
Smut  .-jvfi----  i-.kpktalg  df-ves-yst  lre--tvl-m  -pad..e..k  rgkg-nmiie  ..r-k..aak
Syne  .-i-ll----  l-.kphhelg  rvlv-n-lqa  ihs---vv-l  -...dssatl.  .grg-rfvvd  l...qktdg.
Mgen  knivfi-v--  ftekkhsnye  .lit-eirka  lsqi-vllll-  -...rsdqn..  .nkieflktq  lqq-kryqnl
Cons  -Q-I-VDTPG  -H--------  --MNK-A---  ---VDLI-FV  V---------  ----D-----  ---L------
           G-3

141                                                                  210
Ftul  i-if-vv--v  --.kksleaa  mf-eyikekl  .s-ydv....  ....iyv--k  ....q-h-in  e-esriekl-
Cbur  t--f-vi--v  --iknrae--  pl-ek.vssl  ya-qki....  ..t--.l--k  t.....dq-g  t-eqavhqlm
Bsub  t--f-iv--i  --i.hpdg--  ll-dey.rkr  yp-k-i....  ..--..i--.  ...le-n-ie  t-laqieay-
Ecol  a---i-av--v  --nvqekad--  phlqflasqm  .n-ldi....  ..--..i--.  ....t-l--d  tiaaivrkh-
Hinf  a--v-ai--v  --niknkdd--  pf-tdlsskf  .n-ah.....  ..i--..i--q  r.....n--h  e-ekivrqs-
Mlep  tilvvivt-i  --vp.kdr-s  aqlvavsdlv  adsa-.....  .i--..v--.  ...vt-eq-d  v-idvlaaa-
Smut  v--i-vi--i  --vh.pdq--  eq-ddfrnqm  .d-q-.....  .i--..i--.  ...lq-n--s  h-vdllvdh-
Syne  .--vvgl--q  -......qqpp  dqreelnasy  etlt-nhgwp  cf.k..f--.  ...lt-egls  nfqsalear-
Mgen  trif-inkfh  q-slsevnka  iileefkpq.  kti.-in...  .......l...  .lkfdknlfw  sifkqvelry
Cons  -PV-L--NK-  DK------LL  --I-------  --F-E-----  --VP---SA-  -----G-NV-  -L-------L
             G-4

211                                                                  280
Ftul  --seyffyee  dqi--rsik-  mva-i----i  mrtigs-v-y  qi-..ve-ds  ykvdqekni.  .vy-y-s-l-
Cbur  --sp.fyf-p  eqv--rsdq-  ma--i----l  mrllgq-i-y  -l-..vtlie  fr..ke-ki.  .ir-s-v-w-
Bsub  ---pqfy.-s  dqv--hpe--  ii--l----v  lhltre-i--  -i-..a-.e.  .sikgqdngs  .vhva-t-v-
Ecol  --athhf.-e  dyi--rsq--  ma--i----l  mrflga-l-y  -vt.-e.-e.  .rfvan-rgg  y.d-ngl-l-
Hinf  r--vhhf.-e  dyv--rsq--  ma--i----l  mrftge-l-y  -vt.-e.-e.  .qfkvn-rgt  y.e-ngl-l-
Mlep  -p-payysag  e.l-epeel  lma-l---av  legvhd-l--  -l-v-.idev  sp..ragrgd  lidvh-vly-
Smut  e---fqyfpad  q.i--hpe--  lv--m----v  llltre-i--  -v-v-.id..  sm.ard-eth  kih-r-t-m-
Syne  dp-pyyyp-d  .lv--qpe--  ima-l---qi  llltrq-v--  -v-ia...ie  kv...e-tpe  rtnvf-a-t-
Mgen  n...lfrkdi  nfidannnd-  kil-gl--qi  ifyckn-i--  .i-.rie-ie  ksfnkeknll  kihl..v-s-
Cons  PEG-----P-  ---TD---RF  --SE-IREK-  ------E-PH  S-A-V--I--  ------E---  ---I-A-I-V
                                                     Box B 281                                                                  347
Ftul  --n-------  -a--ak--k-  -tds-i----r  -...v-mq-n-  kth----sg-  s-ddra-ks-  --dli..
Cbur  -kk-------  --g-er--rv  -tn--l-m-k  w..f-kr-f-  q------sg-  a-nerl-re-  -fee...
Bsub  --d-------  ----sl--ev  -kr-a----a  -...l-sr-y-  e------qkd-  rnkmsq-rdf  -fkedey
Ecol  --eg--km--  -n--aki-t-  -ie--k-mqe  m..feap-h-  e------sg-  a-dera-rs-  --vddl.
Hinf  --eg--km--  -ag-qki-t-  -me--a-m-r  -...fdnk-h-  e------sg-  a-dera-rs-  --mde..
Mlep  --p-------  --s-ar-rev  -ia--rq--k  -...l-tniy-  d-h-n-akn-  qrnpkq-gr-  -f.....
Smut  --d-----i-  ----am--k-  -qm--r----l  m..l-dk-y-  et-----kn-  r-kkld-adf  --nkkey
Syne  --g-----i-  -q--sm-qa-  -ta--qq-qk  -...isgd-y-  k-f---epk-  rqsrqq-lef  --rvee.
Mgen  pkl---k-i-  --naemi-a-  -iat-kkl..  -nhfdcdifi  dif--te...  ....kqk-pvy  sflsk..
Cons  ER-SQKGIVI  GKKG--LK-I  G--AR-DIE-  L---G--V-L  -LWYKYK--W  -D----L--L  GY-----
         Box C                                         Box D
```

FIG. 18

Figure 19A
Sequence of the human *ERA* gene

```
  1  GAGGTGGCTG CCCCCAGCTG GCGCGGGGCT AGGCTTGTTC AATCGGCGT
 50  TAAGAGTCTG GCAGGTGGGC CCTCATGTCG CGAGGGAGCG GGTGATCCCT
100  TTTTCCTCAC TCTTAGGCTT CCAACGGAGG TGCGTGTCCT GCGTCGCGGG
150  GTCCGCTTTC TCTGGTCCCC GCTTGGCCTC GGCTTCTCGC AGTAATGGCC
200  AGGGCTCTGC CCTGGACCAC TTCCTCGGAT TCTCTCAGCC CGACAGTTCG
250  GTGACTCCTT GCGTCCCCGC GGTGTCCATG AACAGAGATG AGCAGGATGT
300  CCTCTTGGTC CATCACCCTG ATATGCCTGA GAATTCCCGG GTCCTACGAG
350  TGGTCCTCCT GGGAGCCCCG AATGCAGGGA AGTCAACACT CTCCAACCAG
400  CTACTGGGCC GAAAGGTGTT CCCTGTTTCC AGGAAGGTGC ATACTACTCG
450  CTGCCAAGCT CTGGGGGTCA TCACAGAGAA GGAGACCCAG GTGATTCTAC
500  TTGACACACC TGGCATTATC AGTCCTGGTA AACAGAAGAG GCATCACCTG
550  GAGCTCTCTT TGTTGGAAGA TCCATGGAAG AGCATGGAAT CTGCTGATCT
600  TGTTGTGGTT CTTGTGGATG TCTCAGACAA GTGGACACGG AACCAGCTCA
650  GCCCCCAGTT GCTCAGGTGC TTGACCAAGT ACTCCCAGAT CCCTAGTGTC
700  CTGGTCATGA ACAAGGTAGA TTGTTTGAAG CAGAAGTCAG TTCTCCTGGA
750  GCTCACGGCA GCCCTCACTG AAGGTGTGGT CAATGGCAAA AAGCTCAAGA
800  TGAGGCAGGC CTTCCACTCA CACCCTGGCA CCCATTGCCC CAGCCCAGCA
850  GTTAAGGACC CAAACACACA ATCTGTGGGA AATCCTCAGA GGATTGGCTG
900  GCCCCACTTC AAGGAGATCT TCATGTTGTC AGCCCTAAGC CAGGAGGATG
```

FIGURE 19B
Sequence of the human ERA gene

```
 950   TGAAAACACT AAAGCAATAC CTTCTGACAC AGGCCCAGCC AGGGCCCTGG

1000   GAGTACCACA GTGCAGTCCT CACTAGCCAG ACACCAGAAG AGATCTGTGC

1050   CAACATTATC CGAGAGAAGC TCCTAGAACA CCTGCCCCAG GAGGTGCCTT

1100   ACAATGTACA GCAGAAGACA GCAGTGTGGG AGGAAGGACC AGGTGGGGAG

1150   CTGGTTATCC AACAGAAGCT TCTGGTGCCC AAAGAATCTT ATGTGAAACT

1200   CCTGATTGGT CCGAAGGGCC ACGTGATCTC CCAGATAGCA CAGGAGGCAG

1250   GCCATGACCT CATGGACATC TTCCTCTGCG ATGTTGACAT CCGCCTCTCT

1300   GTGAAGCTCC TCAAGTGA
```

Figure 20
Human ERA protein sequence
* = In frame stop codon

```
  1   EVAAPSWRGA  RLVQSALRVW  QVGPHVARER  VIPFSSLLGF  QRRCVSCVAG

51   SAFSGPRLAS  ASRSNGQGSA  LDHFLGFSQP  DSSVTPCVPA  VSMNRDEQDV

101   LLVHHPDMPE  NSRVLRVVLL  GAPNAGKSTL  SNQLLGRKVF  PVSRKVHTTR

151   CQALGVITEK  ETQVILLDTP  GIISPGKQKR  HHLELSLLED  PWKSMESADL

201   VVVLVDVSDK  WTRNQLSPQL  LRCLTKYSQI  PSVLVMNKVD  CLKQKSVLLE

251   LTAALTEGVV  NGKKLKMRQA  FHSHPGTHCP  SPAVKDPNTQ  SVGNPQRIGW

301   PHFKEIFMLS  ALSQEDVKTL  KQYLLTQAQP  GPWEYHSAVL  TSQTPEEICA

351   NIIREKLLEH  LPQEVPYNVQ  QKTAVWEEGP  GGELVIQQKL  LVPKESYVKL

401   LIGPKGHVIS  QIAQEAGHDL  MDIFLCDVDI  RLSVKLLK*
```

METHODS OF SCREENING FOR AGENTS THAT DELAY A CELL CYCLE AND COMPOSITIONS COMPRISING ERA AND AN ANALOGUE OF WILD-TYPE ERA

This application claims benefit of U.S. Provisional Application Ser. No. 60/023,353, filed Aug. 20, 1996.

REFERENCE TO GOVERNMENT GRANTS

This work may have been supported in part by funds from the National Cancer Institute and the National Institute of Neurologial Disorders and Strokes, grant number NS27042. The United States Government may have certain rights in this invention.

BACKGROUND OF THE INVENTION

For an *Escherichia coli* cell to duplicate itself, three important processes must be completed. The cell must first accurately replicate its DNA. The newly formed chromosomes must then be resolved and segregated. An accurately placed septum at the midpoint of the cell must be made to ensure that each newly formed daughter cell receives a full complement of the cellular components. Over the past 30 years, studies investigating the *E. coli* cell cycle have identified many of the genes involved in these processes. However, identification of the internal signals that regulate these processes has been elusive.

At least 13 proteins are involved in the process of DNA replication (Kornberg and Baker, 1992.) The disclosures of each patent, patent application and publication cited or described in this document are hereby incorporated herein by reference, in their entirety. Initiation begins at a specific site, oriC, when DnaA binds to four dnaA boxes located within oriC (Kornberg and Baker, 1992). After loading of the other proteins (including DNA polymerase III, helicase, and primase) involved in the primosomal complex, replication proceeds bidirectionally until it reaches a site located approximately 180° from oriC where replication terminates (ter). Termination requires two inverted ter sequences and the action of the Tus protein (Kornberg and Baker, 1992).

The era gene was discovered by sequencing downstream of the rnc gene in *E. coli* (Ahnn et al., 1986). The nomenclature for this gene and protein follows: Era represents the bacterial protein, era represents the bacterial gene, ERA represents the human protein, and ERA represents the human gene. The era gene is named for the initial identification of the gene from *E. coli*, (for *E. coli* ras). The era gene is a member of the rnc-era-recO rnc operon (Takiff et al., 1989). The rnc gene encodes the protein RNaseIII, which is an RNA endonuclease that plays a role in the processing of several RNA transcripts in *E. coli* (Bram et al., 1980; Gegenheimer and Apirion, 1981; King et al., 1986). Examples of RNA molecules processed by RNaseIII include rRNA transcripts, in which RNaseIII provides the initial cleavage in the maturation of precursor 30S rRNA to the functional 23S rRNA and 16S rRNA molecules, and the rnc operon, in which RNaseIII cleaves the transcribed message at a RNA hairpin found in the leader region of the operon (Bram et al., 1980; Gegenheimer and Apirion, 1981; King et al., 1986). This cleavage is important for the autoregulation of the rnc operon (Bardwell et al., 1989). The era gene in *E. coli* encodes a GTPase that has been proposed to play roles in the cell cycle, cell division, and growth rate (Ahnn et al., 1986; Gollop and March, 1991a; Gollop and March, 1991b). The RecO protein is involved in the RecF recombination pathway (Weinstock, 1987). Of the three genes, only the era gene is required for viability in *E. coli* (Takiff et al., 1989).

Presently the essential function of Era is unknown. Biochemical and cell biological studies of Era have been performed to attempt to elucidate the function of Era. The Era protein autophosphorylates in a GTP-dependent manner, however the function of the phosphorylated form of the protein in vivo is unknown (Sood et al., 1994). Immunoelectron microcopy to determine where Era localizes on the membrane showed that the protein is found near regions of potential division sites in *E. coli* (Gollop and March, 1991 a). The Era protein binds to the membrane in a GTP-dependent manner (Lin et al., 1994). The component of the membrane Era binds has not been discovered.

Morphological analysis of a strain in which the expression of era is repressed at low temperatures showed that cells formed long filaments in the absence of the Era protein (Gollop and March, 1991b). Based on these results and the localization of Era to potential division sites Gollop and March proposed that era may be involved in cell division (Gollop and March, 1991b). However, a similar type of strain construction where era is no longer expressed at high temperatures did not cause cells to filament, thus it is unclear whether decreased era expression results in an inhibition of cell division (Lerner and Inouye, 1991).

Proteins that comprise the GTPase superfamily have been discovered in organisms ranging from *Escherichia coli* to humans (Bourne et al., 1991). These proteins are turned "on" by the binding of GTP and "off" by the hydrolysis of GTP to GDP, thereby acting as a molecular switch (Bourne et al., 1991). The binding of GTP causes a conformational change in the protein that allows interaction with a target molecule (Bourne et al., 1991). GTPases are involved in diverse cellular processes such as signal transduction, protein translocation, and cell cycle regulation (Bourne et al., 1991). Much attention has focused on the small molecular weight GTPase ras and members of the ras subfamily of GTPases due to the identification of ras mutations in human cancer (Marshall, 1985).

Little is known about the functions of bacterial GTPases with respect to their possible role in the regulation of the bacterial cell cycle. However, GTPases are now being shown to play important roles in the cell cycles of bacteria. Recently it has been determined that a key cell division protein in *E. coli*, FtsZ, is a GTPase and requires GTP to polymerize in vitro (De Boer et al., 1992; RayChaudhuri and Park, 1992; Bramhill and Thompson, 1994; Mukherjee and Lutkenhaus, 1994). Also, the Obg protein in *Bacillus subtilus* is a GTPase that may play an important role in sporulation and DNA replication (Kok et al., 1994; Vidwans et al., 1995).

Era has been shown to be able to bind guanine nucleotides and is able to hydrolyze GTP to GDP (Ahnn et al., 1986; Chen et al., 1990). The protein also autophosphorylates in a GTP dependent manner in vitro (Sood et al., 1994). The function of this phosphorylated form of Era is unknown but it has been suggested that it is the active form of the protein (Sood et al., 1994). Binding of Era to the membrane has been demonstrated biochemically (Lin et al., 1994). Lin et al. have proposed that the regulation of Era binding to the membrane is determined within its GTPase activity (Lin et al., 1994).

The present invention describes the characterization of the sdgE class of suppressors. Both suppressors of this class are mutations affecting era, one of which (sdgE1) is a single point mutation within the era coding sequence. This is the first point mutation isolated within the chromosomal copy of era that affects the function of the Era protein without affecting other genes in the rnc operon. This mutation affects the GTPase activity of Era which reveals a cell cycle defect, at or near cell division.

The mechanism of cell division has been elusive in view of the lack of understanding of the roles of various genes thought to be involved in the process. In addition, the number of potential candidate drugs and agents for treating infectious diseases is vast. Accordingly, the development of a rational drug design, in addition to conventional antibiotic treatment, for treating infectious diseases has not progressed at an acceptable rate. With the continuing emergence of antibiotic-resistant pathogenic bacteria, efforts are needed to identify target genes and alternative methods of treating bacterial infectious diseases. To this end, the present invention satisfies this need by providing a method of screening for agents that delay a cell cycle. Accordingly, the present invention provides for methods of reducing or stopping the growth of infectious organisms and thus decreasing or eliminating infection. In addition, in view of the relation between bacterial era and human era, and by analogy to Ras, which Ras is mutated in several types of human cancers, the present invention also provides for a method of screening for anti-cancer agents.

SUMMARY OF THE INVENTION

The present invention is directed to a method of screening for an agent that delays a cell cycle by comparing the activity of an agent suspected of inhibiting Era with a control assay. The level of GDP resulting from the combination of the agent with Era and GTP is compared to the level of GDP of a control assay. Where GDP is reduced in the agent-Era-GTP containing assay as compared to the control assay, an agent that delays a cell cycle is identified.

In addition, another method of screening for an agent that delays a cell cycle comprises comparing the growth of a cell on medium comprising an agent suspected of delaying the cell cycle. The growth of two different cells is compared, one having a heterologous era nucleic acid sequence, and another having wild-type era nucleic acid sequence. The growth of each cell is observed following growth in the medium for an effective amount of time. Slow growth of the cell having a heterologous era sequence as compared to normal growth of the cell having wild-type era sequence results in identification of an agent that delays a cell cycle is also provided in the present invention.

An analogue of wild-type Era, having proline at amino acid 17 replaced with a basic amino acid is also an embodiment of the present invention. A vector, host cell, cell culture, protein preparation, and composition comprising the analogue are additional embodiments of the present invention.

The present invention provides methods that permit the discovery of agents that block certain cell cycles. As a result, a number of diseases may be treated with the agents discovered by the methods of the present invention.

BRIEF DESCRIPTION OF THE DRAWINGS

FIG. 2 (Parts A–C) shows mutations affecting era in sdgE1 and sdgE15. FIG. 2A=Sequence of a portion of the era gene in sdgE1. Note the G-C transversion mutation. FIG. 2B=PCR amplification of the leader region of the rnc operon in wild-type and sdgE15. Lane 1=123 bp ladder. Lane 2=wild-type DNA. Lane3=sdgE15 DNA. FIG. 2C=Summary of the mutations affecting era that suppress dnaGts mutations. A previously identified mutation affecting era, rnc40, is also shown.

FIG. 4 shows doubling times of RABA17 and BSP750.

FIG. 6 displays the alignment of the G1 domain, SEQ ID NOS: 24 and 25, of the GTP binding proteins Era and Human H/N/K Ras. The P17R substitution caused by the era1 mutations shown. Mutations at the analogous position in Ras (Glycine-12) have been shown to be associated with several types of human cancers.

FIG. 8A shows KY2903 (dnaG2903) and FIG. 8B displays BSP754 (dnaG2903, era1) at 42° C. Cells were incubated 42° C. for 2.5 hours and then prepared for microscopy as described in Materials and Methods. Magnification=2000x.

FIG. 9A displays RABA17 and FIG. 9B shows BSP750 (era1) grown at 25° C. Cells were diluted 1:1000 in LB broth and grown to an $A_{600}$ of 0.3. Magnification=2000x.

FIG. 11A=0 hours, FIG. 11B=2 hours, FIG. 11C=3 hours, and FIG. 11D=4 hours during the resumption of protein synthesis. Magnification=2000x.

FIGS. 12A–F exhibits phenotypic analysis of BSP750 (era1) during recovery from inhibition of protein synthesis with chloramphenicol. Photographs were taken at different time points. FIG. 12A=0 hours, FIG. 12B=2 hours, FIG. 12C=3 hours, FIG. 12D=4 hours, FIG. 12E=5 hours, and FIG. 12F=6 hours during the resumption of protein synthesis. Magnification=2000x.

FIG. 13A=W3110, one nucleoid cell. FIG. 13B=era1, one nucleoid cells. FIG. 13C=W3110, two nucleoid cells. FIG. 13D=era1, two nucleoid cells. FIG. 13E=W3110, four nucleoid cells. FIG. 13F=era1, four nucleoid cells.

FIG. 15A=BSP848 (rnc40, λ vector control). FIG. 15B=BSP850 (rnc40, λ-rnc⁺). FIG. 15C=BSP851 (rnc40, λ-rnc105). FIG. 15D=BSP853 (rnc40, λ-rnc*,era⁺). Magnification=2000×.

FIG. 18 displays amino acid sequence alignment of Era from *F. tularensis* (Ftul), *C. burnetii* (Cbur), *B. subtilis* (Bsub), *E. coli* (Ecol), *H. influenzae* (Hinf), *M. leprae* (Mlep), *S. mutans* (Smut), Synechocystis sp. (Syne), and *M. genitalium* (Mgen), SEQ ID NOS: 26–34, respectively. The consensus sequence, SEQ ID NO: 35, derived from this alignment is shown in the bottom line. Amino acid residues that are highly conserved are indicated by upper-case letters in the bottom line for the consensus sequence. "A" in the consensus sequence represents an amino acid residue that could be different in the nine Era sequences presented. However, "a" in the nine different Era sequences presented indicates identity with the respective amino acid residue in the consensus sequence. Amino acid residues presented as lower-case letters in the nine Era sequences shown indicate differences from the respective residues in the consensus sequence. Periods indicate gaps in the sequences. Boxes A, B, C, and D are conserved domains identified in addition to the G-1, G-3, and G-4 regions that are known to be common to all GTP-binding proteins (Bourne et al., 1991).

FIG. 19 is a nucleic acid sequence of human ERA, SEQ ID NO: 36.

FIG. 20 is an amino acid sequence of human ERA, SEQ ID NO: 37.

DETAILED DESCRIPTION OF THE INVENTION

Figure 1:
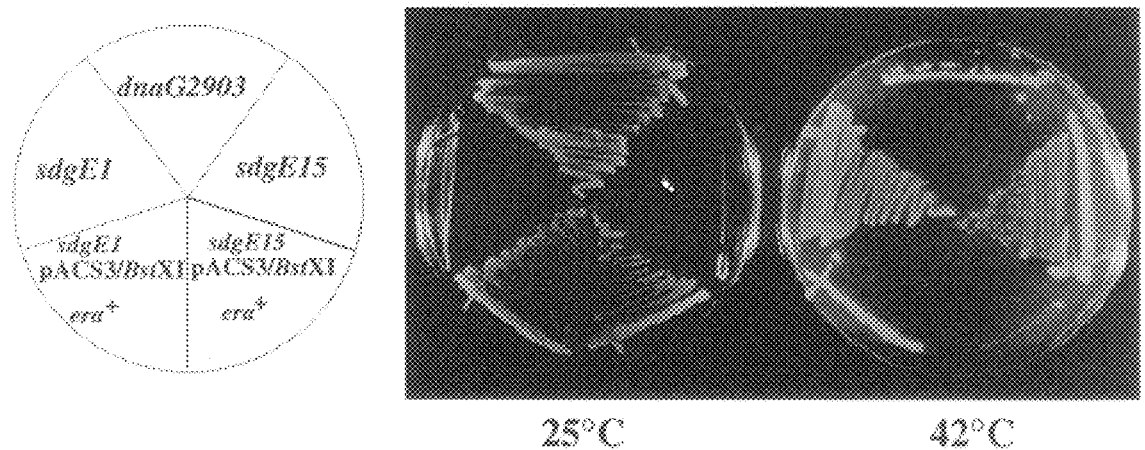
FIGS. 1A and B displays complementation of suppression by pACS3/BstXI (era$^+$). KY2903 (dnaG2903) is temperature-sensitive at 42° C. The suppression of temperature-sensitivity and slow growth at 25° C. is associated with the suppressor mutations sdgE1 and sdgE15. Plasmid pACS3/BstXI, which only contains the era gene, is able to reverse suppression (yield the original dnaG2903 phenotype) in both sdgE1 and sdgE15.

In the context of the present invention, "Era protein moiety" is defined to be at least one of Era (bacterial protein) or ERA (human protein). Further, "era gene moiety" is defined to be at least one of era (bacterial gene) or ERA (human gene). These two definitions are solely for convenience.

The present invention is directed to a method of screening for an agent that delays a cell cycle comprising preparing a purified Era, preparing at least one agent suspected of inhibiting Era, combining said purified Era and said agent with GTP to form a Era-agent-GTP combination, measuring GDP resulting from said combination, and comparing GDP resulting therefrom with GDP resulting from a control, wherein GDP resulting from said combination is reduced compared to GDP resulting from said control thereby identifying an agent that delays a cell cycle.

In addition, a method of screening for an agent that delays a cell cycle comprising preparing a cell having a heterologous era nucleic acid sequence, preparing a cell having wild-type era nucleic acid sequence, exposing each of the cells for an effective time to an agent suspected of delaying a cell cycle, and observing the growth of each cell whereby slow growth of cell harboring a heterologous era and normal growth of the cell harboring the wild-type era result in identification of an agent that delays a cell cycle is also provided in the present invention.

In view of conserved sequences of GTPases, the cell cycle that is delayed may be selected from any cell such as any cell that is recognized as foreign to the organism which it infects. Organisms which may be infected include and are not limited to mammals, such as and not limited to humans, and any other organism from mammal to bacteria. A foreign cell may be a microorganism such as and not limited to a bacterium of the Genus Escherichia, Francisella, Salmonella, Coxiella, Streptococcus, Bacillus, Haemophilus, Mycobacterium, Mycoplasm, Pseudomonas, Synechocystis, and the like. In addition to bacterial infections, infection by other pathogens is within the scope of the invention. A foreign cell may also be a cell usually recognized by the organism as self, which self cell is mutated in era such that it no longer expresses the wild-type Era and no longer recognized as self. Examples of foreign cells of this definition include viral and fungal pathogens, cancer cells, neoplastic cells, metastasized cells, and the like. Era, an essential GTPase, is the preferable GTPase useful in the method of the present invention in identifying agents that delay the cell cycle.

Era is a protein essential to a cell cycle. For purposes of the present invention, Era represents a protein in the GTPase superfamily which is involved in the cell cycle of organisms from bacteria to mammals, including humans. While not intending to be bound by any particular theory of operation, it is believed that Era acts at about the time of cell division. "About the time of cell division" refers to at or near the point of cell division. That is, following DNA replication and nucleoid formation, wild-type Era is involved in cell division, cell cycling, and septum formation. Other GTPases have substantially similar activity. For purposes of the present invention, screening may include any one or more of the following characteristics: identifying an agent that inhibits the activity of Era, inhibits GTPase activity, inhibits GDP formation, inhibits GTP binding to Era, inhibits cell division, inhibits septum formation, arrests cell growth, and decreases infection. The word "delay" and variations thereof are used herein synonymously with inhibit, reduce, suppress, retard, slow, and suspend. Further, agents may be identified that completely inhibit cell division such that it is arrested, stopped, or blocked. Further to these definitions, in accordance with the method of screening for an agent that delays a cell cycle using a heterologous era sequence, agents which inhibit any protein, proteins including and not limited to Era, in a cell cycle may be identified. Indeed, membrane binding proteins and GTPase activation by other proteins may be identified as delaying a cell cycle. In accordance with the claimed invention, a cell in which the cell cycle is delayed is one which is unable to display cell division typically seen in that cell type under normal conditions. Accordingly, the present invention includes the identification of agents that substantially inhibit cell division. Substantial inhibition of cell division refers to less than about 1% to about 100% of the cells of a given population are inhibited. Preferably cell division is inhibited about 10%, more preferably about 20%, more preferably about 50%, even more preferably about 75%, even more preferably about 100%.

A gene coding for Era may be obtained from a cDNA or genomic library. Suitable libraries can be obtained from commercial sources such as Clontech, Palo Alto, Calif. Libraries may also be prepared using the following non-limiting examples hamster insulin-secreting tumor (HIT), mouse αTC-6, a muscle cell library, and rat insulinoma (RIN) cells. Positive clones are then subjected to DNA sequencing to determine the presence of a DNA sequence coding for Era. DNA sequencing may be accomplished using the chain termination method of Sanger et al. 1977. The DNA sequence encoding Era is then inserted into an expression vector for later expression in a host cell.

Briefly, cells are transformed using any of the methods known in the art such as those disclosed by Sambrook, et al., 1989, such as and not limited to calcium chloride transformation, rubidium chloride transformation, or electroporation. Expression vectors and host cells are selected to form an expression system capable of synthesizing Era. As used herein, expression vectors refer to any type of vector that can be manipulated to contain a nucleic acid sequence coding for Era, such as plasmid expression vectors and viral vectors. Plasmid expression vectors comprise a nucleic acid sequence of the invention operably linked with at least one expression control element such as a promoter. In general, plasmid vectors contain replicon and control sequences derived from species compatible with the host cell. To facilitate selection of plasmids containing nucleic acid sequences of the invention, plasmid vectors may also contain a selectable marker such as a gene coding for antibiotic resistance. Suitable examples include the genes coding for ampicillin, tetracycline, chloramphenicol or kanamycin resistance. Vectors including and not limited to baculovirus vectors may be used in the present invention. The vector preferably has a strong promoter that is tightly controlled and inducible. Nonlimiting examples of tightly controlled promoters include temperature sensitive promoters, such as those which increase expression of Era at a particular temperature, and pET (Novagen), which contains a T7 promoter and T7 RNA polymerase under control of a lac promoter. Strains containing T7 promoters include BL21 and HMS174. Host cells suitable for use in the invention include prokaryotic and eukaryotic cells that can be transformed to stably contain and express Era. For example, nucleic acid coding for the protein may be expressed in prokaryotic or eukaryotic host cells, including the most commonly used bacterial host cell for the production of recombinant proteins, *E. coli*. Other microbial strains may also be used, however, such as *Bacillus subtilis*, and other enterobacteriaceae such as *Salmonella typhimurium* or *Serratia marcescens*, various species of Pseudomonas, or other bacterial strains. Suitable expression vectors, promoters, enhancers, and other expression control elements are known in the art and may be found in Sambrook et al., 1989.

Transformed host cells containing a DNA sequence encoding Era may then be grown in an appropriate medium for the host. The cells are then grown until product accumulation reaches desired levels at which time the cells are then harvested and the protein product purified in accordance with conventional techniques. Era may be purified by any method of protein purification known to skilled artisans such as the techniques set forth herein and by Sambrook, et al., 1989 and Chen, et al., 1990. Briefly, a culture of *E. coli* is grown at about 37° C. until reaching an $A_{600}$ of about 0.4 to about 0.5 at which time the culture is shifted to 40° C. and grown in LB broth, for example, for about two hours to allow for expression of Era.

Cells are then lysed and centrifuged to separate insoluble proteins from soluble proteins. The soluble, Era-containing fraction is then precipitated in ammonium sulfate in fractions of between about 5% to about 50% ammonium sulfate, about 10% to about 40% ammonium sulfate, or about 20% to about 30% ammonium sulfate. The ammonium sulfate precipitated soluble fraction is then separated by size, preferably over a column such as a Sepharose or Sephadex column, a G-25 Sepadex column, for example, will separate proteins of about 25 kD or smaller from the larger sized proteins containing Era, having a molecular weight of about 33 kD. The fraction larger than about 25 kD is then separated by charge, such as over a column, a Q-Sepharose column for example. The Era protein is then stored in 50% glycerol and used for subsequent analysis. Other suitable purification methods include, but are not limited to, SDS PAGE electrophoresis, phenylboronate-agarose, reactive green 19-agarose, concanavalin A sepharose, ion exchange chromatography, affinity chromatography, electrophoresis, dialysis and other methods of purification known in the art.

The agents tested in the method of the present invention include any agent suspected of delaying the certain cell cycle. Agents suspected of inhibiting pathogens such as bacteria or any other foreign cell may be identified by the method of the present invention. The screening method may include a cocktail of a number of agents suspected of delaying a cell cycle, such that a sample of agents containing about five to about fifty suspected agents may be tested together. The agents will be tested for their ability to inhibit the GTPase aactivity of purified Era protein. Depending on the results resulting therefrom, smaller groups of the original agents, such as groups of about two to about twenty (depending on the number of agents in the original screen), or each agent of the cocktail, may then be individually tested. In addition to in vitro testing, individual agents (or a combination of agents) that inhibit Era activity may also be tested for their ability to inhibit the growth of bacteria in vivo. Agents may be added to growth media (such as, for example, LB broth, minimal media, and the like) and the growth of bacteria may be monitored.

Era from *E. coli* is the preferred Era useful in the methods of the present invention. "For an effective time" refers to a period of time that would permit GTP to form GDP under normal conditions, from about 20 minutes to about 120 minutes, preferably about 60 minutes, more preferably about 30 minutes at about 35° C. to about 45° C., preferably about 37° C.

Era, as purified according to the methods set forth above, is used in the method of the present invention. About one to about 500 picomoles, more preferably about 10 to about 400 picomoles, more preferably about 20 to about 250 picomoles, and most preferably about 40 picomoles of Era is combined with GTP of about 0.1 $\mu$moles to about 100 $\mu$moles, more preferably about 10 $\mu$moles. ATP may be added to inhibit the GTPase activity of ATPases. The amount of agent added to the Era-GTP combination is dependent on a number of factors such as and not limited to the concentration of agent used, synergy between agents used together in a pool of agents, the dosage of agents useful against other diseases.

The methods of measuring GTPase activity, including methods of measuring GDP, resulting from the combination of Era-agent-GTP combination include any quantitative or qualitative measurement, which are readily known to those of skill in the art, and may be and are not limited to spectrophotometry, densitometry, and chromatography. That is, following the combination for an effective time of Era-agent-GTP, in which GTP may be labeled, a small sample, about one $\mu$l to about five $\mu$ls may be placed on PEI-cellulose for example and thin layer chromatography carried out in 0.5M $KH_2PO_4$, 1M NaCl at room temperature. After autoradiography of the chromatogram, the spots corresponding to GTP and GDP are cut out and counted. The amount of GTP hydrolyzed is calculated. Labels include a radioactive label such as $^{32}p$, biotin, fluorescein, and ethidium bromide. Similarly, spectrophotometry and densitometry may be performed by placing a sample in a spectrophotometer or densitometer and reading the value of the sample as compared to a control in the appropriate apparatus.

Other GTPase assays include and are not limited to those that follow. GTPase hydrolysis may be monitored by measuring free phosphate as described by Welch et al., 1994. After the standard reaction using gamma-$^{32}$ P GTP, the reaction is quenched with a slurry of activated charcoal in 1 mM kPi buffer (pH 7.5) which selectively removes organics including all nucleotides (GTP, GDP, GMP). The charcoal is pelleted by centrifugation and the amount of free $^{32}PO_4$ is quantified by Cherenkov counting of the supernatant. Alternatively, the rate of hydrolysis may be monitored using the fluorescent GTP analog 3'-mdGTP according to the methods set forth in *Methods in Enzymology*, 1995 255:95–107 or Moore and Lohman, 1994. Nucleotide binding and hydrolysis is measured using a fluorescence spectrometer. Another alternative is to measure activity by immunoprecipitation of the Era-nucleotide complex as disclosed in *Methods in Enzymology*, 1995 255:110–125.

Complementation permits the screening of agents having cell cycle delay activity such that a cell having a nonfunctioning or null era nucleic acid sequence may be complemented by a heterologous era sequence. The heterologous era sequence may be incorporated, such as by transformation, into the cell genome or harbored on a plasmid or vector. A cell comprising the heterologous era sequence is grown for an effective time on or in a medium containing the agent suspected of having cell cycle delay activity. era genes from other organisms may be identified by identifying them in genomes from organisms whose DNA has been sequenced. Complementation may be carried out by methods known to those of skill in the art such as according to the methods set forth in the examples below and methods of Sambrook et al., 1989, and Miller, 1992. A nonfunctioning era sequence may be obtained by removing the protein from control of the natural promoter such as by splicing into the genome additional sequences that contain a promoter causing the cell to become dependent thereon. Such an example of a promoter is an antibiotic resistant promoter such as and not limited to tetracycline, ampicillin, kanamycin; arabinose, T7, lactose, λ thermosensitive promoter, and the like. A library is then constructed with vectors appropriate to the size of the sequence to be cloned, the library is then screened. Growth on or in a medium includes plating or growing the cells on plates comprising solid medium or growing the cells in liquid culture medium.

Once heterologous era sequences are identified, they can be used to construct *E. coli* organisms that depend only on the heterologous era gene for growth. For example, the era gene from another bacterium, such as *Helicobacter pylori*, can be used to functionally replace the era gene in the chromosome of *E. coli*. Replacement of the *E. coli* era gene with the *H. pylori* era gene can be performed by complementing an era defect with the *H. pylori* era gene. The resulting strain is the same as a wild-type *E. coli* strain, except that it has the era gene from *H. pylori*. These two strains are then grown on culture media LB, minimal media, or the like, that contain agents and the growth of the two strains are compared. Any agent that inhibits the growth of the *E. coli* strain with the *H. pylori* era gene but not the wild-type *E. coli* strain is found to inhibit the *H. pylori* Era protein. This agent (or combination of agents) is then tested to see if it inhibits the growth of an *H. pylori* strain. Such an agent would then be a candidate for a treatment against *H. pylori*.

era is the second gene in the polycistronic rnc operon of *E. coli* and is flanked upstream by rnc and downstream by recO (Ahnn et al., 1986; Morrison et al., 1989; Takiff et al., 1989). Heterologous genetic complementation may be achieved in bacteria that contains a transposon insertion in the leader sequence of the rnc preventing operon expression from its natural promoter and causing conditional growth of the cell. A genomic library may be constructed, transformed into cells, and selecting for conditional growth, such as for example in the presence of ampicillin ($AMP^R$ may be encoded by a vector). A clone may be obtained that contains an insert that hybridizes to the genomic DNA of the bacterial era on Southern blots.

Heterologous and exogenous, as used herein, denote a nucleic acid sequence that is not obtained from and would not normally form a part of the genetic make-up of the cell to be transformed, in its untransformed state. Accordingly, a heterologous era sequence may be a sequence from another source, which is wild-type for that source. "''For an effective time" refers to a time period that would permit growth of wild-type cells under normal conditions, from about 24 to about 72 hours, preferably about 36 hours, more preferably about 48 hours, at about 35° C. to about 40° C., preferably about 37° C. The preferably era nucleic acid sequence useful in the method set forth above is era from *E. coli*. Alternatively, depending upon the growth conditions of the cell, an effective time may include about one week to about two weeks, as well.

The era gene encodes a protein in the GTPase superfamily that has guanine-nucleotide binding and GTPase activities. While era is the preferred embodiment of the present invention, GTPases in general are also the subject of the present invention. Indeed, GTPases are known to exist in organisms from bacteria to mammals. The sequence of era (*E. coli* ras) gene is set forth in Ahnn et al., 1986. Amino acid 17 of mature wild-type Era, proline, is found to be replaced in era1 of the present invention with a basic amino acid, such as and not limited to arginine, lysine, and histidine. The era1 allele is the first single point mutation within the era gene isolated on the chromosome for which the function of era has been analyzed to the knowledge of the inventors. era1 affects the GTPase activity of Era. The Era1 protein expressed by the era gene revealed a decrease in GTPase activity by about four to about five fold and caused a delay in the cell cycle. Thus, Era1 elucidated the role of wild-type Era; GTPase activity resulting from wild-type Era permits normal cell division and/or a normal cell cycle.

The era1 mutation causes the substitution P17R that occurs at a position in the protein of considerable interest in GTPases. Proline-17 of Era corresponds to Gly-12 in Ras; Gly-12 has been found to be mutated in several types of human cancers (Marshall, 1985). Interestingly, proline is the only amino acid that can be placed in position 12 of ras and not cause the protein to become oncogenic (Seeburg et al., 1984). Proline 17 of era was mutated to valine and when the mutation causing this change was present on a multicopy plasmid with the chromosomal allele of era inactivated, the cells became cold-sensitive (Lerner et al., 1992). Analysis of substitutions of Glycine-12 in Ras has demonstrated that mutants at this position (including G12R) are not defective in GTP or GDP binding and that it is the intrinsic GTPase activity of the protein that is inhibited (Finkel et al., 1984).

Structural analysis of Ras position 12 mutants led to the hypothesis that cleavage of the gamma phosphate of GTP was inhibited by steric hindrance caused by the bulky side chains of amino acids other than glycine (and presumably proline) at position 12 (Krengel et al., 1990). Because GTP binding domains are well conserved, it is likely that the defect in GTPase activity of Era1 is caused by a similar mechanism. The era sequence is conserved among bacteria as well, see Table 7.

Analysis of the GTPase activity of the Era1 protein showed that Era1 has a 4–5 fold decrease in GTPase activity. Era1 was able to bind GTP and GDP similar to wild-type Era, indicating that the protein was still folded properly. This defect in the GTPase activity may be due to reduced cleavage of the gamma phosphate or to a reduced ability of the protein to cycle between its GTP and GDP bound forms. Analysis of substitutions of Glycine-12 in Ras has demonstrated that mutants at this position (including G12R) are not defective in GTP or GDP binding and that it is the intrinsic GTPase activity of the protein that is inhibited (Finkel et al., 1984). Structural analysis of Ras position 12 mutants led to the hypothesis that cleavage of the gamma phosphate of GTP was inhibited by steric hindrance caused by the bulky side chains of amino acids other than glycine (and presumably proline) at position 12 (Krengel et al., 1990). Because GTP binding domains are well conserved, it is likely that the defect in GTPase activity of Era1 is caused by a similar mechanism.

The purified amino acid sequence may comprise all or part of the sequence of Era1, such that a fragment having substantially the same Era activity is included within the scope of the present invention. Fragments of the amino acid sequence of Era include a fragment comprising codon 17, a fragment comprising codon 21, and a fragment comprising each of codon 17 and codon 21. Mutations which do not substantially alter the activity of the sequence or part of the sequence are embodied by the present invention. Nucleic acids which encode the amino acid sequences of Era1 within in the scope of the present invention include cDNA, RNA, genomic DNA, sequences within these larger sequences, antisense oligonucleotides. Variations in the nucleic acid and polypeptide sequences of the present invention are within the scope of the present invention and include N terminal and C terminal extensions, transcription and translation modifications, and modifications in the cDNA sequence to facilitate and improve transcription and translation efficiency. In addition, mismatches within the sequences identified herein, which achieve the methods of the invention, such that the mismatched sequences are substantially complementary to the Era sequences identified, are also considered within the scope of the present invention. Mismatches which permit substantial complementarity to the Era sequences, such as similarity in residues in hydrophobicity, will be known to those of skill in the art once armed with the present disclosure. In addition, the sequences of the present invention may be natural or synthetic.

In addition to the Era1 protein set forth above, Era homologs, including a human ERA, different from human Ras, and Era from *C. elegans*, are within the scope of the invention. The human ERA nucleic acid is set forth in FIG. 19, SEQ ID NO: 36, the human ERA amino acid sequence is set forth in FIG. 20, SEQ ID NO: 37. The definition of these Eras include all of the sequence variations in set forth above for bacterial Era, including alternatively spliced sequences and fragments of the sequences which are substantially similar or have substantially the same activity of the sequences of FIGS. 19 and 20. It is the human ERA which is the preferred protein for use in detecting an agent that delays a foreign cell cycle, which agent is useful as an anti-cancer treatment.

The term "purified", when used to describe the state of the protein of the invention, refers to a protein substantially free of other cellular material including proteins not coding for Era or other materials such as those normally associated with nucleic acid in non-recombinant cells, i.e., in its "native state."

The term "purified" or "in purified form" when used to describe the state of Era protein, polypeptide, or amino acid sequence, refers to Era free, to at least some degree, of cellular material or other material normally associated with it in its native state. Preferably the protein has a purity (homogeneity) of at least about 25% to about 100%. More preferably the purity is at least about 50%.

Generally, the protein of the invention may be produced in host cells transformed with an expression vector comprising a nucleic acid sequence encoding Era. The transformed cells are cultured under conditions whereby the nucleic acid sequence coding for the Era is expressed. After a suitable amount of time for the protein to accumulate, the protein is purified from the transformed cells.

A gene coding for Era may be obtained from a cDNA or genomic DNA library. Suitable libraries can be obtained from commercial sources such as Clontech, Palo Alto, Calif. Libraries may also be prepared using the following non-limiting examples hamster insulin-secreting tumor (HIT), mouse αTC-6, muscle cells, and rat insulinoma (RIN) cells. Positive clones are then subjected to DNA sequencing to determine the presence of a DNA sequence coding for Era. DNA sequencing is accomplished using the chain termination method of Sanger et al. 1977. The DNA sequence encoding Era is then inserted into an expression vector for later expression in a host cell.

Expression vectors and host cells are selected to form an expression system capable of synthesizing Era. Vectors including and not limited to baculovirus vectors may be used in the present invention. Host cells suitable for use in the invention include prokaryotic and eukaryotic cells that can be transformed to stably contain and express Era. For example, nucleic acid coding for the protein may be expressed in prokaryotic or eukaryotic host cells, including the most commonly used bacterial host cell for the production of recombinant proteins, *E. coli*. Other microbial strains may also be used, however, such as *Bacillus subtilis*, and other enterobacteriaceae such as *Salmonella typhimurium* or *Serratia marcescens*, various species of Pseudomonas, or other bacterial strains.

Commonly used eukaryotic systems include yeast, such as *Saccharomyces cerevisiae*; insect cells, such as *Spodoptera frugiperda*; chicken cells, such as E3C/O and SL-29; mammalian cells, such as HeLa, Chinese hamster ovary cells (CHO), COS-7 or MDCK cells and the like. The foregoing list is illustrative only and is not intended in any way to limit the types of host cells suitable for expression of the nucleic acid sequences of the invention.

As used herein, expression vectors refer to any type of vector that can be manipulated to contain a nucleic acid sequence coding for Era, such as plasmid expression vectors and viral vectors. The selection of the expression vector is based on compatibility with the desired host cell such that expression of the nucleic acid encoding Era results. Plasmid expression vectors comprise a nucleic acid sequence of the invention operably linked with at least one expression control element such as a promoter. In general, plasmid vectors contain replicon and control sequences derived from species compatible with the host cell. To facilitate selection of plasmids containing nucleic acid sequences of the invention, plasmid vectors may also contain a selectable marker such as a gene coding for antibiotic resistance. Suitable examples include the genes coding for ampicillin, tetracycline, chloramphenicol or kanamycin resistance.

Suitable expression vectors, promoters, enhancers, and other expression control elements are known in the art and may be found in Sambrook et al., 1989.

Transformed host cells containing a DNA sequence encoding Era may then be grown in an appropriate medium for the host. The cells are then grown until product accumulation reaches desired levels at which time the cells are then harvested and the protein product purified in accordance with conventional techniques. Suitable purification methods include, but are not limited to, SDS PAGE electrophoresis, phenylboronate-agarose, reactive green 19-agarose, concanavalin A sepharose, ion exchange chromatography, affinity chromatography, electrophoresis, dialysis and other methods of purification known in the art.

Protein preparations, of purified or unpurified Era produced by host cells, are accordingly produced which comprise Era and other material such as host cell components and/or cell medium, depending on the degree of purification of the protein.

The era gene was sequenced in accordance with standard techniques known to those of skill in the art once armed with the present disclosure, such as Ahnn et al., 1986, and Sambrook, et al., 1989. The method of amplifying nucleic acids may be the polymerase chain reaction (PCR) using a pair of primers wherein at least one primer within the pair is selected from the group consisting of SEQ ID NOS: 9–16.

A number of template dependent processes are available to amplify the target sequences of interest present in a sample. One of the best known amplification methods is the polymerase chain reaction (PCR) which is described in detail in U.S. Pat. Nos. 4,683,195, 4,683,202 and 4,800,159, and in Innis et al., 1990. PCR is performed using a pair of primers wherein at least one primer within the pair is selected from the group consisting of SEQ ID NOS: 9–16. In addition, other methods known to skilled artisans for amplifying nucleic acids may be used in place of PCR, such as and not limited to LCR disclosed in EPA No. 320,308, Qbeta Replicase, described in PCT Application No. PCT/US87/00880, isothermal amplification methods, disclosed in Walker, G. T., et al., 1992, transcription-based amplification systems (TAS) (Kwoh D., et al., 1989, Gingeras T. R., et al., PCT Application WO 88/10315, including nucleic acid sequence based amplification (NASBA) and 3SR, Davey, C., et al., European Patent Application Publication No. 329,822, disclose a nucleic acid amplification process involving cyclically synthesizing single-stranded RNA ("ssRNA"), ssDNA, and double-stranded DNA ("dsDNA") which may be used in accordance with the present invention. Miller, H. I., et al., PCT application WO 89/06700, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "race" disclosed by Frohman, M. A., 1990) and "one-sided PCR" (Ohara, O., et al., 1989).

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and which involves annealing several probes throughout a region targeted for amplification, followed by a repair reaction in which only two of the four bases are present. The other two bases can be added as biotinylated derivatives for easy detection. A similar approach is used in SDA.

Era specific nucleic acids can also be detected using a cyclic probe reaction (CPR). In CPR, a probe having a 3' and 5' sequences of non-era specific DNA and middle sequence of era specific RNA is hybridized to DNA which is present in a sample. Upon hybridization, the reaction is treated with RNaseH, and the products of the probe identified as distinctive products, generate a signal which is released after digestion. The original template is annealed to another cycling probe and the reaction is repeated. Thus, CPR involves amplifying a signal generated by hybridization of a probe to an era specific expressed nucleic acid.

Still other amplification methods described in GB Application No. 2 202 328, and in PCT Application No. PCT/US89/01025, may be used in accordance with the present invention. In the former application, "modified" primers are used in a PCR like, template and enzyme dependent synthesis. The primers may be modified by labelling with a capture moiety (e.g., biotin) and/or a detector moiety (e.g., enzyme). In the latter application, an excess of labelled probes are added to a sample. In the presence of the target sequence, the probe binds and is cleaved catalytically. After cleavage, the target sequence is released intact to be bound by excess probe. Cleavage of the labelled probe signals the presence of the target sequence.

Methods based on ligation of two (or more) oligonucleotides in the presence of nucleic acid having the sequence of the resulting "di-oligonucleotide", thereby amplifying the di-oligonucleotide (Wu, D. Y. et al., 1989), may also be used in the amplification step of the present invention.

The following examples are illustrative but are not meant to be limiting of the invention.

EXAMPLES

Strains And Genetic Techniques

The strains used in this study are listed in Table 1. P1 transductions using P1vir were performed as described (Miller, 1972). Electroporations were done using the Gene Pulser II apparatus (Bio-Rad) as per manufacturer specifications. Cell were grown in LB broth (10 g of tryptone, 5 g of yeast extract, 10 g of NaCl). Bactoagar (15 g) was added to LB broth to make plates. Antibiotics timentin (50 μg/ml), kanamycin (30 μg/ml) and tetracycline (15 μg/ml) were added when necessary. Restriction enzymes were purchased from New England Biolabs and Boehringer Mannheim. Taq polymerase was purchased from Cetus.

TABLE 1

| Bacterial Strains | | |
| --- | --- | --- |
| Strain | Relevant Genotype | Source |
| W3110 | prototroph | E. coli Genetic Stock Center, Yale University, New Haven, CT |
| RABA17 | W3110, TD1-17::ΔTn10 | W3110 transduced by P1 generalized transduction as per Miller, 1989. |

TABLE 1-continued

Bacterial Strains

| Strain | Relevant Genotype | Source |
|---|---|---|
| JV53 | parB linked to Cm$^r$ | Versalovic (1994). Evolution of the macromolecular synthesis operon and analysis of bacterial primase. Ph. D. Thesis. Baylor College of Medicine, Houston, TX. |
| KY2903 | W3110, dnaG2903 | Murakami, Y., et al., 1985. |
| RABPARB | MG1655, parB linked to Cm$^r$ | P1 transduction of JV53 into MG1655 and selecting for Cmr and temperature sensitivity (parB). |
| RAB10 | W3110, parB linked to Cm$^r$ | Transduction of RABPARB into W3110 with same selection as RABPARB above |
| SDG1 | W3110, dnaG2903, sdgE1 (era1), ΔTn10 | RAB2903 (KY2903 Δtn10, proC$^-$) spontaneous suppressor of RAB2903 |
| SDG15 | W3110, dnaG2903, sdgE15 (rnc15), ΔTn10 | RAB2903 (KY2903 Δtn10, proC$^-$) spontaneous suppressor of RAB2903 |
| RAB1 | W3110, dnaG2903, era1 | P1 transduction of W3110 into SDG1, selecting for proC$^+$, then checked for Tc sensitivity. |
| RAB15 | W3110, dnaG2903, rnc15 | P1 transduction of W3110 into SDG15, selecting for proC$^+$, then checked for Tc sensitivity. |
| HT120 | W3110, rnc40::ΔTn10 | Takiff et al., 1989 |
| HT31 | N4903, TD1-17::ΔTn10 | Takiff et al., 1989 |
| BSP750 | W3110, era1, TD1-17::ΔTn10 | P1 transduction of W3110 with BSP754 |
| BSP754 | W3110, dnaG2903, era1 TD1-17::ΔTn10 | P1 transduction of RAB1 with HT31 |
| BSP756 | W3110, parB, era1 TD1-17::ΔTn10 | P1 transduction of RAB10 with BSP750 |
| BSP751 | W3110, rnc15 TD1-17::ΔTn10 | P1 transduction of W3110 with BSP755 |
| BSP755 | W3110, dnaG2903, rnc15 TD1-17::ΔTn10 | P1 transduction of RAB15 with HT31 |
| BSP757 | W3110, parB, rnc15 TD1-17::ΔTn10 | P1 transduction of RAB10 with BSP550 |
| TAP106 | N4956, (λkil cI857Δbio) N::kan | Patterson, T. A., et al., 1993. |

Identification Of era As The Gene Responsible For Suppression In The sdgE Class Of Suppressors Two suppressors of dnaG2903, sdgE1 and sdgE15 mapped near a marker located at 58.2' on the E. coli chromosome. A shotgun library of the E. coli chromosome was electroporated into SDG1 (sdgE1) in an effort to identify plasmids that could reverse the suppression in this mutant. Transformants were selected based on their ability to form colonies at 25° C. after two days and then tested for growth at 42° C. Four plasmids, pBL301-1, pBL301-2, pBL301-3, and pBL301-4, were able to restore colony formation at 25° C. after two days and reverse the suppression of sdgE1; that is strains harboring these plasmids could no longer grow at 42° C. and could form colonies on plates at 25° C. after 2 days. This demonstrated that each plasmid likely contained the gene responsible for suppression in sdgE1. All four plasmids were electroporated into SDG15 (sdgE15) and in each case suppression was reversed, suggesting that the same gene was responsible for suppression in both strains.

The map locations of pBL301-1 and pBL301-4 were determined by hybridization of the plasmids to the E. coli genome mapping Kohara filter. The Kohara filter contains 476 phage λ clones that contain greater than 99% of the E. coli genome. Both plasmids hybridized to overlapping λ clones 7G4 (434) and 4A12 (435), which contain DNA from the 58.0' region of the E. coli chromosome. Thus two independent methods have localized the gene responsible for suppression in this class to the 58.0' region of the chromosome. Restriction mapping of the pBL301 plasmids was performed to determine which genes were contained in the chimeric pBL plasmids. Digestion of the DNA with BamHI and EcoRI identified two common bands among all four of the plasmids that were approximately 1.4 and 1.6 kb in size. Genes encoded within this 3 kb of DNA include rnc, era, recO, lepB, and pdxJ.

To identify which of these genes was responsible for suppression of dnaG2903, plasmids containing various combinations of genes from the rnc operon were electroporated into strains SDG1 (sdgE1) and SDG15 (sdgE15). The plasmid pDLC142 contains the rnc, era, and recO genes and was able to reverse suppression in both SDG1 and SDG15 (Table 2). The plasmid pACS3, which contains only rnc and era, was also able to reverse suppression. The plasmid pACS21 contains only the rnc gene and was unable to be transformed into either SDG1 and SDG15, suggesting that overexpression of RNaseIII is lethal in both strains. pACS3/BstXI is a plasmid in which the rnc gene has been inactivated, leaving era as the only functional gene on the plasmid. This plasmid was also able to reverse suppression, clearly demonstrating that era was the gene responsible for suppression in the sdgE class of suppressors (see FIG. 1).

TABLE 2

Effect of genes in the rnc operon on suppression in sdgE1 and sdgE15

| | | Reverse suppression of | |
|---|---|---|---|
| Plasmid | Genes | sdgE1 | sdgE15 |
| pBR322 | none | No | No |
| pDLC142 | rnc, era, recO | Yes | Yes |
| pACS3 | rnc, era | Yes | Yes |
| pACS3/BstXI | era | Yes | Yes |
| pACS21 | rnc | No$^b$ | No$^b$ |

Sequence Analysis Of The era Gene In sdgE1 And sdgE15

Direct DNA sequencing of PCR products was performed in accordance with the teachings of Sambrook, et al., 1989. Primers used in sequencing the rnc gene were rnc1:

TTGGCGGCATCCATTAATAGCC, SEQ ID NO: 1, nrc2:

GGCACTACGATGAGTTAATGCC, SEQ ID NO: 2, nrc3:

AACCCCATCGTAATTAATCGGC, SEQ ID NO: 3, nrc4:

TTGAGGATTAATTTCTCGACGG, SEQ ID NO: 4, nrc5:

CGTCGTGAGTCAATTCTCGCCG, SEQ ID NO: 5, nrc6:

CACTCAGGCCGACTGACCTGGC, SEQ ID NO: 6, nrc7:

GGTCGTCCATCTGCCGCTGCCG, SEQ ID NO: 7, and nrc8:

CGAGTTGTCTGCGCCTTGCGGG, SEQ ID NO: 8.

Primers used in sequencing the era gene were era1:
GGTGGTTGGCACAGGTTCAAGCCG, SEQ ID NO: 9, era2:

ACATCGCCAATAGAGCTGCTCGCC, SEQ ID NO: 10, era3:

CGATCTACGTCGATACACCGGGCC, SEQ ID NO: 11, era4:

-continued

TAGATGCTTACGCACGATTGCCGC,SEQ ID NO: 12, era5:

GATGAACTTCCTCGATATCGTGCC,SEQ ID NO: 13, era6:

ATGTCTTTACGCGCTTCAATCCCG,SEQ ID NO: 14, era7:

TGATTCTCGTTGAGCGTGAAGGGC,SEQ ID NO: 15, and era8:

TTGGCAACCAGACGCACGCGCCCC,SEQ ID NO: 16.

The era gene from sdgE1 and sdgE15 bearing strains was sequenced to determine the nucleotide changes within era that are responsible for suppression of dnaG2903. The sdgE1 mutation was found to result from a single transversion point mutation at nucleotide 50 that causes a Pro-to-Arg (P17R) substitution at amino acid 17 (FIG. 2A). This nucleotide substitution destroys a BsiYI site within the era gene. Restriction analysis with BsiYI of a PCR amplified product from genomic DNA of a sdgE1 harboring strain confirmed the presence of the mutation. The P17R mutation occurs in the G1 region of the GTP-binding domain in era. The sdgE1 mutation will now be referred to as era1.

No mutation was found within the era gene in sdgE15; therefore the rnc gene and promoter region of the rnc operon were sequenced. PCR amplification of the promoter region in sdgE15 with primers rnc1 and rnc2 should yield a 370 bp fragment of DNA. However, this fragment was found to be close to 1.1 kb in sdgE15 (FIG. 2B). Partial DNA sequencing of this fragment and subsequent computer analysis identified a 100 % match to the IS1 element of E. coli. IS1 elements are 729 bp in length, accounting for the increased size of the PCR product. The insertion of this element occurred one nucleotide after the stem-loop structure in the leader region of the operon and likely exerts a polar effect on the expression of all three genes. No mutation in the rnc gene was found. As shown above by the growth characteristics of sdgE15 harboring strains, it is most likely that the polar effect on the era gene is responsible for both the suppression of dnaG2903 and slow growth at 25° C. The sdgE15 mutation will now be referred to as rnc15. A summary of the mutations and their location in the rnc operon are shown in FIG. 2C.

Suppression Of dnaG2903 And parB By rnc40

A previously identified mutation known to affect the expression of era was tested for suppression of dnaG2903 and parB. The rnc40 allele is a ΔTn10 insertion into the leader region of the rnc operon (FIG. 2C). This insertion blocks transcription from the rnc promoter. Expression of the rnc operon was proposed to be driven by the tetracycline-induced promoter of the tetR gene encoded within the ΔTn10 element (Takiff et al., 1989). Strains containing the rnc40 mutation are unable to form colonies in the absence of tetracycline at low temperatures. This conditional-lethal phenotype can be corrected by plasmids containing the era gene (Takiff et al., 1989).

Figure 3:
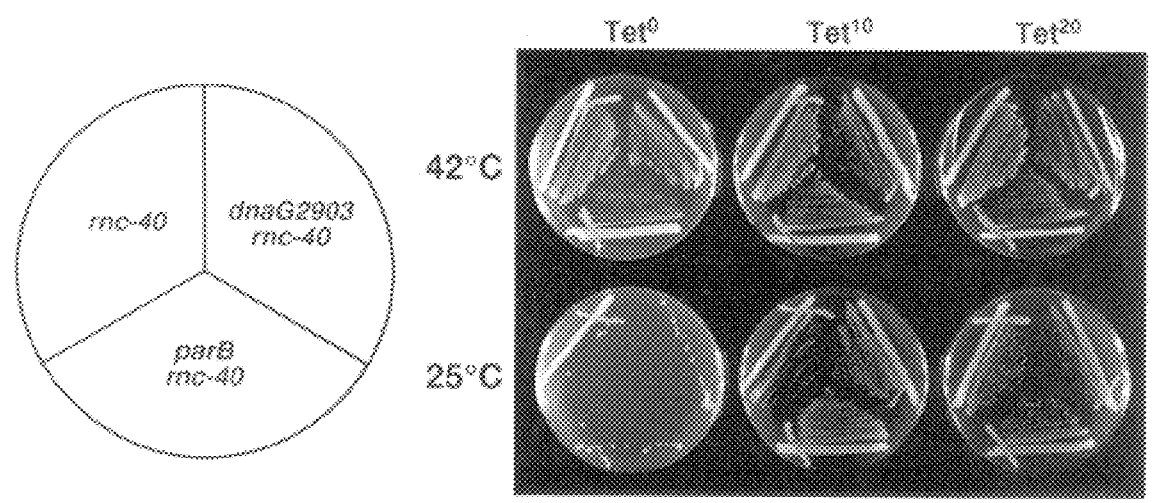
FIG. 3 exhibits suppression of the temperature sensitivity of dnaG2903 and parB by rnc40. Cells were grown at 42° C. and 25° C. on LB plates containing either no tetracycline or tetracycline at final concentrations of 10 $\mu$g/ml or 20 $\mu$g/ml.

The rnc40 mutation was transduced using P1vir into dnaG2903 and parB at 30° C. by selecting for tetracycline resistance. Presence of the rnc40 allele was confirmed by absence of colony formation at 25° C. on LB plates containing no tetracycline (FIG. 3). Both dnaG2903 and parB are suppressed at 42° C. by the rnc40 mutation, demonstrating that a second polar mutation affecting era expression can also suppress dnaG$^{ts}$ FIG. 3. Suppression also occurred in the presence of tetracycline, confirming the previous observation that expression of the tetR promoter does not reach wild-type levels (FIG. 3).

Suppression Of parB By rnc15 And era1

To test if the rnc15 and era1 mutations were allele specific, the rnc15 and era1 mutations were transduced into RAB10 (parB) creating strains BSP757 and BSP756, respectively. In both cases the temperature-sensitivity of parB was suppressed. Attempts to transduce rnc15 and era1 into dnaG3 and dnaG308 were unsuccessful presumably due to the poor growth of these dnaG alleles at the permissive temperatures.

Tests For rnc And recO Phenotypes

The rnc phenotype of strains was tested by plating λ on E. coli as described (Takiff et al., 1989). A forms turbid plaques on wild-type strains but forms clear plaques on rnc⁻ mutants (Altuvia et al., 1987). Mutations in recO are more sensitive to UV than wild-type cells (Kolodner et al., 1985). To test for a recO⁻ phenotype, cells were streaked on an LB plate and irradiated with UV. Plates were wrapped in foil and grown for 24 hours at about 37° C. at which time they were checked for growth.

The plasmids pDLC142, pACS3, pACS3/BstXI, and pACS21 (all are pBR322 derivatives) contain various combinations of the rec, era, and recO genes. The pCE31 plasmid contains the era under the control of the pL promoter of λ (Chen et al., 1990). The pCE74 plasmid was constructed by subcloning the era1 mutation from pBP74 on a ClaI-BamHI fragment into pCE31. pACS74 was constructed by cloning the same ClaI-BamHI fragment from pBP74 into pACS3.

Characterization Of rnc And recO Phenotypes In era1 And rnc15

The rnc and recO phenotypes in era1 and rnc15 were determined. The bacteriophage λ normally forms turbid plaques on wild-type E. coli but forms clear plaques on strains that are rnc⁻ (Altuvia et al., 1987). Mutations in recO cause E. coli to be sensitive to UV light (Kolodner et al., 1985). Table 3 summarizes the results of the rnc and recO phenotypes in both strains. The rnc40 allele, which has been previously shown to have a polar effect on all three genes of the operon, was included as a control. When rnc15 is used as the indicator strain the phage λ plates with clear plaques, indicating a defect in the rnc gene. The rnc15 allele is also UV sensitive, demonstrating that recO is also defective. The era1 allele had no effect on either rnc or recO, demonstrating that era1 is the first mutation affecting era that doesn't affect the other two genes of the rnc operon. The fact that era1 has no effect on the other two genes of the operon shows that this mutation is a good candidate for the analysis of the in vivo function of era.

TABLE 3

Characterization of rnc and recO phenotypes in era1 and rnc15

| Allele | RnaseIII Phenotype | UV Sensitive | Growth at 25° C. |
|---|---|---|---|
| era+ | RNaseIII+ | No | Yes |
| era1 | RNaseIII+ | No | Slow |
| rnc15 | RNaseIII− | Yes | Slow |
| rnc40 | RnaseIII− | Yes | No |

Effect Of era1 On Growth Rate

The era1 mutation was linked to a Δtn10 marker TD1-17 that is located between the glyA gene and the rnc operon and shows 65% co-transduction with the rnc gene (Takiff et al., 1989). The linked era1 mutation was then transduced into the wild-type strain W3110 creating BSP750. Growth rates were determined for RABA17 and BSP750 (era1) at 42° C., 37° C., and 25° C. At all temperatures BSP750 (era1) grew slower than wild-type, demonstrating that era1 cells are defective for growth at all temperatures and are not cold-sensitive (FIG. 4).

GTPase Assays

Wild-type and mutant Era1 protein were purified essentially as previously described with one exception (Chen et al., 1990). Era precipitates in the 20%–30% ammonium sulphate fraction instead of the previously reported 13%–20% fraction.

GTPase assays were performed essentially as described (Chen et al., 1990). Reaction mixture (80 μl): 1.5 μg (40 pmol) of Era protein, 50 mM Tris-HCl, pH 8.0, 5 mM MgCl$_2$, 1 mM dithiothreitol, 0.1 M NaCl, 0.5 mg/ml bovine serum albumin, 10 mM GTP, 1 mM ATP, 0.1 mCi [α-$^{32}$P] GTP. Reactions were incubated at 37° C. for 60 minutes. Four ml of the reaction was spotted on PEI-cellulose and thin layer chromatography was performed in 0.5 M KH$_2$PO$_4$, 1 M NaCl at room temperature. Quantitation of GTP and GDP in GTPase assays was performed by exposing the TLC chromatogram to a Molecular Dynamics phosphoimager and quantitating the amount of GTP and GDP using ImageQuant software.

Effect Of Era1 On The GTPase Activity Of Era

In order to determine the effect of the Era1 (P17R) substitution on the GTPase activity of Era, the mutant protein was overexpressed and purified. The pCE31 plasmid is a previously described vector used for overexpressing Era (Chen et al., 1990). A ClaI-BamHI fragment containing the Era1 mutation from pBP74 (containing the nucleotides AGG for amino acid position 17) was cloned into pCE31 creating plasmid pCE74 (era 74). Protein from both plasmids was purified as previously described (Chen et al., 1990).

Figure 5:
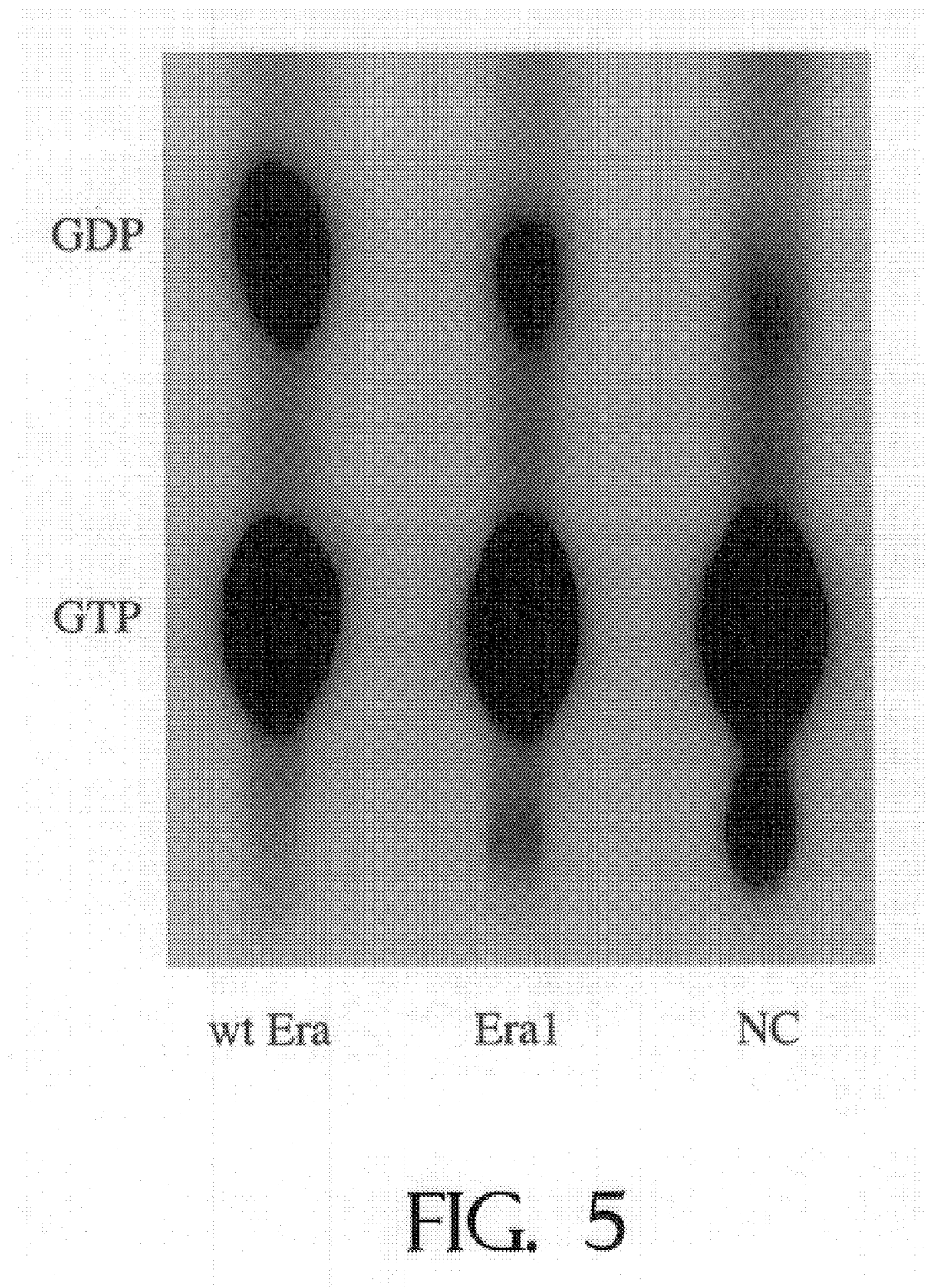
FIG. 5 shows GTPase activity of wild-type Era and Era1. No protein was added to the NC (negative control lane).

The ability of Era and Era1 proteins to convert [α-$^{32}$P] GTP to [α-$^{32}$P]GDP was determined and it was found that Era1 is defective in GTPase activity (FIG. 5). The amounts of GTP and GDP were quantitated using a phosphoimager and in three independent experiments Era1 was shown to have 4–5 fold less GTPase activity than the wild-type protein. Preliminary equilibrium dialysis assays performed on Era and Era1 suggest that they bind GTP and GDP similarly.

GTPases are believed to be molecular switches, with the GTP bound form thought of as being "on" and the GDP bound form as being "off" (Bourne et al., 1991). Oncogenic mutations in ras have been shown to be in the GTP bound form longer than normal, suggesting that the "on" form of the protein causes the activated state. FIG. 6 shows an alignment of the G1 domain of Era and human Ras. It was hypothesized that if era1, like many ras mutations, is an activating mutation, then overexpression of era1 in trans would not correct the defects of rnc15 and era1 mutations and may make the cells have a more severe phenotype. On the other hand, if the cell senses the GTPase activity of Era or the phosphorylated state of Era, then overexpressing era1 may be able to reverse suppression of dnaG2903 by era1 and rnc15 and/or complement the slow growth of era1 and rnc15.

Figure 7:
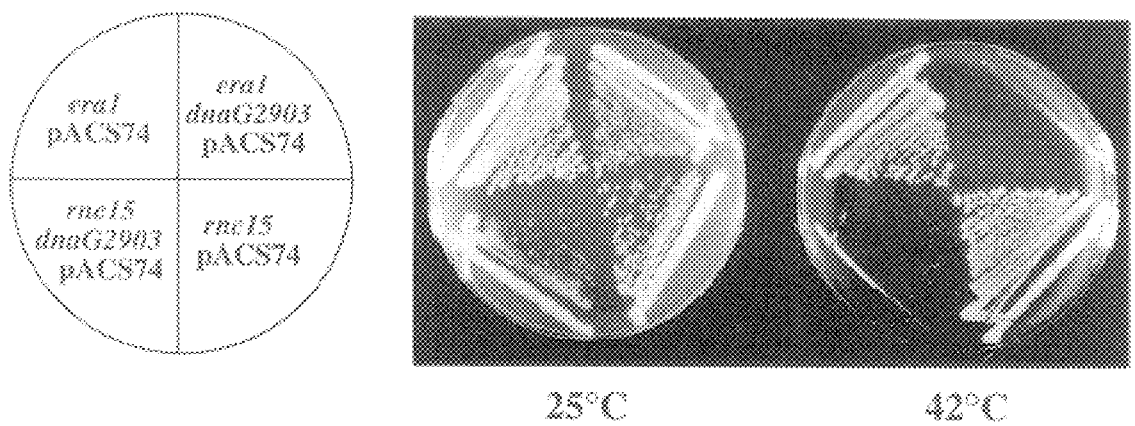
FIGS. 7A and B exhibits the effect of pACS74 on the growth of era1 and rnc15. pACS74 contains the era1 mutation cloned into pBR322. Compare the growth of these strains with those carrying the sdgE1 and sdgE15 mutations depicted in FIG. 1.

The era1 mutation was cloned into the plasmid pACS3 by replacing a ClaI-BamHI fragment of pACS3 with the ClaI-BamHI fragment from pBP74 that contains the era1 mutation in era. The resulting plasmid, pACS74, was transformed into four different strains: BSP750 (era1), BSP754 (era1, dnaG2903); BSP751 (rnc15); and BSP755 (rnc15, dnaG2903). The strains containing the plasmid were then tested for their ability to grow at different temperatures (FIG. 7). In BSP754 and BSP755, overexpression of era1 was able to reverse the suppression caused by the chromosomal era1 or rnc15 mutation. In addition, the slow growth was also complemented by overexpression of era1 in all four strains. The pACS74 plasmid was unable to suppress the temperature sensitivity of dnaG2903 or parB. These results suggest that era1 is not an activating mutation and that the cells may sense the total GTPase activity of Era or the phosphorylation state of Era in vivo.

Phenotypic Analysis Of The era1 Mutation By Combination Fluorescence-Phase Contrast Microscopy The protocol for the preparation of cells for microscopy is a modified version of previously published methods (Hiraga et al., 1989; Grompe et al., 1991). One ml of cells was centrifuged at 7000 rpm (4000G) to pellet the cells. The pellet was then washed with 1 ml of 0.84% NaCl and centrifuged again. The resulting pellet was resuspended in 100 ml of 0.84% NaCl. Ten ml of the cells were then spread on a slide and allowed to dry. A few drops of methanol was added to fix the cells to the slide. After five minutes the slides were dipped in tap water five times and then dried at room temperature. 10 μl of DAPI (5 μg/ml) was added just prior to addition of the cover slip. Cells were visualized at a magnification of 2000× with combination fluorescence-phase contrast illumination using a Zeiss Axioskop. Excitation of the DAPI dye was achieved by using a filter unit that allowed tramsmission of emitted light of wavelengths greater than 400 nm. Photographs were taken using Ektachrome 400 color slide film (Kodak).

Figure 8A:
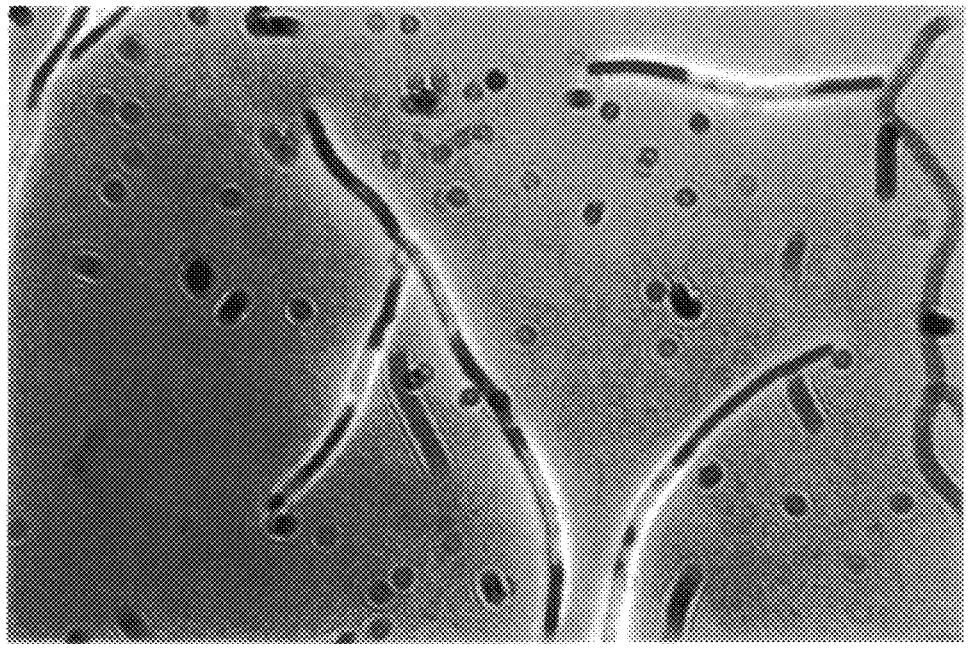
FIGS. 8A and B show fluorescence phase microscopy results.
Figure 8B:
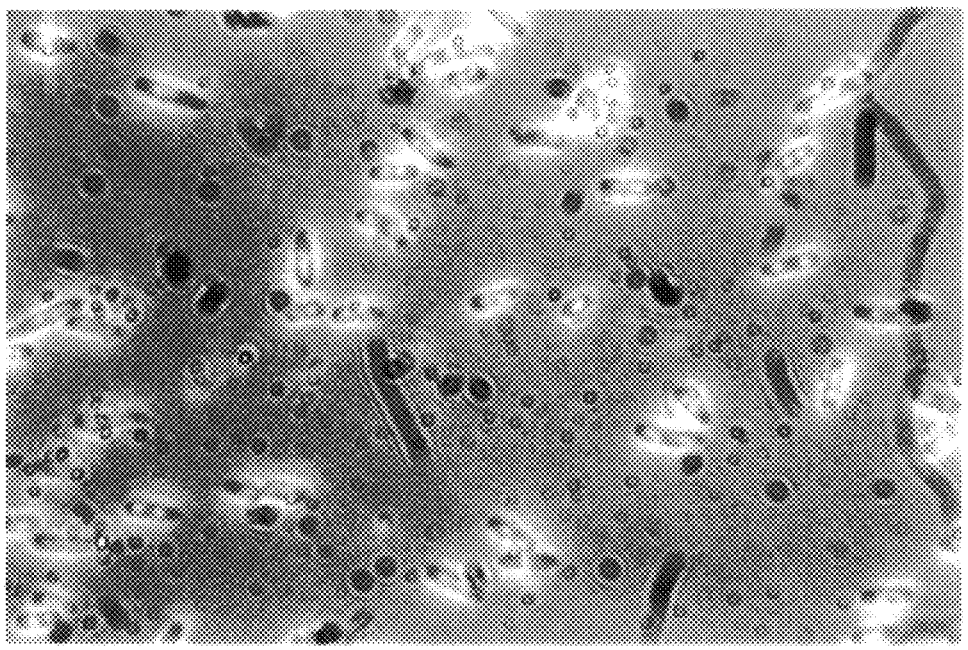

To determine the extent of suppression of dnaG2903 by era1, cells and nucleoids were visualized by combination fluorescence phase contrast microscopy. Strain KY2903 (dnaG2903), which is inviable at 42° C. forms long filaments with centrally located nucleoids at the non-permissive temperature (FIG. 8A). Analysis of strain BSP754 (dnaG2903, era1) demonstrates that era1, in addition to suppressing lethality at 42° C., also corrects the phenotypic defects (filamentation and abnormal chromosome partitioning) associated with the dnaG2903 mutation (FIG. 8B).

Figure 9A:
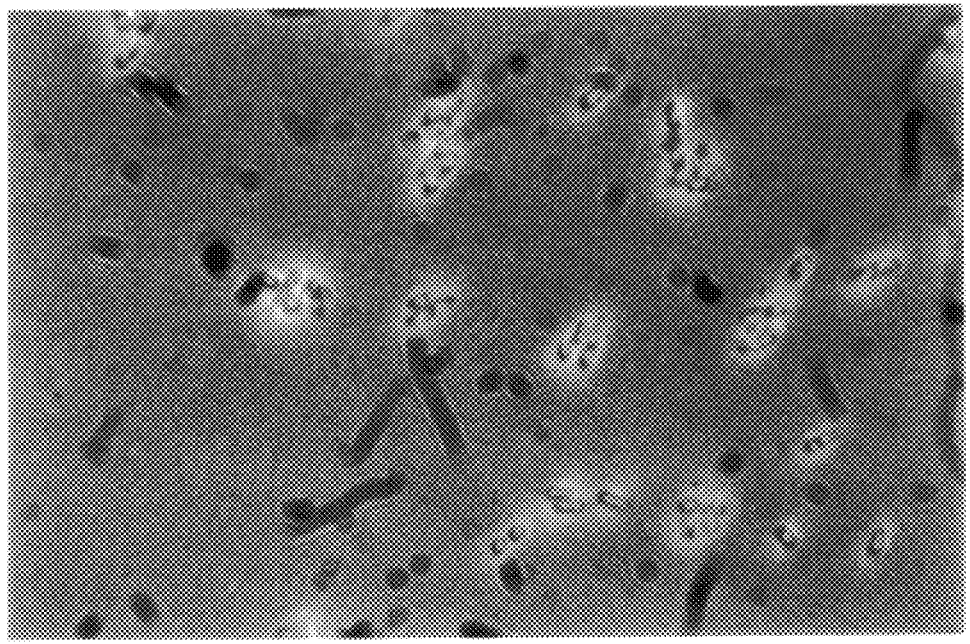
FIGS. 9A and B exhibits fluorescence phase microscopy results.
Figure 9B:
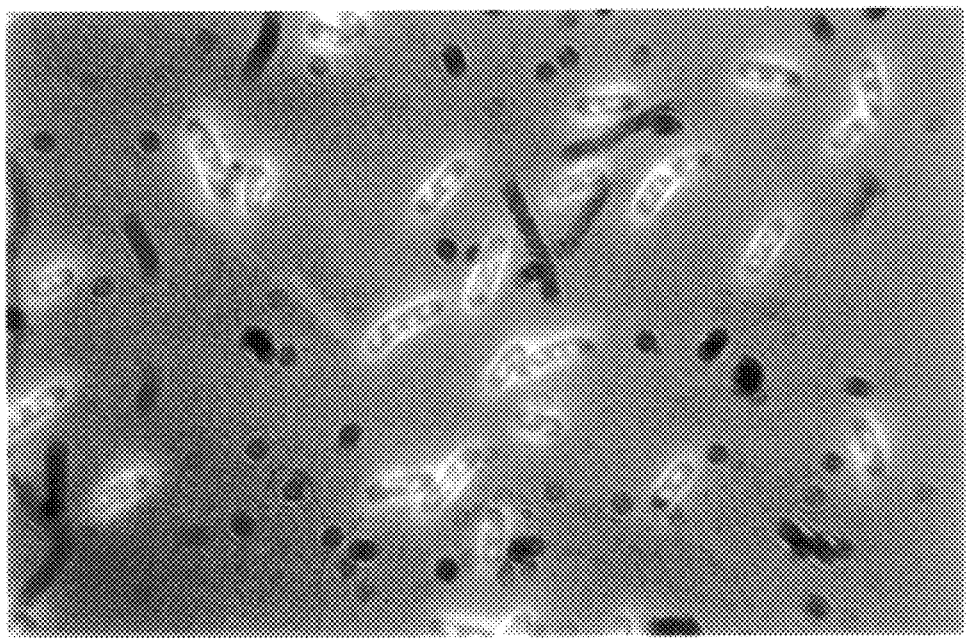

To determine if era1 has a cell shape and/or a nucleoid morphology phenotype in a wild-type background, W3110 and BSP750 (era1) were grown in LB broth at 25° C. and their phenotypes were visualized by fluo-phase microscopy. Wild-type strain W3110 consisted of cells containing either one or two nucleoids (FIG. 9A). The era1 mutant, although it had a 2.8 times longer doubling time than W3110, formed slightly longer cells of which 10% contained four segregated nucleoids (FIG. 9B). Based on previous studies of the E. coli cell cycle, wild-type cells theoretically should never contain more than two segregated nucleoids (Cooper and Helmstetter, 1968). These results suggest that era1 cells are defective in the cell cycle.

Suppression Of Multiple Cell Cycle Temperature-Sensitive Mutations By era1

The strains used in this study are listed in Table 4. Construction of specific strains with various alleles was performed by P1 transduction as described in Miller (Miller, 1972). Cells were grown in LB broth (10 g of tryptone, 10 g of NaCl, and 5 g of yeast extract) or on LB plates (LB broth+15 g of bactoagar) unless otherwise indicated. Kanamycin (30 μg/ml) and tetracycline (15 μg/ml) were added when necessary.

TABLE 4

Bacterial strains

| Strain | Relevant Genotype | Source |
| --- | --- | --- |
| W3100 | Prototroph | as Table 1 |
| KY2903 | W3100, dnaG2903 | as Table 1 |
| RAB10 | W3100, parB linked to Cm$^r$ | as Table 1 |
| BSP750 | W3110, era1 TD1-17::ΔTn10 | as Table 1 |
| BSP754 | W3110, dnaG2903, era1 TD1-17::ΔTn10 | as Table 1 |
| BSP755 | W3110, parB, era1 TD1-17::ΔTn10 | as Table 1 |
| BSP610 | JFL100, leuTN10; W3110, ftsZ84 | ftsz84 mobilized from JFL100tn10 leu by selection for Tetracycline resistance by P1 transduction selecting for Tn10 tetracycline resistance. Leutn 10 moved into JFL100 and the final strain made leu+ by P1 transduction and selection on minimal glucose plates for leucine prototrophy. |
| BSP832 | W3110, ftsZ84, era1 TD1-17:ΔTn10 | P1 transduction of BSP610 with BSP750 |
| BSP830 | W3110, ΔmukB::kan | Niki et al., 1991; Funnel & Cagnier, 1995. |
| BSP831 | W3110, ΔmukB::kan, era1 TD1-17::ΔTn10 | P1 transduction of BSP830 with BSP750 |
| FA22 | dnaB22 | E. coli Stock Center |
| RAB23 | dnaB22, era1 TD1-17::ΔTn10 | P1 transduction of FA22 with BSP750 |
| RAB203 | W3110, gyrB203 | N4177, E. coli Stock Center |
| RAB204 | W3110, gyrB203, ear1 TD1-17::ΔTn10 | P1 transduction of N4177 with BSP750 |
| E177 | W3110, dnaA177 | E. coli Stock Center |
| BSP844 | dnaA177, era1 TD1-17::ΔTn10 | P1 transduction of E177 with BSP750 |
| AX727 | dnaX2016 | E. coli Stock Center |
| RAB37 | dnaX2016, era1 TD1-17::ΔTn10 | P1 transduction of AX727 with BSP750 |
| AX621 | ftsA1882 | E. coli Stock Center |
| RAB621 | ftsA1882, era1 TD1-17::ΔTn10 | P1 transduction of AX621 with BSP750 |
| AX655 | ftsI2158 | E. coli Stock Center |
| JV47 | mg1655, parC281, TN10 | Versalovic 1994. Evolution of the macromolecular synthesis operon and analysis of bacterial primase. Ph.D. Thesis. Baylor College of Medicine, Houston, TX. |
| BSP854 | mg1655, parC281, TN10, era1, A17::ΔTN10:kan | Takiff et al., 1989 |
| RAB655 | ftsI2158, era1 TD1-17::ΔTn10 | P1 transduction of AX655 with BSP750 |
| HT120 | W3110, rnc40::ΔTn10 | set forth below |
| BSP848 | W3110, rnc40::ΔTn10 λRS74 (vector control) | set forth below |
| BSP849 | W3110, rnc40::ΔTn10 λRS473 (rnc') | set forth below |
| BSP850 | W3110, rnc40::ΔTn10 λRS463 (rnc+) | set forth below |
| BSP851 | W3110, rnc40::ΔTn10 λRS462 (rnc*) | set forth below |
| BSP853 | W3110, rnc40::ΔTn10 λRS559 (rnc+, era+) | set forth below |
| BSP853 | W3110, rnc40::ΔTn10 λRS560 (rnc*, era+) | set forth below |

BSP830 was prepared by P1 transduction of BSP750 (era1) with BF177 as the donor for mukB::kan allele. Kan$^R$ transductants were screened for temperature sensitivity and found to be resistant up to 39° C. Control constructs into W3110 produced transductants temperature sensitive above 32° C. All procedures were carried out at 30° C. or less. In addition, the BSP848 through 853 strains were constructed in the following manner. Strain HT120 was used to construct strains containing single copy λ prophages expressing the rnc and/or the era genes under control of the native rnc operon promoter. Tetracycline was used continuously throughout manipulations at the concentration of 12.5 μg/ml to insure adequate expression of era. The bacteriophage A constructs listed below were gifts from Dr. Robert Simons (UCLA) and introduced into HT120 using standard techniques (Miller, J., ed., 1992). Detection of strains that contained a single copy of the λ prophage was performed as described by Powell et al.,199. The following λ phages contain various combinations of wild-type and mutant rnc and era genes as follows:

λRS74=vector, imm21;
λRS473=λRS74 rncζ::lacZ
λRS463=λRS74 rnc, era'::lacZ
λRS462=λRS74 rnc*, era'::lacZ
λRS559=λRS74 rnc, era, recO'::lacZ
λRS560=λRS74 rnc*, era, recO'::lacZ ' is a nonfunctional insertion into λ caused by insertion of only a part of the gene; * is the insertion of entire gene into λ which is inactivated by a mutation.

The protocol for the preparation of cells for microscopy is a modified version of previously published methods (Hiraga et al., 1989; Grompe et al., 1991). One ml of cells was centrifuged at 7000 rpm to pellet the cells. The pellet was then washed with 1 ml of 0.84% NaCl and centrifuged again. The resulting pellet was resuspended in 100 μl of 0.84% NaCl. Ten μl of the cells were then spread on a slide and allowed to dry. A few drops of methanol were added to fix the cells to the slide. After five minutes the slides were dipped in tap water five times and then dried at room temperature. Ten μL of DAPI (5 μg/ml) was added just prior to addition of the cover slip. Cells were visualized at a magnification of 2000× with combination fluorescence-phase contrast illumination using a Zeiss Axioskop. Excitation of the DAPI dye was achieved by using a filter unit that allowed tramsmission of emitted light of wavelengths greater than 400 nm. Photographs were taken using Ektachrome 400 color slide film (Kodak).

The era1 mutation was isolated as a suppressor of dnaG2903 and has been shown to suppress a second dnaG allele, parB. Phenotypic analysis of a strain carrying the era1 mutation suggested that cells may be blocked just prior to cell division or delayed in the initiation of cell division. This observation raised the possibility that the suppression of the two dnaG alleles by era1 was indirect and might not be specific to dnaG. To test this possibility, several other temperature-sensitive mutations affecting various aspects of the cell cycle were analyzed for suppression by the era1 mutation.

Figure 10:
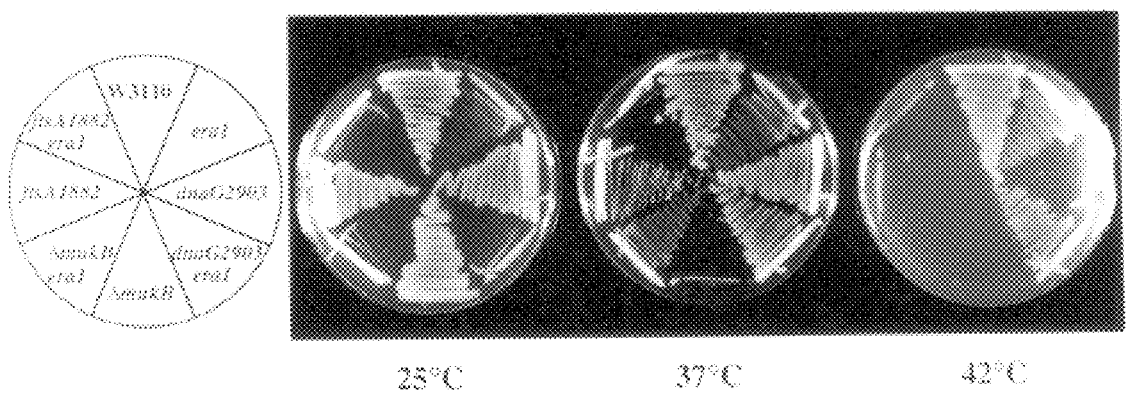
FIGS. 10A and B show suppression of multiple cell cycle alleles by era1.

The era1 allele was transduced by P1 into strains carrying temperature-sensitive mutations in genes involved in DNA replication, chromosome partitioning, chromosome segregation, and cell division. These strains were then tested for colony formation at 25° C., 37° C., and 42° C. FIG. 10 shows the results for three mutations tested. dnaG2903 is a temperature-sensitive allele that affects the primase protein and displays its temperature-sensitivity at 42° C. The era1 mutation restores the ability of dnaG2903 to grow at 42° C. The mukB gene was identified in a screen for genes that are involved in chromosome segregation. A null mutation in the mukB gene (ΔmukB) results in strains that can no longer form colonies at temperatures above 30° C. The era1 mutation suppresses the temperature-sensitivity of ΔmukB at 25° C. (compare ΔmukB and ΔmukB, era1 at 37° C.), but not at 42° C. A mutation affecting ftsA (ftsA1882), a gene involved in cell division, was not suppressed by era1 and in fact is actually more temperature-sensitive (compare ftsA1882 and ftsA1882, era1 at 37° C.)

Table 5 lists all of the mutations tested for suppression by era1. dnaB22, dnaG2903, parB, gyrB203, parC281, and ΔmukB were all suppressed by the era1 mutation. The mutations dnaA177, dnaX36, ftsZ84, ftsA1882, and ftsI2158 were not suppressed. In addition, ftsZ84 and ftsA1882 became more temperature-sensitive in the presence of the era1 allele. To be sure that strain background differences had no effect on the suppression by era1 isogenic strains were constructed. The dnaG2903, parB, ΔmukB, dna177, and ftsZ84 mutations were transduced by P1 into W3110 and again tested for suppression by era1. In all cases the strains behaved the same as in their original background. Thus era1 can suppress mutations affecting DNA replication, chromosome partitioning and segregation, but not mutations affecting cell division. This suggests that era1 acts at a point in the cell cycle after nucleoid segregation but prior to or during the cell division process.

TABLE 5

Summary of suppression of multiple cell cycle temperature-sensitive (Ts) alleles by era1.

| Ts Allele | Protein and Function of wild-type allele | Suppression by era1 | Growth at 37° C. | Growth on M63 media plus glucose at 42° C. |
|---|---|---|---|---|
| dnaG2903 | Primase. DNA replication initiation and elongation | Yes | Yes | NO |
| parB | Primase. DNA replication initiation and elongation | Yes | Yes | No |
| dnaA177 | DnaA. DNA replication initiation | No | Yes | No |
| dnaB22 | Helicase. DNA replication initiation and elongation | Yes | Yes | No |
| dnaX2016 | tau and γ subunits of DNA polymerase III | No | Yes | ND |
| gyrB203 | Subunited of DNA gyrase. DNA supercoiling | Yes | Yes | No |
| ΔmukB | MukB. Chromosome Segregation | Yes | No | No |
| ftsZ84 | FtsZ. Septum formation | No | Yes | Yes |
| ftsI2158 | PBP3. Septal wall synthesis | No | Yes | ND |
| ftsA1882 | FtsA. Unknown function in cell division | No | Yes | ND |
| parC281 | Topo.IV subunit. Decatenation of the chromosomes | Yes | No | ND |

ND = no data.

An alternative possibility for the difference in suppression of the temperature-sensitive alleles is that perhaps the mutations that were not suppressed have a more severe effect on E. coli cell growth than the ones that were suppressed. To test this hypothesis, strains were grown at 37° C. on LB plates to see if they were able to form colonies. The mutations that were not suppressed by era1 were all able to form colonies at 37° C., demonstrating that they are no more defective for colony formation than the alleles that were suppressed (Table 5).

Another possibility for the difference in suppression is that merely slowing down cell growth was responsible for suppression by era1 and that the fts mutations are unable to be suppressed by this mechanism. To test this possibility the strains were plated on M63 minimal media supplemented with glucose, which will slow down the growth of the cells. The temperature-sensitivity of ftsZ84 was suppressed by growth on minimal media. Because ftsZ84 was able to form colonies at 42° C. on minimal media it is unlikely that the mechanism of suppression by era1, as indicated by the absence of a complete correlation between the ability to suppress the temperature-sensitive alleles with era1 or by plating on minimal media, is merely due to a slow down of cell growth.

Analysis of Cells After Recovery From Chloramphenicol inhibition

Overnight cultures of W3110 and BSP750 (era1) were diluted 1:200 in LB broth and grown to an $A_{600}$ of 0.3 at 25° C. Chloramphenicol (150 mg/ml) was added to each culture to a final concentration of 300 μg/ml. Cells were incubated for 2 hours in the presence of chloramphenicol. Cultures were filtered through a 0.22 μM filter and washed twice with an equal volume of LB to remove the chloramphenicol. Cells were then resuspended in an equal volume of LB and grown at 25° C. Samples were taken to measure $A_{600}$ and for microscopy. Cells were prepared for microscopy as described above. Cultures were sampled for approximately one doubling time (W3110=105 minutes, BSP750 (era1)= 300 minutes) after the resumption of growth (initial increase in $A_{600}$). Photographs were taken and the number of nucleoids per cell were counted for each time point. A minimum of 120 cells was counted for each time point.

The data presented above and the observation that era1 cells contain four segregated nucleoids suggests that era acts after nucleoid segregation and prior to cell division. However, it is possible that era acts earlier in the cell cycle but the era1 phenotype is not observed until just prior to cell division. In an attempt to demonstrate where Era acts during the cell cycle, era1 cells were inhibited at a specific point in the cell cycle and their phenotypes were observed upon recovery from this inhibition.

When protein synthesis is inhibited in E. coli, cells arrest with a single nucleoid located in the center of the cell, demonstrating that nucleoid segregation requires post-replication protein synthesis (Donachie and Begg, 1989; Hiraga et al., 1990; van Helvoort and Woldringh, 1994). Ongoing rounds of DNA replication are completed and terminated in the absence of protein synthesis but new initiations do not occur. In addition to the completion of already initiated rounds of DNA replication, cells in the process of division do not require de novo protein synthesis. If era1 causes a delay at a stage in the cell cycle between nucleoid segregation and cell division, then it may be possible to see an accumulation of four nucleoid cells immediately after resumption of growth after protein synthesis inhibition. To test this hypothesis, W3110 and BSP750 (era1) were incubated with chloramphenicol (300 μg/ml) for two hours at 25° C. to block cells prior to nucleoid segregation. The chloramphenicol was then washed away and cells were allowed to resume growth. Both W3110 and BSP750 showed a 1.5–2 hour delay in the increase in $A_{600}$ during recovery at which time $A_{600}$ began to increase in both strains. A delay in the resumption of growth after chloramphenicol treatment has been previously reported (Hiraga et al., 1990). The fact that wild-type and era1 cells both began increasing $A_{600}$ at the same time suggests that era is not necessary for translation, unless Era negatively regulates this process.

Figure 11A:
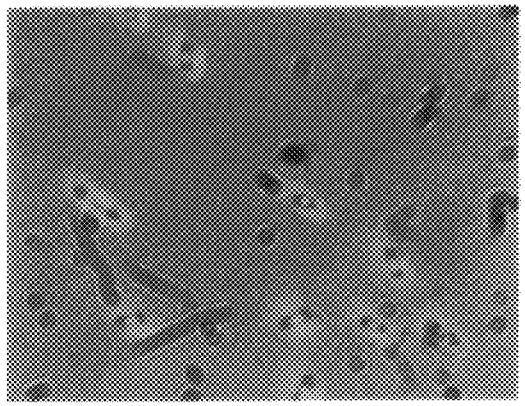
FIGS. 11A–D show phenotypic analysis of W3110 during recovery from inhibition of protein synthesis with chloramphenicol. Photographs were taken at different time points.
Figure 11B:
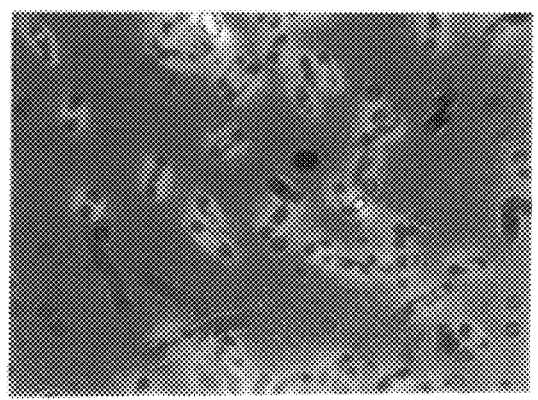
Figure 11C:
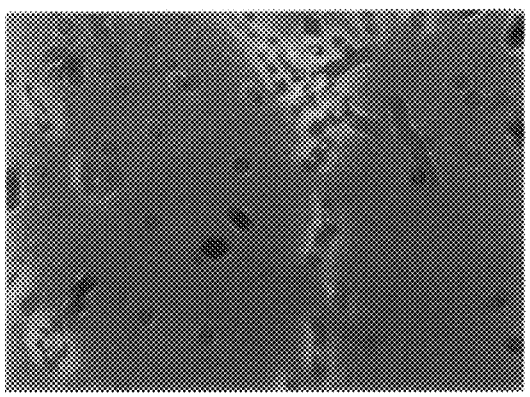
Figure 11D:
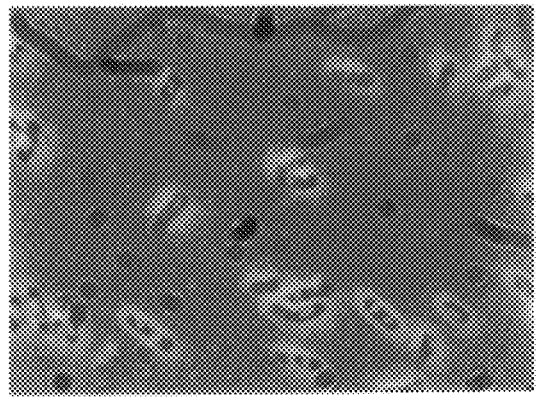
Figure 13A:
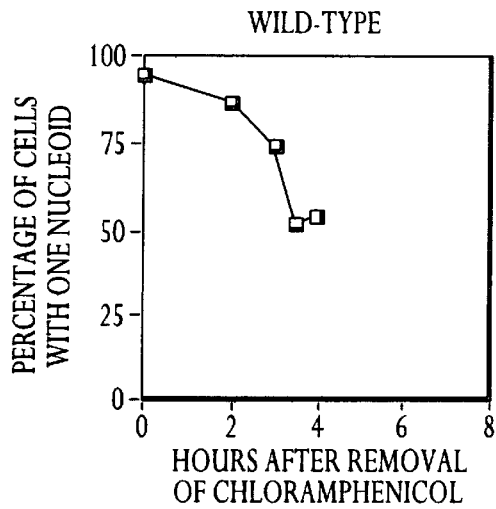
FIGS. 13A–F reveal the percentage of cells containing one, two, or four nucleoids in wild-type and era1 cells.
Figure 13B:
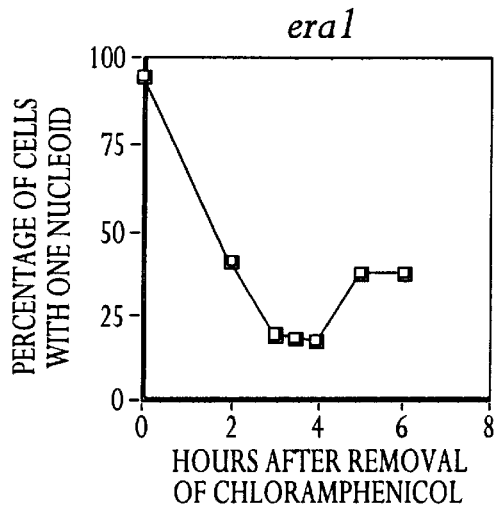
Figure 13C:
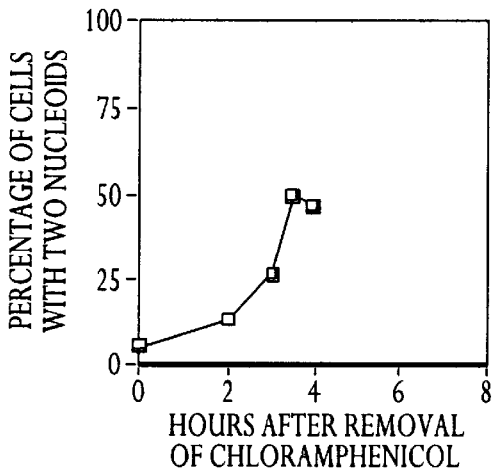
Figure 13D:
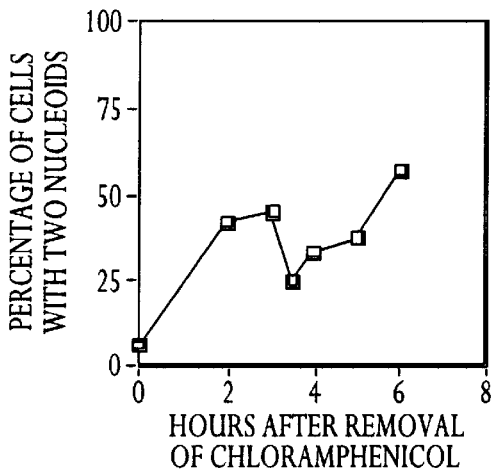
Figure 13E:
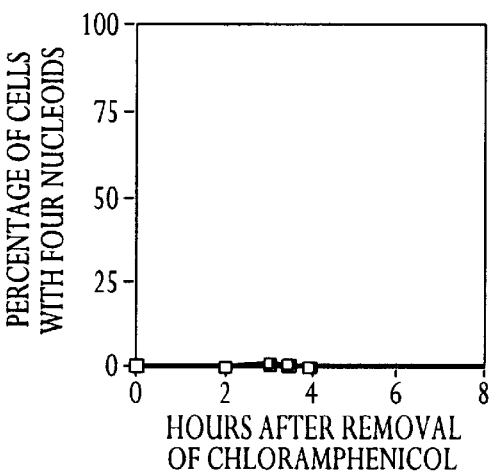
Figure 13F:
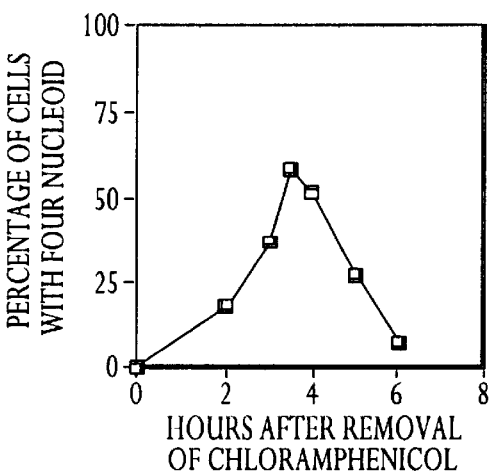

Samples of cells were taken from the cultures and prepared for microscopy as described above. FIGS. 11A–D shows the phenotypes of wild-type cells during recovery from chloramphenicol. After two hours of chloramphenicol inhibition, almost all of the cells contain a single centrally located nucleoid (FIG. 11A). Coinicident with the increase in $A_{600}$ at 1.5–2 hours after removal of chloramphenicol, cells with two nucleoids were observed indicating that the cells had begun to segregate their nucleoids (FIG. 11B). At three and four hours after recovery W3110 consisted of an approximately equal number of one and two nucleoid cells (FIGS. 11C and 11D). These results are consistent with previous reports investigating the segregation of nucleoids during recovery from chloramphenicol inhibition (Hiraga et al., 1990; van Helvoort and Woldringh, 1994).

The recovery of BSP750 (era1) cells following inhibition of protein synthesis is shown in FIGS. 12A–F. As observed in wild-type cells, nearly all of the era1 harboring cells contain a centrally located nucleoid following chloramphenicol treatment (FIG. 12A). However, the era1 cells are on average about 1.5 to about 2 times longer than wild-type cells (compare FIG. 11A with FIG. 12A). At 2 hours after recovery from chloramphenicol treatment cells with two nucleoids were observed but another type of cell was also found that was not present in wild-type cells, those containing four segregated nucleoids (FIG. 12B). These four nucleoid cells were found three, four, and five hours after recovery but were greatly decreased in numbers six hours after recovery (compare FIG. 12C, FIG. 12D, and FIG. 12E, with FIG. 12F).

The number of nucleoids in W3110 and BSP750 (era1) cells was counted at different timepoints after the recovery from chloramphenicol treatment and the results are shown in FIG. 13. In both wild-type and era1 cells 95% of the cells contained a single nucleoid (compare FIG. 13A and FIG. 13B) at 0 hours. The population of wild-type cells gradually accumulated two nucleoid cell types until four hours after recovery at which time there were approximately equal numbers of one and two nucleoid cells (FIG. 13A and FIG. 13C). In era1 cells, four nucleoid cells began to accumulate at two hours after inhibition and increased in number to almost 60% of the culture at 3.5 hours (FIG. 13F). Interestingly, the number of four nucleoid cells decreased from a maximum at 3.5 hours to 7% at 6 hours. Also, cell length decreased during this time period by 40%. These results indicate that the era1 mutation causes a block or a delay in the cell cycle. They also suggest that wild-type era function is required between nucleoid segregation and cell division.

Analysis Of The rnc40 Mutation With Various Combinations Of The rnc And era Genes Cells were grown in LB with tetracycline (15mg/ml) at 37° C. until an $A_{600}$ of 0.6–0.8 at which time they were washed with 10 volumes of LB to and diluted 1:20 in LB. Cells were grown at 25° C. and samples were taken and analyzed by fluorescence-phase contrast microscopy. Cells were prepared for microscopy as described above.

Phenotypic analysis has demonstrated that cells containing the era1 mutation have four segregated nucleoids. However, era1 is not lethal at any temperature and therefore the phenotype observed may be indicative of a partial defect in era. The rnc40 mutation, which is lethal at 25° C., was used to determine the phenotype of a conditional-lethal mutation affecting era.

Figure 14:
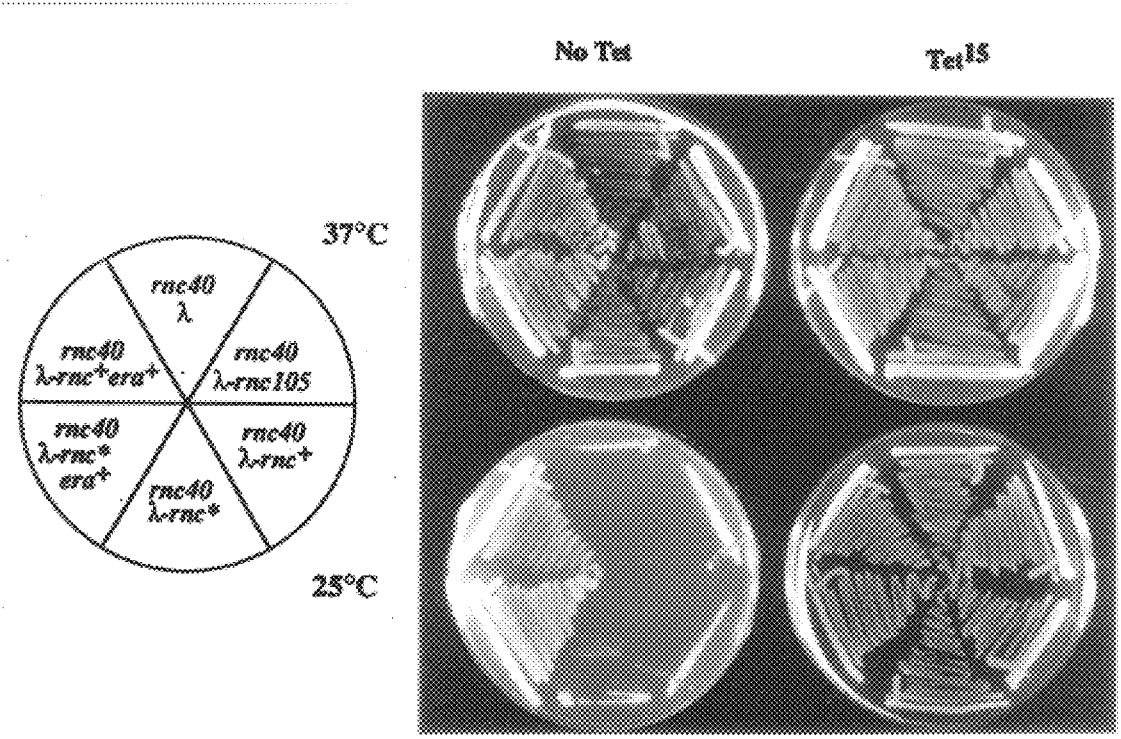
FIGS. 14A and B display growth of HT120 (rnc40) with various combinations of the rnc and era genes. Each strain depicted above contains the rnc40 mutation. Genes provided by the λ phage are indicated. rnc$^+$=wild-type rnc gene. era$^+$=wild-type era gene. rnc105 is a loss of function mutation in rnc. rnc*=40 bp BssH2 deletion filled in frame, inactivating the rnc gene.

Because the rnc40 mutation is polar on all of the downstream genes of the rnc operon, λ phage containing different combinations of the rnc and era genes were transduced into HT120 (rnc40). These strains were then tested for growth at 37° C. and 25° C. with and without tetracycline. FIG. 14 shows the results of this test. All strains grow well on tetracycline (15 μg/ml). When a strain harboring the rnc40 mutation as a chromosomal allele receives a recombinant λ phage containing no genes from the rnc operon or only the rnc gene, cells are unable to form colonies at 25° C. on LB plates (FIG. 14). When era is provided in trans on a recombinant λ phage, cells grow well at 25° C., whether or not rnc gene is present. This confirms earlier observations that the cold-sensitivity of rnc40 is due to the polar effect of the ΔTn10 insertion on the era gene.

Figure 15A:
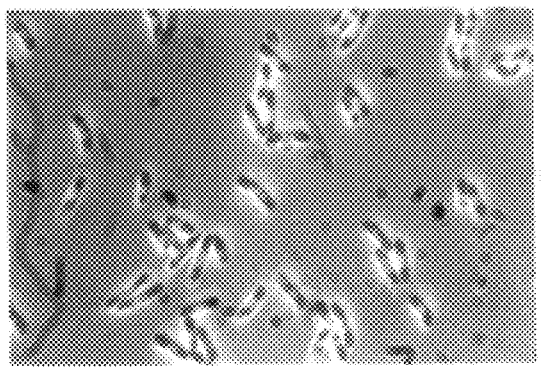
FIGS. 15A–D show phenotypic analysis of rnc40 containing strains with various combinations of the rnc and era genes.
Figure 15B:
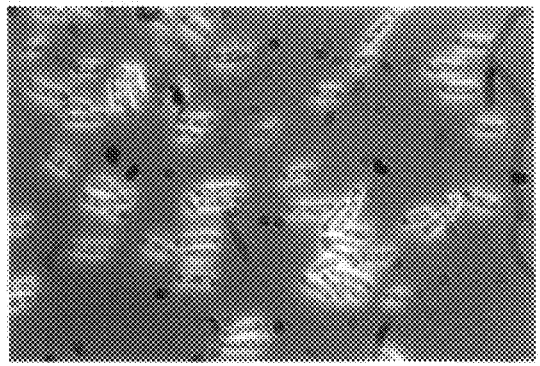
Figure 15C:
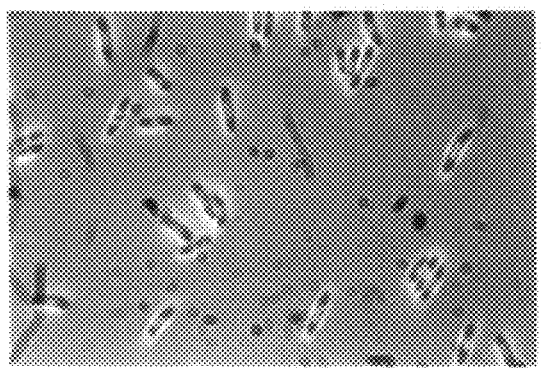
Figure 15D:
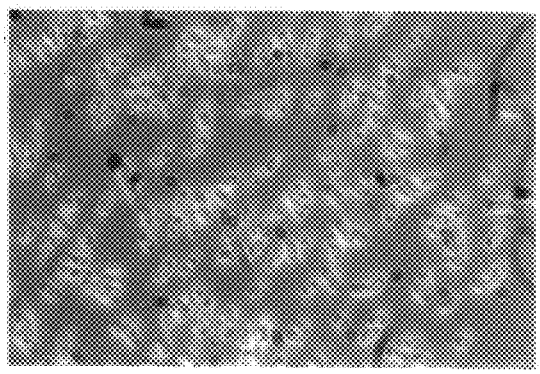
Figure 16:
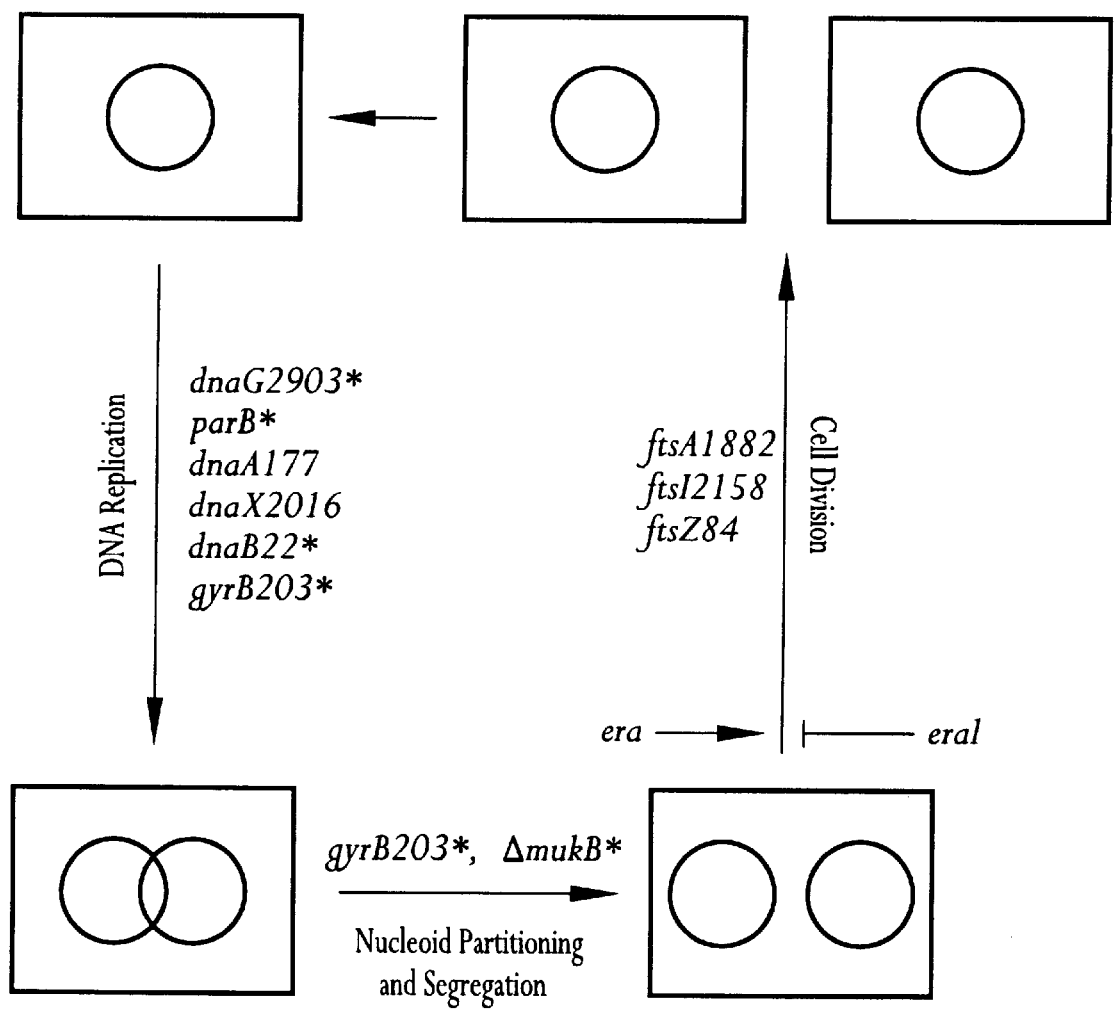
FIG. 16 is a summary of the cell cycle mutations tested for suppression by era1. Mutations are listed with the process they are known to affect. Where the era gene is thought to act during the cell cycle is shown. The block (or delay) in the cell cycle caused by era1 is also shown. *=mutation was suppressed by era1.

The cell morphology of these strains was analyzed by combination fluorescence-phase contrast microscopy. Cells were grown into exponential phase and then shifted to 25° C. for six hours at which time cells were prepared for microscopy. BSP848 (rnc40, λ vector control) formed cells with a single nucleoid present in the middle of the cell, much like when cells are inhibited with chloramphenicol (FIG. 15A). HT120 (rnc40) looks the same as BSP848, indicating that the presence of λ has no effect on the phenotype of the cells. Interestingly, strain BSP850 (rnc40, λ rnc+), forms four nucleoid cells at the non-permissive temperature (FIG. 15B). BSP851, which is the same as BSP850 except that the rnc gene contains an activated rnc gene, has the same phenotype as BSP848 (FIG. 15C). BSP853 (rnc40, λ rnc*, era+) which contains era as the only wild-type gene on λ, looked similar to wild-type cells (FIG. 15D). These results demonstrate that rnc40 is defective in chromosome partitioning at the non-permissive temperature and that this phenotype is due to a polar effect exerted on both rnc and era. In strains with a single copy of the rnc gene provided in trans to the polar rnc40 chromosomal allele on a λ phage, four nucleoid cells were observed at the non-permissive temperature, suggesting that this era lethal mutation has a similar effect on the cells as the era1 mutation.

Figure 17:
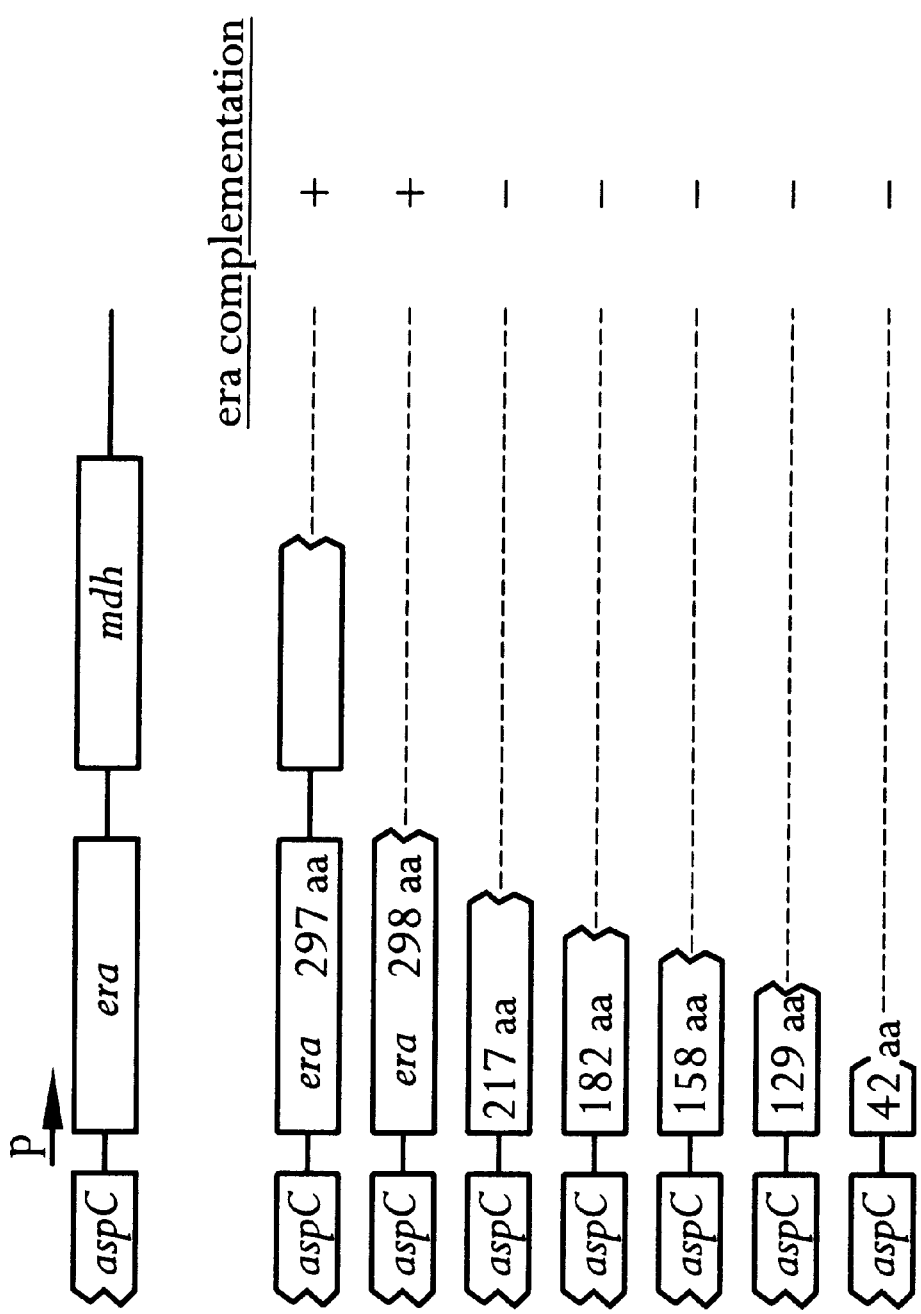
FIG. 17 reveals heterologous genetic complementation of the tet-dependent *E. coli* HT 120 defective for the expression of Era by the *F. tularensis* era contained on the plasmid pLVS120-1. The arrow indicates the direction of transcription from a potential promoter (P) located between aspC and era. Solid lines between aspC and era, and also between era and mdh represent the noncoding sequences between the ORFs. The extent of deletions are indicated by the broken lines.

Cloning Of The *F. tularensis* era era is the second gene in the polycistronic rnc operon of *E. coli* and is flanked upstream by rnc and down burnetii (Zuber et al, 1994), rnc and recO do not flank era in *F. tularensis* (FIG. 17). In fact, pLVS 120-1 failed to complement rnc *E. coli* in two different—[1] multicopy suppression of capsule synthesis (Zuber et al., 1994) and [2] activation λ N gene expression (Kameyama et al, 1991). Also, the location and organization of the *F. tularensis* era are remarkably different from those of the gram-positive *Streptococcus mutans*, where era is located downstream but in the same operon as the gene encoding diacyl glycerol kinase, dgk (Wu et al., 1995; Yamashita et al., 1993). Upstream to the *F. tularensis* era open reading frame (ORF), a truncated ORF encoding a protein with significant homology to aspartate aminotransferase, aspC, of Bacillus sp. (GenBank Accession No. M59430) was found. There is an intercistronic region of 114 bp between the aspC and era ORFs, containing potential promoter-like sequence. Also, immediately downstream to era, a 200 bp of noncoding sequence followed by a truncated ORF encoding a protein with homologies to malate dehydrogenase (mdh) of *Bacillus israeli* (GenBank Accession No. X90527) was found. Thus, the era of *F. tularensis* is organized, with respect to flanking genes, in a unique manner from other bacterial era genes (Table 6). Interestingly, the *F. tularensis* genes coding for the components of the DnaK molecular chaperone system are organized in a fashion that is characteristic of some gram-positive bacteria (Zuber et al, 1995).

TABLE 6

Relative location of era in various microorganisms
Function or Gene

| Organism | Upstream of era | Downstream of era |
|---|---|---|
| E. coli | RnaseIII (rnc) | RecO (recO) |
| C. burnetii | RnaseIII (rnc) | RecO (recO) |
| H. influenzae | RnaseIII (rnc) | RecO (recO) |
| S. typhimurium | RnaseIII (rnc) | RecO (recO) |
| F. tularensis | Aspartate amino-transferase (aspC) | Malate dehydrogenase (Mdh) |
| B. subtilis | Cytidine deaminase | RecO |
| S. mutans | Diacyl glycerol-kinase (dgk) | No sequence available |
| M. leprae | Hypothetical ORF | RecO (recO) but spaced 1500-bp downstream of era |
| Synechocystis sp. | Sigma factor | Histidine kinase (cheA) |
| N. genitalium | Hypothetical ORF | Cytadherence accessory protein (hmwl) |

To define the precise location and functional activity of era on the 4-kb DNA insert of pLVS120-1 and to facilitate nucleotide sequencing, unidirectional deletions were generated in vitro using Promega's Erase-a-Base system (Promega, Madison, Wis., USA). Clearly, deletions extending into the era ORF result in the loss of tetracycline-independent growth in HT120 (FIG. 17). The era complementation activity mediated by pLVS120-1 (FIG. 17) appears to be a direct result of its expression from the promoter-like sequence located between the aspC and era ORFs. The 1 ac promoter of the vector is oriented in the antisense direction for era. The deduced amino acid sequence of the *F. tularensis* era is highly similar to the Era proteins of *B. subtilis, C. burnetii, E. coli, Haemophilus influenzae, Mycobacterium leprae, Mycoplasma genitalium, S. mutans* and Synechocystis sp. (Table 7). Interestingly, the *F. tularensis* Era shares a higher percent identity with the Era proteins of the gram-negative *E. coli* and *H. influenzae*, and also the gram-variable *C. burnetii* relative to the Era proteins of the gram-positive *S. mutans* and *B. subtilis*. The Era of the more distantly related eubacterial Synechocystis sp. is also well conserved (Table 7; FIG. 18). Because *F. tularensis* era complements *E. coli* defective for the expression of Era, era may also be an essential gene in *F. tularensis*. The era genes of the gram-positive *S. mutans* (Pillutla et al., 1995) and gram-variable *C. burnetii* (Zuber et al., 1994) have also been shown to complement for Era function in *E. coli*, thus suggesting the Era probably responds to the same signal(s) in these bacteria despite their phylogenetic diversity.

TABLE 7

Relatedness of Era proteins to *F. tularensis*

| | | *F. tularensis* Era | |
|---|---|---|---|
| | Accession | | |
| era of | Number | Identity (%) | Similarity (%) |
| E. coli | P06616 | 49.8 | 70.2 |
| C. burnetii | L27436 | 50.3 | 68.7 |
| H. influenzae | P43728 | 52.2 | 70.9 |
| S. mutans | P37214 | 42.6 | 66.0 |
| B. subtilis | P42182 | 43.4 | 65.5 |
| M. leprae | U00016 | 34.5 | 57.9 |
| Synechocystis sp. | D63999 | 36.6 | 61.3 |
| M. genitalium | D43967 | 23.7 | 49.8 |

Computer Analysis Of Bacterial Era Protein Sequences

Results of the computer analysis of all the available bacterial Era protein sequences are presented in FIG. 18. From this analysis, four conserved domains have been identified in addition to the known GTP-binding domains G-1, G-3, and G-4 (Bourne et al, 1991). In fact, results suggest that the consensus sequence for G-1 (GRPNVGKS, SEQ ID NO: 17) and G-3 (DTPGL, SEQ ID NO: 18) domains (Bourne et al., 1991) can be extended by four and one aa, respectively (FIG. 18). A point mutation in *E. coli* era resulting in a change at aa position 21 from K (lysine) to R (arginine) located in G-1 domain (FIG. 18) has been shown to cause loss of complementation activity for bacterial growth (Pillutla et al, 1995). Interestingly, this K21 residue is conserved in all nine Era proteins (FIG. 18). Sood et al. (1994) have identified a tryptic peptide (ISITSR, SEQ ID NO: 19) in *E. coli* era from residues 33 to 38 as a site for autophosphorylation. Point mutations resulting in changes at amino acid positions S34P and 135F have been reported to cause a loss of Era complementation activity (Pillutla et al., 1995). Results presented in FIG. 18 (see box A) suggest a consensus sequence of IXITSXKXQTTR, SEQ ID NO: 20 for this autophosphorylation site. Changes in amino acid residues at P21 IT or S213P of *E. coli* Era also cause a loss of functional complementation (Pillutla, 1995). In fact, these residues also comprise a consensus sequence (EXPHSXAXV, SEQ ID NO: 21) indicated as box B (FIG. 18). Of the two alleles mutated in box B, only P211 is present in all nine Era protein sequences available. Another consensus sequence (SQKGIVIGKKG, SEQ ID NO: 22) representing box C in FIG. 18 is yet to be mutagenized to determine it importance. A fourth consensus sequence (LWVKVK, SEQ ID NO: 23) is represented by box D in FIG. 18. Amino acid changes at W278A or K280A of *E. coli* Era, however, retain complementation activity for bacterial growth (Pillutla et al., 1995). The consensus sequence domains identified in this study (boxes A, B, C, and D of FIG. 2) might prove to be useful to define functionally important regions outside the nucleotide-binding domains. A carboxyl-terminal deletion of 80 amino acid from the *F. tularensis* Era (FIG. 17) that includes box C and box D domains (FIG. 18) resulted in a loss of functional complementation of *E. coli*.

Identification of the human ERA homolog of the *Escherichia coli* era gene.

To identify a human homolog of the *Escherichia coli* era gene, the carboxy terminal portion of the Era protein was used to search for similar sequences in the Expressed Sequence Tag (EST) database using Baylor College of Medicine search launcher program and the tblastx dbest database. tblastx provides a six frame translation of ESTs of the dbest database. The COOH terminus of Era from *E. coli* was used such that any ESTs that contain a GTP-binding domain (found in the amino terminus of Era) would not be found, so that Era specific sequences would be identified. The EST R57504 (GenBank ID number) was identified as having sequences that when translated were similar to the carboxy terminus of the *E. coli* Era protein. The DNA sequence from R57504 was used to search the blastn dbest database for any sequences that were partially identical and thus overlapped with R57504. Blastn provides DNA sequences of the dbest database. This search and subsequent searches identified the following ESTs (identified below by GenBank ID number) that comprise part of the human ERA sequence: R21701, D79048, R19122, H10444, H10445, T87374, H53502, H64871, T79830, N46232, H65468, F19739, H53872, T32992, F02922, F02187, F04605, T34378, N57957, Z43596, F07179, F05941, H11840, F08384, and W98375. The EST H10444 (clone ID#47088), containing a 1.7 kb human genomic DNA insert, was purchased from Genome Systems (St. Louis, Mo.) and the DNA sequence of the insert was determined. A contig of the sequence generated from H10444, along with sequence published in the EST database from clones R21701, D79048, and R57504 identified a 1317 bp sequence that encodes for a protein of 438 amino acids (FIG. 19 and FIG. 20).

An alignment of the carboxy terminal 331 amino acids of human ERA and the full *E. coli* Era protein demonstrated significant identity and similarity between the two proteins. The human ERA protein shows identity with *E. coli* Era in all regions that have been determined to be conserved in bacterial Era proteins. An additional region of homology is also observed. Overall identity between the two proteins is 30% (having the same amino acid at a particular position) and they are 53% similar (having functionally similar amino acids at a particular position).

A 1.1 kb fragment (5') of the EST H10444, containing the human ERA sequence, was hybridized to a somatic cell hybrid panel PstI (Oncor, Inc., Gaithersburg, Md.) and was found to specifically hybridize to human chromosome 17. This 1.1 kb fragment of H10444 was then used to probe a human chromosome cosmid library to identify cosmids with which Fluorescence In Situ Hybridization (FISH) was performed. Cosmids identified as having sequence from H10444 were 36d4, 150g3, 38d3, and 78f3. FISH analysis of the cosmids demonstrated that the Human ERA gene maps to the chromosome 17q 1.2-12 region. Subsequent mapping of the mouse ERA gene using the EST H10444 to the syntenic region of chromosome 11 confirmed the mapping data. Northern analysis using a Clonetech human multiple tissue northern (MTN) blot showed that human ERA is expressed in all tissues, most highly in the heart and skeletal muscle.

The disclosures of each patent, patent application and publication cited or described in this document are hereby incorporated herein by reference, in their entirety.

Various modifications of the invention in addition to those shown and described herein will be apparent to those skilled in the art from the foregoing description. Such modifications are also intended to fall within the scope of the appended claims.

REFERENCES

U.S. Pat. No. 4,683,195
U.S. Pat. No. 4,683,202
U.S. Pat. No. 4,800,159
EPA No. 320,308
EPA Publication No. 329,822
GB Application No. 2 202 328
PCT Application No. PCT/US89/01025
PCT Application No. PCT/US87/00880
PCT Application WO 88/10315
PCT Application WO 89/06700
Ahnn, J., P. E. March, H. E. Takiff and M. Inouye (1986). A GTP-binding protein of *Escherichia coli* has homology to yeast RAS proteins. Proceedings of the National Academy of Sciences USA 83: 8849–8853.
Altuvia, S., H. Locker-Giladi, S. Koby, 0. Ben-Nun and A. B. Oppenheim (1987). RNaseIII stimulates the translation of the cII gene of bacteriophage 1. Proceedings of the National Academy of Sciences USA 84: 6511–6515.
Bardwell, J. C. A., P. Regnier, S. Chen, Y. Nakamura, M. Grunberg-Manago and D. L. Court (1989). Autoregulation of RNase III operon by mRNA processing. EMBO Journal 8: 3401–3407.
Bourne, H. R., D. A. Sanders and F. McCormick (1991). The GTPase superfamily: conserved structure and molecular mechanism. Nature 349: 117–127.
Bram, R. J., R. A. Young and J. A. Steitz (1980). The ribonuclease III site flanking 23S sequences in the 30S ribosomal precursor RNA of *E. coli*. Cell 19: 393–401.
Bramhill, D. and C. M. Thompson (1994). GTP-dependent polymerization of *Escherichia coli* FtsZ protein to form tubules. Proceedings of the National Academy of Sciences USA 91: 5813–5817.
Chen, S. -M., H. E. Takiff, A. M. Barber, G. C. Dubois, J. C. A. Bardwell and D. L. Court (1990). Expression and characterization of RNaseIII and Era proteins. Journal of Biological Chemistry 265: 2888–2895.
Cooper, S. and C. E. Helmstetter (1968). Chromosome replication and the division cycle of *Escherichia coli* B/R. Journal of Molecular Biology 31: 519–540.
De Boer, P., R. Crossley and L. Rothfield (1992). The essential bacterial cell-division protein FtsZ is a GTPase. Nature 359: 254–256.
Donachie, W. D. and K. J. Begg (1989). Chromosome partition in *Escherichia coli* requires post-replication protein synthesis. Journal of Bacteriology 171: 5405–5409.
Erickson, H. P. (1995). FtsZ, a prokaryotic homolog of tubulin? Cell 80: 367–370.
Finkel, T., C. J. Der and G. M. Cooper (1984). Activation of ras genes in human tumors does not affect localization, modification, or nucleotide binding of p21. Cell 37: 151–158.
Frohman, M. A., In: *PCR Protocols: A Guide to Methods and Applications* 1990, Academic Press, N.Y.
Funnel and Cagnier, 1995, "Partition of T1 Plasmids in *E. coli* mukB Chromosomal Partition Mutants", 177(9) :2381–2386.
Gegenheimer, P. and D. Apirion (1981). Processing of procaryotic ribonucleic acid. Microbiological Reviews 45: 502–541.
Gollop, N. and P. March (1991 a). Localization of the membrane binding sites of Era in *Escherichia coli*. Research in Microbiology 142: 301–307.
Gollop, N. and P. E. March (1991b). A GTP-binding protein (Era) has an essential role in growth rate and cell cycle control in *Escherichia coli*. Journal of Bacteriology 173: 2265–2270.

Grompe, M., J. Versalovic, T. Koeuth and J. R. Lupski (1991). Mutations in the dnaG Gene of *Escherichia coli* suggest coupling between DNA replication and chromosome partitioning. Journal of Bacteriology 173: 1268–1278.

Hiraga, S., H. Niki, T. Ogura, C. Ichinose, H. Mori, B. Ezaki and A. Jaffe (1989). Chromosome partitioning in *Escherichia coli*: novel mutants producing anucleate cells. Journal of Bacteriology 171: 1496–1505.

Hiraga, S., T. Ogura, C. Ichinose and H. Mori (1990). Positioning of replicated chromosomes in *Escherichia coli*. Journal of Bacteriology 172: 31–39.

Innis et al., *PCR Protocols*, Academic Press, Inc., San Diego Calif., 1990.

Kameyama, L., et al., RnaseIII activation of bacteriophage λ N synthesis, Mole. Microbiol., 5 (1991) 2953–2963.

King, T. C., R. Sirdeshmukh and D. Schlessinger (1986). Nucleolytic processing of ribonucleic acid transcripts in procaryotes. Microbiological Reviews 50: 428–451.

Kok, J., K. A. Trach and J. A. Hoch (1994). Effects on *Bacillus subtilus* of a conditional lethal mutation in the essential GTP-binding protein Obg. Journal of Bacteriology 176: 7155–7160.

Kolodner, R., R. A. Fishel and M. Howard (1985). Genetic recombination of plasmid DNA: effect of RecF pathway mutations on plasmid recombination in *Escherichia coli*. Journal of Bacteriology 163: 1060–1066.

Kornberg, A. and T. A. Baker (1992). DNA Replication, Second Edition. New York, W. H. Freeman and Company.

Krengel, U., Schlichting I, A. Scherer, R. Schumann, M. Frech, J. John, W. Kabsch, E. Pai and A. Wittinghofer (1990). Three-dimensional Structures of H-ras p21 mutants: molecular basis for their inability to function as signal switch molecules. Cell 62: 539–548.

Kwoh D., et al., *Proc. Natl. Acad. Sci.* (*U.S.A.*) 1989, 86:1173.

Lerner, C. G. and M. Inouye (1991). Pleiotropic changes resulting from depletion of Era, an essential GTP-binding protein in *Escherichia coli*. Molecular Microbiology 5: 951–957.

Lerner, C. G., P. Sood, J. Ahnn and M. Inouye (1992). Cold-sensitive growth and decreased GTP-hydrolytic activity from substitution of Pro 17 for Val in Era, an essential *Escherichia coli* GTPase. FEMS Microbiology Letters 95: 137–142.

Lin, Y. P., J. D. Sharer and P. E. March (1994). GTPase-dependent signaling in bacteria: characterization of a membrane-binding site for era in *Escherichia coli*. Journal of Bacteriology 176: 44–49.

Marshall, C. (1985). Human oncogenes. In R. Weiss, N. Teich, H. Varmus and J. Coffin RNA tumor viruses. 487–658. Cold Spring Harbor N.Y, Cold Spring Harbor Laboratory.

Methods in Enzymology, 1995, 255:95–107.

Methods in Enzymology, 1995, 255:110–125.

Miller, J. H. (1972). Experiments in molecular genetics. Cold Spring Harbor, N.Y, Cold Spring Harbor Laboratory.

Miller, J., ed., 1992, A Short Course in Bacterial Genetics: A Laboratory Manual and Handbook for *Escherichia coli* and Related Bacteria, Cold Spring harbor laboratory Press, Cold Spring Harbor, N.Y.

Moore and Lohman 1994, "Kinetic Mechanism of Adenine nucleotide Binding to and Hydrolysis by the *Escherichia coli* Rep Monomer. 1. Use of Fluorescent Nucleotide Analogs", Biochemistry, 33:14550–14564

Morrison, P. T., et al., Molecular Analysis of the *Escherichia coli* rec0 gene, J. Bacteriol., 171 (1989) 3641–3649.

Mukherjee, A. and J. Lutkenhaus (1994) Guanine nucleotide-dependent assembly of FtsZ into filaments. Journal of Bacteriology 176: 2754–2758.

Murakami, Y., et al., (1985) Novel dnaG Mutation in a dnaP mutant of *Escherichia coli*", J. Bact., 162:830–832.

Niki et al., EMBO, 1991, 10(1):183–193.

Ohara, O., et al., *Proc. Natl. Acad. Sci.* (*U.S.A.*) 1989, 86:5673–5677).

Patterson, T. A., et al., 1993, Improved Bacterial Hosts for Regulated Expression from LambdapL Plasmid Vectors. Gene, 132:83–87.

Powell, et al., Nucleic Acids Research, 1994, 22(25) :5765–5766.

Pillutla, R. C., et al., Cross-species complementation of the indispensable *Escherichia coli* era gene highlights amino acid regions essential for activity, J. Bacteriol., 177 (1995) 2194–2196.

RayChaudhuri, D. and J. T. Park (1992). *Escherichia coli* cell-division gene encodes a novel GTP-binding protein. Nature 359: 251–254.

Sambrook, et al., *Molecular Cloning. A Laboratory Manual,* 2nd ed., Cold Spring Harbor Laboratory Press, Cold Spring Harbor, N.Y. (1989).

Sanger et al. *Proc. Nat'l. Acad. Sci, U.S.A.,* 1977, 74, 5463.

Seeburg, P. H., W. W. Colby, D. J. Capon, D. V. Goeddel and A. D. Levinson (1984). Biological properties of human c-Ha-ras1 genes mutated at codon 12. Nature 312: 71–75.

Sood, P., C. G. Lerner, T. Shimamoto, Q. Lu and M. Inouye (1994). Characterization of the autophosphorylation of Era, an essential GTPase in *Escherichia coli*. Molecular Microbiology 12: 201–208.

Takiff, H., S. -M. Chen and D. L. Court (1989). Genetic analysis of the rnc operon of *Escherichia coli*. Journal of Bacteriology 171: 2581–2590.

Takiff, et al., Locating essential *Escherichia coli* genes by using mini-Tn10 transposons: the pdxJ operon, J. Bacteriol., 174(1992) 1544–1553.

van Helvoort, J. M. L. M. and C. L. Woldringh (1994). Nucleoid partitioning in *Escherichia coli* during steady-state growth and upon recovery from chloramphenicol treatment. Molecular Microbology 13: 577–583.

Versalovic 1994. Evolution of the macromolecular synthesis operon and analysis of bacterial primase. Ph.D. Thesis. Baylor College of Medicine, Houston, Tex.

Vidwans, S. J., K. Ireton and A. D. Grossman (1995). Possible role for the essential GTP-binding protein Obg in regulating the initiation of sporulation in *Bacillus subtilus*. Journal of Bacteriology 177: 3308–3311.

Walker, G. T., et al., *Proc. Natl. Acad, Sci.* (*U.S.A.*) 1992, 89:392–396

Weinstock, G. (1987). General recombination in *Escherichia coli*. p. 1034–1043. In F. C. Neidhardt (ed.) *Escherichia coli* and *Salmonella typhimurium*. Cellular and Molecular Biology. Washington D.C., American Society for Microbiology.

Welch et al., 1994, "Biochemical Characterization of the Essential GTP-binding protein Obg of *Bacillus subtilis*", J. Bacteriol., 176(23):7161–7168.

Wu, D. Y., et al., *Genomics* 1989, 4:560.

Wu, J., et al., Expression, purification, and characterization of a novel G protein, SGP, from *Streptococcus mutans*, Infect. Immun. 63 (1995) 2516–2521.

Yamashita, Y., et al., Molecular characterization of a *Streptococcus mutans* mutant altered in environmental stress responses, J. Bacteriol., 175 (1993) 6220–6228.

Zuber et al., Analysis of the rnc locus of *Coxiella burnetii*, Mol. Microbiol. 14 (1994) 291–300.

What is claimed is:

1. A method of screening for an agent that delays a cell cycle comprising:
   (a) providing purified Era protein moiety;
   (b) preparing at least one agent suspected of inhibiting Era protein moiety;
   (c) combining said purified Era protein moiety and said agent with GTP to form a Era protein moiety-agent-GTP combination;
   (d) measuring GDP resulting from said Era protein moiety-agent-GTP combination; and
   (e) comparing GDP of step (d) with GDP resulting from a control, wherein GDP resulting from step (d) is reduced compared to GDP resulting from said control thereby identifying an agent that delays a cell cycle.

2. The method of claim 1 wherein said at least one agent comprises a mixture of agents.

3. The method of claim 1 wherein said at least one agent comprises a mixture of agents and following step (e), said method is repeated for each individual agent of said mixture.

4. The method of claim 1 wherein said GDP is labeled with a label selected from the group consisting of $^{32}$P, biotin, and fluorescein.

5. The method of claim 1 wherein GDP is measured by a method selected from spectrophotometry, densitometry, and chromatography.

6. The method of claim 1 wherein the cell of said cell cycle is a bacterial cell and said Era protein moiety is a wild-type bacterial Era.

7. The method of claim 1 wherein the cell of said cell cycle is E. coli and said Era protein moiety is wild-type E. coli Era.

8. The method of claim 1 wherein said Era protein moiety is mutated human ERA.

9. The method of claim 1 wherein said Era protein moiety is a human mutated ERA sequence of a sequence of FIG. 20.

10. The method of claim 1 wherein said Era protein moiety is a human ERA sequence encoded by an ERA sequence of FIG. 19.

11. A method of screening for an agent that delays a bacterial cell cycle comprising:
   (a) providing purified wild-type bacterial Era;
   (b) preparing at least one agent suspected of inhibiting Era;
   (c) combining said purified Era and said agent with GTP to form an Era-agent-GTP combination;
   (d) measuring GDP resulting from said Era-agent-GTP combination; and
   (e) comparing GDP of step (d) with GDP resulting from a control, wherein GDP resulting from step (d) is reduced compared to GDP resulting from said control thereby identifying an agent that delays a bacterial cell cycle.

12. The method of claim 11 wherein said bacterial cell is E. coli.

13. A method of screening for an agent that delays a cell cycle of a cell foreign to a host organism comprising:
   (a) providing purified mutated Era protein moiety of a foreign cell;
   (b) preparing at least one agent suspected of inhibiting said Era protein moiety;
   (c) combining said purified Era protein moiety and said agent with GTP to form an Era protein moiety-agent-GTP combination;
   (d) measuring GDP resulting from said Era protein moiety-agent-GTP combination; and
   (e) comparing GDP of step (d) with GDP resulting from a control, wherein GDP resulting from step (d) is reduced compared to GDP resulting from said control thereby identifying an agent that delays a foreign cell cycle.

14. The method of claim 13 wherein said Era protein moiety is a human ERA sequence of a sequence of FIG. 20.

15. The method of claim 13 wherein said Era protein moiety is a human ERA sequence encoded by an ERA sequence of FIG. 19.

16. A method of screening for an agent that delays a cell cycle comprising:
   (a) preparing a cell having a heterologous era gene moiety nucleic acid sequence;
   (b) preparing a cell having a wild-type era gene moiety nucleic acid sequence;
   (c) exposing said cells of step (a) and step (b) for an effective time to an agent suspected of delaying a cell cycle; and
   (d) observing the growth of the cell of step (a) with the growth of the cell of step (b) whereby slow growth of the cell of step (a) and normal growth of the cell of step (b) result in identification of an agent that delays a cell cycle.

17. The method of claim 16 wherein said step of exposing said cells to said agent comprises growing said cells on a medium comprising an effective amount of said agent.

18. The method of claim 16 wherein said heterologous era gene moiety is selected from the group consisting of Francisella, Salmonella, Coxiella, Streptococcus, Bacillus, Haemophilus, Mycobacterium, Mycoplasm, Pseudomonas, and Synechocystis.

19. The method of claim 16 wherein said heterologous era gene moiety is located in the E. coli genome or on a plasmid.

20. The method of claim 16 wherein said heterologous era gene moiety is a human ERA.

21. The method of claim 16 wherein said heterologous era gene moiety is a human ERA sequence of FIG. 19.

22. A method of screening for an agent that delays a bacterial cell cycle comprising:

(a) preparing a cell having a heterologous era nucleic acid sequence;

(b) preparing a cell having a wild-type era nucleic acid sequence;

(c) exposing said cells of step (a) and step (b) for an effective time to an agent suspected of delaying a bacterial cell cycle; and (d) observing the growth of the bacterial cell of step (a) with the growth of the bacterial cell of step (b) whereby slow growth of the bacterial cell of step (a) and normal growth of the bacterial cell of step (b) result in identification of an agent that delays a bacterial cell cycle.

23. A method of screening for an agent that delays a cell cycle of a cell foreign to a host organism comprising:

(a) preparing a foreign cell having a heterologous era gene moiety nucleic acid sequence;

(b) preparing a cell having a wild-type era gene moiety nucleic acid sequence;

(c) exposing said cells of step (a) and step (b) for an effective time to an agent suspected of delaying a cell cycle; and (d) observing the growth of the cell of step (a) with the growth of the cell of step (b) whereby slow growth of the cell of step (a) and normal growth of the cell of step (b) result in identification of an agent that delays a foreign cell cycle.

24. The method of claim 23 wherein said heterologous era gene moiety is a human ERA.

25. The method of claim 23 wherein said heterologous era gene moiety is a human ERA sequence of FIG. 19.

* * * * *

SEQUENCE LISTING (1) GENERAL INFORMATION:

(iii) NUMBER OF SEQUENCES: 37

(2) INFORMATION FOR SEQ ID NO: 1:

(i) SEQUENCE CHARACTERISTICS:
       (A) LENGTH: 22
       (B) TYPE: nucleic acid
       (C) STRANDEDNESS: single
       (D) TOPOLOGY: linear (xi) SEQUENCE DESCRIPTION: SEQ ID NO: 1:

TTGGCGGCAT CCATTAATAG CC                                                22

(2) INFORMATION FOR SEQ ID NO: 2:

(i) SEQUENCE CHARACTERISTICS:
       (A) LENGTH: 22
       (B) TYPE: nucleic acid
       (C) STRANDEDNESS: single
       (D) TOPOLOGY: linear (xi) SEQUENCE DESCRIPTION: SEQ ID NO: 2:

GGCACTACGA TGAGTTAATG CC                                                22

(2) INFORMATION FOR SEQ ID NO: 3:

(i) SEQUENCE CHARACTERISTICS:
       (A) LENGTH: 22
       (B) TYPE: nucleic acid
       (C) STRANDEDNESS: single
       (D) TOPOLOGY: linear (xi) SEQUENCE DESCRIPTION: SEQ ID NO: 3:

AACCCCATCG TAATTAATCG GC                                                22

(2) INFORMATION FOR SEQ ID NO: 4:

(i) SEQUENCE CHARACTERISTICS:
       (A) LENGTH: 22
       (B) TYPE: nucleic acid
       (C) STRANDEDNESS: single
       (D) TOPOLOGY: linear (xi) SEQUENCE DESCRIPTION: SEQ ID NO: 4:

TTGAGGATTA ATTTCTCGAC GG                                                22

(2) INFORMATION FOR SEQ ID NO: 5:

(i) SEQUENCE CHARACTERISTICS:
       (A) LENGTH: 22
       (B) TYPE: nucleic acid
       (C) STRANDEDNESS: single
       (D) TOPOLOGY: linear (xi) SEQUENCE DESCRIPTION: SEQ ID NO: 5:

CGTCGTGAGT CAATTCTCGC CG                                                22

(2) INFORMATION FOR SEQ ID NO: 6:

(i) SEQUENCE CHARACTERISTICS:
       (A) LENGTH: 22
       (B) TYPE: nucleic acid
       (C) STRANDEDNESS: single (D) TOPOLOGY: linear (xi) SEQUENCE DESCRIPTION: SEQ ID NO: 6:

CACTCAGGCC GACTGACCTG GC                                                    22

(2) INFORMATION FOR SEQ ID NO: 7:

(i) SEQUENCE CHARACTERISTICS:
            (A) LENGTH: 22
            (B) TYPE: nucleic acid
            (C) STRANDEDNESS: single
            (D) TOPOLOGY: linear (xi) SEQUENCE DESCRIPTION: SEQ ID NO: 7:

GGTCGTCCAT CTGCCGCTGC CG                                                    22

(2) INFORMATION FOR SEQ ID NO: 8:

(i) SEQUENCE CHARACTERISTICS:
            (A) LENGTH: 22
            (B) TYPE: nucleic acid
            (C) STRANDEDNESS: single
            (D) TOPOLOGY: linear (xi) SEQUENCE DESCRIPTION: SEQ ID NO: 8:

CGAGTTGTCT GCGCCTTGCG GG                                                    22

(2) INFORMATION FOR SEQ ID NO: 9:

(i) SEQUENCE CHARACTERISTICS:
            (A) LENGTH: 24
            (B) TYPE: nucleic acid
            (C) STRANDEDNESS: single
            (D) TOPOLOGY: linear (xi) SEQUENCE DESCRIPTION: SEQ ID NO: 9:

GGTGGTTGGC ACAGGTTCAA GCCG                                                  24

(2) INFORMATION FOR SEQ ID NO: 10:

(i) SEQUENCE CHARACTERISTICS:
            (A) LENGTH: 24
            (B) TYPE: nucleic acid
            (C) STRANDEDNESS: single
            (D) TOPOLOGY: linear (xi) SEQUENCE DESCRIPTION: SEQ ID NO: 10:

ACATCGCCAA TAGAGCTGCT CGCC                                                  24

(2) INFORMATION FOR SEQ ID NO: 11:

(i) SEQUENCE CHARACTERISTICS:
            (A) LENGTH: 24
            (B) TYPE: nucleic acid
            (C) STRANDEDNESS: single
            (D) TOPOLOGY: linear (xi) SEQUENCE DESCRIPTION: SEQ ID NO: 11:

CGATCTACGT CGATACACCG GGCC                                                  24

(2) INFORMATION FOR SEQ ID NO: 12:

(i) SEQUENCE CHARACTERISTICS:
            (A) LENGTH: 24
            (B) TYPE: nucleic acid
            (C) STRANDEDNESS: single
            (D) TOPOLOGY: linear (xi) SEQUENCE DESCRIPTION: SEQ ID NO: 12:

TAGATGCTTA CGCACGATTG CCGC                                              24

(2) INFORMATION FOR SEQ ID NO: 13:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO: 13:

GATGAACTTC CTCGATATCG TGCC                                              24

(2) INFORMATION FOR SEQ ID NO: 14:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO: 14:

ATGTCTTTAC GCGCTTCAAT CCCG                                              24

(2) INFORMATION FOR SEQ ID NO: 15:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO: 15:

TGATTCTCGT TGAGCGTGAA GGGC                                              24

(2) INFORMATION FOR SEQ ID NO: 16:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO: 16:

TTGGCAACCA GACGCACGCG CCCC                                              24

(2) INFORMATION FOR SEQ ID NO: 17:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 17:

Gly Arg Pro Asn Val Gly Lys Ser
                5

(2) INFORMATION FOR SEQ ID NO: 18:

(i) SEQUENCE CHARACTERISTICS:
        (A) LENGTH: 5
        (B) TYPE: amino acid
        (C) STRANDEDNESS: single
        (D) TOPOLOGY: linear (xi) SEQUENCE DESCRIPTION: SEQ ID NO: 18:

Asp Thr Pro Gly Leu
                  5

(2) INFORMATION FOR SEQ ID NO: 19:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 19:

Ile Ser Ile Thr Ser Arg
                  5

(2) INFORMATION FOR SEQ ID NO: 20:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 20:

Ile Xaa Ile Thr Ser Xaa Lys Xaa Gln Thr Thr Arg
                  5                  10

(2) INFORMATION FOR SEQ ID NO: 21:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 21:

Glu Xaa Pro His Ser Xaa Ala Xaa Val
                  5

(2) INFORMATION FOR SEQ ID NO: 22:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 22:

Ser Gln Lys Gly Ile Val Ile Gly Lys Lys Gly
                  5                  10

(2) INFORMATION FOR SEQ ID NO: 23:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 23:

Leu Trp Val Lys Val Lys
                  5

(2) INFORMATION FOR SEQ ID NO: 24:

(i) SEQUENCE CHARACTERISTICS:
    (A) LENGTH: 16
    (B) TYPE: amino acid
    (C) STRANDEDNESS: single
    (D) TOPOLOGY: linear (xi) SEQUENCE DESCRIPTION: SEQ ID NO: 24:

```
Phe Ile Ala Ile Val Gly Arg Pro Asn Val Gly Lys Ser Thr
                 5                  10

Leu Leu
15
```

(2) INFORMATION FOR SEQ ID NO: 25:

(i) SEQUENCE CHARACTERISTICS:
        (A) LENGTH: 16
        (B) TYPE: amino acid
        (C) STRANDEDNESS: single
        (D) TOPOLOGY: linear (xi) SEQUENCE DESCRIPTION: SEQ ID NO: 25:

```
Lys Ile Val Val Val Gly Gly Gly Gly Val Gly Lys Ser Ala
                 5                  10

Leu Thr
15
```

(2) INFORMATION FOR SEQ ID NO: 26:

(i) SEQUENCE CHARACTERISTICS:
        (A) LENGTH: 346 amino acids
        (B) TYPE: amino acid
        (C) STRANDEDNESS:
        (D) TOPOLOGY: linear (xi) SEQUENCE DESCRIPTION: SEQ ID NO:26:

```
Xaa Xaa Xaa Xaa Xaa Xaa Xaa Xaa Xaa Xaa Xaa Xaa Xaa Xaa Xaa
1               5                   10                  15

Met Lys Lys Xaa Xaa Cys Xaa Tyr Ile Ser Xaa Ile Xaa Xaa Xaa Xaa
            20              25              30

Xaa Xaa Xaa Xaa Xaa Xaa Xaa Asn Ile Leu Lys Tyr Xaa Val Ser
        35                  40                  45

Xaa Xaa Xaa Arg Xaa Pro Xaa Xaa Xaa His Gln Xaa Xaa Thr Gly
    50                  55                  60

Ile Lys Xaa Leu Xaa Asp Thr Xaa Phe Xaa Tyr Xaa Xaa Xaa Xaa
65              70                  75                  80

Ile Xaa Ile Lys Glu Pro Lys Ala Ile Asn Lys Phe Xaa Xaa Xaa Ala
        85                  90                  95

Xaa Thr Thr Met Phe Lys Asp Xaa Xaa Val Xaa Leu Xaa Xaa Xaa Xaa
        100                 105                 110

Xaa Xaa Xaa Glu Met Gly Lys Trp Thr Glu Leu Glu Asp Asn Ile Val
        115                 120                 125

Glu Xaa Xaa Lys Xaa Lys His Ser Glu Xaa Xaa Ile Xaa Ile Phe Xaa
    130                 135                 140

Val Val Xaa Xaa Val Xaa Xaa Xaa Lys Lys Ser Leu Glu Ala Ala Met
145                 150                 155                 160

Phe Xaa Glu Tyr Ile Lys Glu Lys Leu Xaa Ser Xaa Tyr Asp Val Xaa
        165                 170                 175

Xaa Xaa Xaa Xaa Xaa Xaa Xaa Ile Tyr Val Xaa Xaa Lys Xaa Xaa Xaa
        180                 185                 190

Xaa Gln Xaa His Xaa Ile Asn Glu Xaa Glu Ser Arg Ile Glu Lys Leu
    195                 200                 205
```

```
Xaa Xaa Xaa Ser Glu Tyr Phe Phe Tyr Glu Asp Gln Ile Xaa Xaa
        210                 215                 220

Arg Ser Ile Lys Xaa Met Val Ala Xaa Ile Xaa Xaa Xaa Xaa Ile Met
225                 230                 235                 240

Arg Thr Ile Gly Ser Xaa Val Xaa Tyr Gln Ile Xaa Xaa Xaa Val Glu
                245                 250                 255

Xaa Asp Ser Tyr Lys Val Asp Gln Glu Lys Asn Ile Xaa Xaa Val Tyr
                260                 265                 270

Xaa Tyr Xaa Ser Xaa Leu Xaa Xaa Xaa Asn Xaa Xaa Xaa Xaa Xaa Xaa
            275                 280                 285

Xaa Xaa Ala Xaa Xaa Ala Lys Xaa Xaa Lys Xaa Xaa Thr Asp Ser Xaa
        290                 295                 300

Ile Xaa Xaa Xaa Arg Xaa Xaa Xaa Val Xaa Met Gln Xaa Asn Xaa Lys
305                 310                 315                 320

Thr His Xaa Xaa Xaa Xaa Ser Gly Xaa Ser Xaa Asp Asp Arg Ala Xaa
                325                 330                 335

Lys Ser Xaa Xaa Xaa Asp Leu Ile Xaa Xaa
                340                 345

(2) INFORMATION FOR SEQ ID NO:27:

(i) SEQUENCE CHARACTERISTICS:
        (A) LENGTH: 346 amino acids
        (B) TYPE: amino acid
        (C) STRANDEDNESS:
        (D) TOPOLOGY: linear (xi) SEQUENCE DESCRIPTION: SEQ ID NO:27:

Xaa Xaa Xaa Xaa Xaa Xaa Xaa Xaa Xaa Xaa Xaa Xaa Xaa Xaa Xaa Met
1               5                   10                  15

Lys Pro Thr Tyr Cys Xaa Tyr Ala Xaa Xaa Ile Xaa Xaa Xaa Xaa Xaa
                20                  25                  30

Xaa Xaa Xaa Xaa Xaa Xaa Xaa Gln Xaa Leu Glu Xaa Xaa Xaa Ser Xaa
            35                  40                  45

Xaa Xaa Arg Xaa Pro Xaa Xaa Xaa Xaa Tyr Gln Xaa Leu Xaa Gly Val
        50                  55                  60

Lys Xaa Phe Lys Asp Ile Xaa Val Xaa Tyr Xaa Xaa Xaa Xaa Xaa Xaa
65                  70                  75                  80

Leu Xaa Ala Gly Thr Glu Arg Thr Ile Asn Arg Tyr Xaa Xaa Arg Thr
                85                  90                  95

Xaa Arg Gly Ala Leu Arg Asp Xaa Xaa Ala Xaa Val Xaa Xaa Ile Xaa
            100                 105                 110

Xaa Glu Pro His Xaa Xaa Xaa Xaa Trp Glu Ser Gln Xaa Ala Trp Val Leu
        115                 120                 125

Asp Xaa Xaa Asn Xaa Lys Glu Ile Glu Xaa Xaa Thr Xaa Xaa Phe Xaa
        130                 135                 140

Val Ile Xaa Xaa Val Xaa Xaa Ile Lys Asn Arg Ala Glu Xaa Xaa Pro
145                 150                 155                 160

Leu Xaa Glu Lys Xaa Val Ser Ser Leu Tyr Ala Xaa Gln Lys Ile Xaa
            165                 170                 175

Xaa Xaa Xaa Xaa Xaa Thr Xaa Xaa Xaa Leu Xaa Xaa Lys Thr Xaa Xaa
            180                 185                 190

Xaa Xaa Xaa Asp Gln Xaa Gly Thr Xaa Glu Gln Ala Val His Gln Leu
            195                 200                 205

Met Xaa Xaa Ser Pro Xaa Phe Tyr Phe Xaa Pro Glu Gln Val Xaa Xaa
```

-continued

```
        210                 215                 220
Arg Ser Asp Gln Xaa Met Ala Xaa Xaa Ile Xaa Xaa Xaa Xaa Leu Met
225                 230                 235                 240

Arg Leu Leu Gly Gln Xaa Ile Xaa Tyr Xaa Leu Xaa Xaa Xaa Val Thr
                    245                 250                 255

Leu Ile Glu Phe Arg Xaa Xaa Lys Glu Xaa Lys Ile Xaa Xaa Ile Arg
                260                 265                 270

Xaa Ser Xaa Val Xaa Trp Xaa Xaa Lys Lys Xaa Xaa Xaa Xaa Xaa Xaa
            275                 280                 285

Xaa Xaa Xaa Gly Xaa Glu Arg Xaa Xaa Arg Val Xaa Thr Asn Xaa Xaa
        290                 295                 300

Leu Xaa Met Xaa Lys Trp Xaa Xaa Phe Xaa Lys Arg Xaa Phe Xaa Gln
305                 310                 315                 320

Xaa Xaa Xaa Xaa Xaa Xaa Ser Gly Xaa Ala Xaa Asn Glu Arg Leu Xaa
                325                 330                 335

Arg Glu Xaa Xaa Phe Glu Glu Xaa Xaa Xaa
                340                 345
```

(2) INFORMATION FOR SEQ ID NO:28:

(i) SEQUENCE CHARACTERISTICS:
        (A) LENGTH: 345 amino acids
        (B) TYPE: amino acid
        (C) STRANDEDNESS:
        (D) TOPOLOGY: linear (xi) SEQUENCE DESCRIPTION: SEQ ID NO:28:

```
Xaa Xaa Xaa Xaa Xaa Xaa Xaa Xaa Xaa Xaa Xaa Xaa Xaa Met Thr Asn
1               5                   10                  15

Glu Ser Phe Lys Ser Xaa Xaa Xaa Ser Xaa Ile Xaa Xaa Xaa Xaa Xaa
                20                  25                  30

Xaa Xaa Xaa Xaa Phe Xaa Xaa Arg Val Ile Xaa Xaa Xaa Xaa Ala Xaa
            35                  40                  45

Met Xaa Asp Xaa Pro Xaa Xaa Xaa Xaa Asn Lys Val Xaa Gln Gly Val
        50                  55                  60

Leu Xaa Thr Xaa Thr Ser Xaa Thr Xaa Phe Ile Xaa Xaa Xaa Xaa Ile
65                  70                  75                  80

Xaa Lys Pro Lys His Lys Xaa Leu Gly Asp Phe Xaa Met Xaa Val Xaa
                85                  90                  95

Gln Asn Thr Leu Lys Glu Xaa Xaa Xaa Xaa Leu Xaa Met Ile Asn Ala
                100                 105                 110

Glu Xaa Xaa Glu Xaa Xaa Gly Tyr Gly Lys Gly Xaa Glu Phe Ile Ile
        115                 120                 125

Glu Xaa Xaa Lys Xaa Gln Thr Met Ser Xaa Xaa Thr Xaa Xaa Phe Xaa
        130                 135                 140

Ile Val Xaa Xaa Ile Xaa Xaa Ile Xaa His Pro Asp Gln Xaa Xaa Leu
145                 150                 155                 160

Leu Xaa Asp Glu Tyr Xaa Arg Lys Arg Tyr Pro Xaa Lys Xaa Ile Xaa
                165                 170                 175

Xaa Xaa Xaa Xaa Xaa Xaa Xaa Xaa Ile Xaa Xaa Xaa Xaa Xaa Xaa Xaa
                180                 185                 190

Leu Glu Xaa Asn Xaa Ile Glu Thr Xaa Leu Ala Gln Ile Glu Ala Tyr
        195                 200                 205

Xaa Xaa Xaa Xaa Pro Gln Phe Tyr Xaa Xaa Ser Asp Gln Val Xaa Xaa
            210                 215                 220
```

-continued

His Pro Glu Xaa Xaa Ile Ile Xaa Xaa Leu Xaa Xaa Xaa Xaa Val Leu
225                 230                 235                 240

His Leu Thr Arg Glu Xaa Ile Xaa Xaa Xaa Ile Xaa Xaa Xaa Ala Xaa
                245                 250                 255

Xaa Glu Xaa Xaa Ser Ile Lys Gly Gln Asp Asn Gly Ser Xaa Val His
            260                 265                 270

Val Ala Xaa Thr Xaa Val Xaa Xaa Asp Xaa Xaa Xaa Xaa Xaa
        275                 280                 285

Xaa Xaa Xaa Xaa Xaa Ser Leu Xaa Xaa Glu Val Xaa Lys Arg Xaa Xaa
        290                 295                 300

Ala Xaa Xaa Xaa Ala Xaa Xaa Xaa Leu Xaa Ser Arg Xaa Tyr Xaa Glu
305                 310                 315                 320

Xaa Xaa Xaa Xaa Gln Lys Asp Xaa Arg Asn Lys Met Ser Gln Xaa Arg
                325                 330                 335

Asp Phe Xaa Phe Lys Glu Asp Glu Tyr
            340                 345

(2) INFORMATION FOR SEQ ID NO:29:

(i) SEQUENCE CHARACTERISTICS:
       (A) LENGTH: 346 amino acids
       (B) TYPE: amino acid
       (C) STRANDEDNESS:
       (D) TOPOLOGY: linear (xi) SEQUENCE DESCRIPTION: SEQ ID NO:29:

Xaa Xaa Xaa Xaa Xaa Xaa Xaa Xaa Xaa Xaa Xaa Xaa Xaa Xaa Met Ser
1               5                   10                  15

Ile Asp Lys Ser Tyr Cys Xaa Xaa Ile Xaa Xaa Val Xaa Xaa Xaa Xaa
                20                  25                  30

Xaa Xaa Xaa Xaa Xaa Xaa Xaa Xaa Lys Xaa Leu Xaa Xaa Xaa Xaa Ser
            35                  40                  45

Xaa Xaa Xaa Arg Xaa Ala Xaa Xaa Xaa His Arg Xaa Val Xaa Gly
        50                  55                  60

Ile His Xaa Glu Xaa Ala Tyr Xaa Ala Tyr Xaa Xaa Xaa Xaa Xaa
65              70                  75                  80

Leu Xaa Met Glu Glu Lys Arg Ala Ile Asn Arg Leu Xaa Xaa Xaa Ala
                85                  90                  95

Xaa Ser Ser Ile Gly Asp Xaa Glu Xaa Val Ile Xaa Xaa Xaa Xaa
            100                 105                 110

Xaa Glu Xaa Xaa Gly Thr Arg Xaa Trp Thr Pro Asp Xaa Glu Met Val
        115                 120                 125

Leu Asn Xaa Xaa Lys Xaa Arg Xaa Xaa Glu Gly Lys Ala Xaa Xaa Ile
130                 135                 140

Xaa Ala Val Xaa Xaa Val Xaa Asn Val Gln Glu Lys Ala Asp Xaa Xaa
145                 150                 155                 160

Pro His Leu Gln Phe Leu Ala Ser Gln Met Xaa Asn Xaa Leu Asp Ile
                165                 170                 175

Xaa Xaa Xaa Xaa Xaa Xaa Xaa Xaa Xaa Ile Xaa Xaa Glu Xaa Xaa
            180                 185                 190

Xaa Xaa Thr Xaa Leu Xaa Xaa Asp Thr Ile Ala Ala Ile Val Arg Lys
        195                 200                 205

His Xaa Xaa Xaa Ala Thr His His Phe Xaa Xaa Glu Asp Tyr Ile Xaa
    210                 215                 220

Xaa Arg Ser Gln Xaa Xaa Met Ala Xaa Xaa Ile Xaa Xaa Xaa Xaa Leu
225                 230                 235                 240

-continued

```
Met Arg Phe Leu Gly Ala Xaa Leu Xaa Tyr Xaa Val Thr Xaa Xaa Glu
                245                 250                 255

Xaa Xaa Glu Xaa Xaa Arg Phe Val Ser Asn Xaa Arg Gly Gly Tyr Xaa
            260                 265                 270

Asp Xaa Asn Gly Leu Xaa Leu Xaa Xaa Glu Gly Xaa Xaa Lys Met
            275                 280                 285

Xaa Xaa Xaa Asn Xaa Xaa Ala Lys Ile Xaa Thr Xaa Xaa Ile Glu Xaa
    290                 295                 300

Xaa Lys Xaa Met Gln Glu Met Xaa Xaa Phe Glu Ala Pro Xaa His Xaa
305                 310                 315                 320

Glu Xaa Xaa Xaa Xaa Xaa Xaa Ser Gly Glu Ala Xaa Asp Glu Arg Ala
                325                 330                 335

Xaa Arg Ser Xaa Xaa Xaa Val Asp Asp Leu
    340                 345

(2) INFORMATION FOR SEQ ID NO:30:

(i) SEQUENCE CHARACTERISTICS:
        (A) LENGTH: 345 amino acids
        (B) TYPE: amino acid
        (C) STRANDEDNESS:
        (D) TOPOLOGY: linear (xi) SEQUENCE DESCRIPTION: SEQ ID NO:30:

Xaa Xaa Xaa Xaa Xaa Xaa Xaa Xaa Xaa Xaa Xaa Xaa Met Thr Glu Gln
1               5                   10                  15

Phe Asp Lys Thr Tyr Cys Xaa Xaa Ile Xaa Xaa Val Xaa Xaa Xaa Xaa
                20                  25                  30

Xaa Xaa Xaa Xaa Xaa Xaa Xaa Xaa Lys Ile Leu Xaa Xaa Xaa Xaa Ser
        35                  40                  45

Xaa Xaa Xaa Arg Xaa Ala Xaa Xaa Xaa His Arg Xaa Val Gly Ile
    50                  55                  60

Xaa Lys Xaa Glu Xaa Ala Tyr Xaa Glu Xaa Tyr Xaa Xaa Xaa Xaa
65                  70                  75                  80

Leu Xaa Ile Glu Glu Lys Arg Ala Ile Asn Arg Leu Xaa Xaa Arg Ala
            85                  90                  95

Xaa Ser Ser Ala Ile Gly Asp Xaa Xaa Xaa Xaa Ile Xaa Xaa Xaa Xaa
        100                 105                 110

Xaa Asp Xaa Xaa Gly Thr His Trp Asn Ala Asp Xaa Glu Met Val Leu
    115                 120                 125

Asn Xaa Xaa Lys Xaa Arg Asn Xaa Xaa Ala Lys Ala Xaa Xaa Val Xaa
    130                 135                 140

Ala Ile Xaa Xaa Val Xaa Asn Ile Lys Asn Lys Asp Xaa Xaa Pro
145                 150                 155                 160

Phe Xaa Thr Asp Leu Ser Ser Lys Phe Xaa Asn Xaa Ala His Xaa Xaa
                165                 170                 175

Xaa Xaa Xaa Xaa Ile Xaa Xaa Xaa Xaa Ile Xaa Xaa Gln Arg Xaa Xaa
            180                 185                 190

Xaa Xaa Xaa Asn Xaa Xaa His Glu Xaa Glu Lys Ile Val Arg Gln Ser
        195                 200                 205

Xaa Arg Xaa Xaa Val His His Phe Xaa Xaa Glu Asp Tyr Val Xaa Xaa
    210                 215                 220

Arg Ser Gln Xaa Xaa Met Ala Xaa Xaa Ile Xaa Xaa Xaa Xaa Leu Met
225                 230                 235                 240

Arg Phe Thr Gly Glu Xaa Leu Xaa Tyr Xaa Val Thr Xaa Xaa Glu Xaa
```

```
                    245                 250                 255
Xaa Glu Xaa Xaa Gln Phe Lys Asn Xaa Arg Gly Thr Tyr Xaa Glu Xaa
                260                 265                 270

Asn Gly Leu Xaa Leu Xaa Xaa Xaa Glu Gly Xaa Xaa Lys Met Xaa Xaa
            275                 280                 285

Xaa Ala Gly Xaa Gln Lys Ile Xaa Thr Xaa Xaa Met Glu Xaa Xaa Ala
        290                 295                 300

Xaa Met Xaa Arg Xaa Xaa Xaa Phe Asp Asn Lys Xaa His Xaa Glu Xaa
305                 310                 315                 320

Xaa Xaa Xaa Xaa Xaa Xaa Gly Xaa Ala Xaa Asp Glu Arg Ala Xaa Arg
                325                 330                 335

Ser Xaa Xaa Xaa Met Asp Glu Xaa Xaa
                340                 345

(2) INFORMATION FOR SEQ ID NO:31:

(i) SEQUENCE CHARACTERISTICS:
        (A) LENGTH: 346 amino acids
        (B) TYPE: amino acid
        (C) STRANDEDNESS:
        (D) TOPOLOGY: linear (xi) SEQUENCE DESCRIPTION: SEQ ID NO:31:

Xaa Xaa Xaa Xaa Xaa Xaa Xaa Xaa Xaa Xaa Xaa Xaa Xaa Xaa Val Asp
1               5                   10                  15

Met Ala Glu Phe Arg Ser Xaa Xaa Xaa Cys Leu Ile Xaa Xaa Xaa Xaa
                20                  25                  30

Thr Xaa Xaa Xaa Xaa Thr Xaa Ala Xaa Val Xaa Thr Xaa Val Ala
        35                  40                  45

Xaa Xaa Xaa Met Xaa Pro Xaa Xaa Xaa His Thr Xaa Arg Gly Ile
50                  55                  60

Val His Arg Glu Xaa Asn Phe Xaa Ile Val Leu Xaa Xaa Xaa Xaa Xaa
65                  70                  75                  80

Leu Xaa Xaa Arg Pro Arg Thr Leu Leu Gly Lys Arg Leu Xaa Asp Leu
            85                  90                  95

Val Arg Asp Thr Tyr Thr Glu Xaa Xaa Xaa Xaa Gly Leu Cys Ile Pro
                100                 105                 110

Ala Asp Xaa Xaa Glu Ala Thr Xaa Xaa Gly Pro Gly Xaa Arg Trp Ile
        115                 120                 125

Val Asn Xaa Xaa Gln Ile Arg Ser Val Ala Pro Lys Thr Ile Leu Val
        130                 135                 140

Val Ile Val Thr Xaa Ile Xaa Xaa Val Pro Xaa Lys Asp Arg Xaa Ser
145                 150                 155                 160

Ala Gln Leu Val Ala Val Ser Asp Leu Val Ala Asp Ser Ala Xaa Xaa
            165                 170                 175

Xaa Xaa Xaa Xaa Xaa Ile Xaa Xaa Xaa Xaa Val Xaa Xaa Xaa Xaa Xaa
            180                 185                 190

Xaa Val Thr Xaa Glu Gln Xaa Asp Val Xaa Ile Asp Val Leu Ala Ala
        195                 200                 205

Ala Xaa Pro Xaa Pro Ala Tyr Tyr Ser Ala Gly Glu Xaa Leu Xaa Xaa
        210                 215                 220

Glu Pro Glu Glu Leu Leu Met Ala Xaa Leu Xaa Xaa Xaa Xaa Ala Val
225                 230                 235                 240

Leu Glu Gly Val His Asp Xaa Leu Xaa Xaa Xaa Leu Xaa Val Xaa Xaa
                245                 250                 255
```

-continued

```
Ile Asp Glu Val Ser Pro Xaa Xaa Arg Ala Gly Arg Gly Asp Leu Ile
            260                 265                 270

Asp Val His Xaa Val Leu Tyr Xaa Xaa Xaa Pro Xaa Xaa Xaa Xaa Xaa
        275                 280                 285

Xaa Xaa Xaa Xaa Ser Xaa Ala Arg Xaa Arg Glu Val Xaa Ile Ala Xaa
        290                 295                 300

Xaa Arg Gln Xaa Xaa Lys Xaa Xaa Xaa Leu Xaa Thr Asn Ile Tyr Xaa
305                 310                 315                 320

Asp Xaa His Xaa Asn Xaa Ala Lys Asn Xaa Gln Arg Asn Pro Lys Gln
                325                 330                 335

Xaa Gly Arg Xaa Xaa Phe Xaa Xaa Xaa Xaa
            340                 345
```

(2) INFORMATION FOR SEQ ID NO:32:

(i) SEQUENCE CHARACTERISTICS:
        (A) LENGTH: 347 amino acids
        (B) TYPE: amino acid
        (C) STRANDEDNESS:
        (D) TOPOLOGY: linear (xi) SEQUENCE DESCRIPTION: SEQ ID NO:32:

```
Xaa Xaa Xaa Xaa Xaa Xaa Xaa Xaa Xaa Xaa Xaa Xaa Xaa Xaa Xaa Xaa
1               5                   10                  15

Xaa Met Ser Phe Lys Ser Xaa Xaa Xaa Xaa Xaa Leu Xaa Xaa Xaa Xaa
            20                  25                  30

Xaa Xaa Xaa Xaa Xaa Phe Xaa Xaa His Val Met Xaa Xaa Xaa Xaa Ala
        35                  40                  45

Xaa Met Xaa Asp Xaa Ala Xaa Xaa Xaa Asn Lys Xaa Met Gly Ile
    50                  55                  60

Tyr Thr Xaa Asp Lys Glu Xaa Xaa Ile Val Phe Ile Xaa Xaa Xaa Xaa
65                  70                  75                  80

Ile Xaa Xaa Lys Pro Lys Thr Ala Leu Gly Asp Phe Xaa Val Glu Ser
            85                  90                  95

Xaa Tyr Ser Thr Leu Arg Glu Xaa Xaa Thr Val Leu Xaa Met Xaa Pro
            100                 105                 110

Ala Asp Xaa Xaa Glu Xaa Xaa Lys Arg Gly Lys Gly Xaa Asn Met Ile
        115                 120                 125

Ile Glu Xaa Xaa Arg Xaa Lys Xaa Xaa Ala Ala Lys Val Xaa Xaa Ile
130                 135                 140

Xaa Val Ile Xaa Xaa Ile Xaa Xaa Val His Xaa Pro Asp Gln Xaa Xaa
145                 150                 155                 160

Glu Gln Xaa Asp Asp Phe Arg Asn Gln Met Xaa Asp Xaa Gln Xaa Xaa
            165                 170                 175

Xaa Xaa Xaa Xaa Xaa Ile Xaa Xaa Xaa Xaa Ile Xaa Xaa Xaa Xaa Xaa
            180                 185                 190

Xaa Leu Gln Xaa Asn Xaa Xaa Ser His Xaa Val Asp Leu Leu Val Asp
    195                 200                 205

His Xaa Glu Xaa Xaa Phe Gln Tyr Phe Pro Ala Asp Gln Xaa Ile Xaa
    210                 215                 220

Xaa His Pro Glu Xaa Xaa Leu Val Xaa Xaa Met Xaa Xaa Xaa Xaa Val
225                 230                 235                 240

Leu Leu Leu Thr Arg Glu Xaa Ile Xaa Xaa Xaa Val Xaa Val Xaa Xaa
            245                 250                 255

Ile Asp Xaa Xaa Ser Met Xaa Ala Arg Asp Xaa Glu Thr His Lys Ile
            260                 265                 270
```

```
His Xaa Arg Xaa Thr Xaa Met Xaa Xaa Asp Xaa Xaa Xaa Xaa
        275                 280                 285

Ile Xaa Xaa Xaa Xaa Xaa Ala Met Xaa Xaa Lys Xaa Xaa Gln Met Xaa
290                     295                 300

Xaa Arg Xaa Xaa Xaa Leu Met Xaa Xaa Leu Xaa Asp Lys Xaa Tyr Xaa
305                 310                 315                 320

Glu Thr Xaa Xaa Xaa Xaa Xaa Lys Asn Xaa Arg Xaa Lys Lys Leu Asp
                325                 330                 335

Xaa Ala Asp Phe Xaa Xaa Asn Lys Lys Glu Tyr
            340                 345

(2) INFORMATION FOR SEQ ID NO:33:

(i) SEQUENCE CHARACTERISTICS:
        (A) LENGTH: 347 amino acids
        (B) TYPE: amino acid
        (C) STRANDEDNESS:
        (D) TOPOLOGY: linear (xi) SEQUENCE DESCRIPTION: SEQ ID NO:33:

Met Asp Ile Pro Asn Thr Thr Ala Thr Ile Ala Thr Ile Pro Gln Ala
1               5                  10                  15

Pro Ala Gly Phe Arg Ser Xaa Xaa Xaa Xaa Xaa Val Xaa Xaa Xaa Xaa
            20                  25                  30

Xaa Xaa Xaa Xaa Xaa Xaa Met Xaa Gln Xaa Val Xaa Xaa Xaa Xaa Ala
        35                  40                  45

Xaa Xaa Xaa Pro Val Ala Xaa Xaa Xaa Asn Arg Leu Gln Gly Ile
50                  55                  60

Ile Thr Xaa Pro Ser Ser Xaa Xaa Ile Xaa Leu Leu Xaa Xaa Xaa Xaa
65                  70                  75                  80

Ile Xaa Xaa Lys Pro His His Glu Leu Gly Arg Val Leu Val Xaa Asn
            85                  90                  95

Xaa Ile Gln Ala Ile His Ser Xaa Xaa Xaa Val Val Xaa Leu Xaa Xaa
        100                 105                 110

Xaa Asp Ser Ser Ala Thr Leu Xaa Xaa Gly Arg Gly Xaa Arg Phe Val
    115                 120                 125

Val Asp Leu Xaa Xaa Xaa Gln Lys Thr Asp Gly Xaa Xaa Xaa Xaa Val
130                 135                 140

Val Gly Leu Xaa Xaa Gln Xaa Xaa Xaa Xaa Xaa Gln Gln Pro Pro
145                 150                 155                 160

Asp Gln Arg Glu Glu Leu Asn Ala Ser Tyr Glu Thr Leu Thr Xaa Asn
                165                 170                 175

His Gly Trp Pro Cys Phe Xaa Lys Xaa Xaa Phe Xaa Xaa Xaa Xaa Xaa
            180                 185                 190

Xaa Leu Thr Xaa Glu Gly Leu Ser Asn Phe Gln Ser Ala Leu Glu Ala
        195                 200                 205

Arg Xaa Asp Pro Xaa Pro Tyr Tyr Tyr Pro Xaa Asp Xaa Leu Val Xaa
    210                 215                 220

Xaa Gln Pro Glu Xaa Xaa Ile Met Ala Xaa Leu Xaa Xaa Xaa Gln Leu
225                 230                 235                 240

Leu Leu Leu Thr Arg Gln Xaa Val Xaa Xaa Val Xaa Ile Ala Xaa
                245                 250                 255

Xaa Xaa Ile Glu Lys Val Xaa Xaa Xaa Glu Xaa Thr Pro Glu Arg Thr
        260                 265                 270

Asn Val Phe Xaa Ala Xaa Thr Xaa Xaa Xaa Gly Xaa Xaa Xaa Xaa Xaa
```

-continued

```
                275                 280                 285
Ile Xaa Xaa Gln Xaa Xaa Ser Met Xaa Gln Ala Xaa Xaa Thr Ala Xaa
    290                 295                 300

Xaa Gln Gln Xaa Gln Lys Xaa Xaa Xaa Ile Ser Gly Asp Xaa Tyr Xaa
305                 310                 315                 320

Lys Xaa Phe Xaa Xaa Xaa Glu Pro Lys Xaa Arg Gln Ser Arg Gln Gln
                325                 330                 335

Xaa Leu Glu Phe Xaa Xaa Arg Val Glu Glu Xaa
            340                 345
```

(2) INFORMATION FOR SEQ ID NO:34:

(i) SEQUENCE CHARACTERISTICS:
        (A) LENGTH: 346 amino acids
        (B) TYPE: amino acid
        (C) STRANDEDNESS:
        (D) TOPOLOGY: linear (xi) SEQUENCE DESCRIPTION: SEQ ID NO:34:

```
Xaa Xaa Xaa Xaa Xaa Xaa Xaa Xaa Xaa Xaa Xaa Xaa Xaa Xaa Xaa Xaa
1               5                   10                  15

Met Lys Val Leu Lys Xaa Xaa Xaa Xaa Gly Val Leu Xaa Pro Thr Xaa
                20                  25                  30

Ala Xaa Xaa Xaa Xaa Ile Xaa Phe Xaa His Asn Asp Asp Ser Leu
            35                  40                  45

Met Val Xaa Ser Met Asn Asn Xaa Xaa Leu Leu Ser Xaa Ser Thr Glu
    50                  55                  60

Val Ile Asn Gln Ala Asn Lys Asn Ile Val Phe Ile Xaa Val Xaa Xaa
65                  70                  75                  80

Phe Thr Glu Lys Lys His Ser Asn Tyr Glu Xaa Leu Ile Thr Xaa Glu
                85                  90                  95

Ile Arg Lys Ala Leu Ser Gln Ile Xaa Val Leu Leu Xaa Xaa Xaa
                100                 105                 110

Xaa Arg Ser Asp Gln Asn Xaa Xaa Xaa Asn Lys Ile Glu Phe Leu Lys
            115                 120                 125

Thr Gln Leu Gln Gln Xaa Lys Arg Tyr Gln Asn Leu Thr Arg Ile Phe
130                 135                 140

Xaa Ile Asn Lys Phe His Gln Xaa Ser Leu Ser Glu Val Asn Lys Ala
145                 150                 155                 160

Ile Ile Leu Glu Glu Phe Lys Pro Gln Xaa Lys Thr Ile Xaa Xaa Ile
                165                 170                 175

Asn Xaa Xaa Xaa Xaa Xaa Xaa Xaa Xaa Leu Xaa Xaa Xaa Xaa Leu
            180                 185                 190

Phe Asp Lys Asn Leu Phe Trp Ser Ile Phe Lys Gln Val Glu Leu Arg
                195                 200                 205

Tyr Asn Xaa Xaa Xaa Ile Phe Arg Lys Asp Ile Asn Phe Ile Asp Ala
                210                 215                 220

Asn Asn Asp Asp Xaa Lys Ile Leu Xaa Gly Leu Xaa Xaa Gln Ile Ile
225                 230                 235                 240

Phe Tyr Cys Lys Asn Xaa Ile Xaa Xaa Xaa Ile Xaa Xaa Arg Ile Glu
                245                 250                 255

Xaa Ile Glu Lys Ser Phe Asn Lys Glu Lys Asn Leu Leu Lys Ile His
                260                 265                 270

Leu Xaa Xaa Val Xaa Ser Xaa Pro Lys Leu Xaa Xaa Xaa Lys Xaa Ile
                275                 280                 285
```

```
Xaa Xaa Xaa Asn Ala Glu Met Ile Xaa Ala Xaa Xaa Ile Ala Thr Xaa
    290                 295                 300

Lys Lys Leu Xaa Xaa Xaa Asn His Phe Asp Cys Asp Ile Phe Ile Asp
305                 310                 315                 320

Ile Phe Xaa Xaa Thr Glu Xaa Xaa Xaa Xaa Xaa Lys Gln Lys Xaa
                325                 330                 335

Pro Val Tyr Ser Phe Leu Ser Lys Xaa Xaa
            340                 345

(2) INFORMATION FOR SEQ ID NO:35:

(i) SEQUENCE CHARACTERISTICS:
        (A) LENGTH: 348 amino acids
        (B) TYPE: amino acid
        (C) STRANDEDNESS:
        (D) TOPOLOGY: linear (xi) SEQUENCE DESCRIPTION: SEQ ID NO:35:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Gly Phe Val Ala Ile Xaa Gly Arg Pro Asn
                20                  25                  30

Val Gly Lys Ser Thr Leu Leu Asn Xaa Leu Xaa Gly Gln Lys Ile Xaa
            35                  40                  45

Ile Thr Ser Xaa Lys Xaa Gln Thr Thr Arg Xaa Xaa Ile Xaa Xaa
50                  55                  60

Xaa Xaa Thr Xaa Gly Xaa Xaa Gln Xaa Ile Xaa Val Asp Thr Pro Gly
65                  70                  75                  80

Xaa His Xaa Xaa Xaa Xaa Xaa Xaa Xaa Xaa Xaa Met Asn Lys Xaa
            85                  90                  95

Ala Xaa Xaa Xaa Xaa Xaa Xaa Met Asn Lys Xaa Ala Xaa Xaa Xaa
            100                 105                 110

Xaa Xaa Val Asp Leu Ile Xaa Phe Val Val Xaa Xaa Xaa Xaa Xaa
            115                 120                 125

Xaa Xaa Xaa Xaa Xaa Xaa Xaa Asp Xaa Xaa Xaa Xaa Xaa Xaa Xaa
            130                 135                 140

Leu Xaa Xaa Xaa Xaa Xaa Lys Asp Xaa Xaa Xaa Xaa Xaa Xaa Leu Leu
145                 150                 155                 160

Xaa Xaa Ile Xaa Xaa Xaa Xaa Xaa Xaa Xaa Xaa Phe Xaa Glu Xaa
            165                 170                 175

Xaa Xaa Xaa Xaa Xaa Val Pro Xaa Xaa Xaa Ser Ser Ala Xaa Xaa
            180                 185                 190

Xaa Xaa Xaa Xaa Gly Xaa Asn Val Xaa Xaa Leu Xaa Xaa Xaa Xaa Xaa
            195                 200                 205

Xaa Xaa Leu Pro Glu Gly Xaa Xaa Xaa Xaa Pro Xaa Xaa Xaa Xaa
            210                 215                 220

Thr Asp Xaa Xaa Xaa Arg Phe Xaa Xaa Ser Glu Xaa Ile Arg Glu Lys
225                 230                 235                 240

Xaa Xaa Xaa Xaa Xaa Xaa Xaa Glu Xaa Pro His Ser Xaa Ala Xaa Val
                245                 250                 255

Xaa Xaa Ile Xaa Xaa Xaa Xaa Xaa Xaa Xaa Glu Xaa Xaa Xaa Xaa
            260                 265                 270

Xaa Xaa Ile Xaa Ala Xaa Ile Xaa Val Glu Arg Xaa Ser Gln Lys Gly
            275                 280                 285

Ile Val Ile Gly Lys Lys Gly Xaa Xaa Leu Lys Xaa Ile Gly Xaa Xaa
            290                 295                 300
```

```
Ala Arg Xaa Asp Ile Glu Xaa Leu Xaa Xaa Xaa Gly Xaa Xaa Val Xaa
305                 310                 315                 320

Leu Xaa Leu Trp Val Lys Val Lys Xaa Xaa Trp Xaa Asp Xaa Xaa Xaa
            325                 330                 335

Xaa Leu Xaa Xaa Leu Gly Tyr Xaa Xaa Xaa Xaa Xaa
        340                 345
```

(2) INFORMATION FOR SEQ ID NO: 36:

(i) SEQUENCE CHARACTERISTICS:
        (A) LENGTH: 1317
        (B) TYPE: nucleic acid
        (C) STRANDEDNESS: single
        (D) TOPOLOGY: linear (xi) SEQUENCE DESCRIPTION: SEQ ID NO: 36:

```
GAGGTGGCTG CCCCCAGCTG GCGCGGGGCT AGGCTTGTTC AATCGGCGTT AAGAGTCTGG      60

CAGGTGGGCC CTCATGTCGC GAGGGAGCGG GTGATCCCTT TTTCCTCACT CTTAGGCTTC     120

CAACGGAGGT GCGTGTCCTG CGTCGCGGGG TCCGCTTTCT CTGGTCCCCG CTTGGCCTCG     180

GCTTCTCGCA GTAATGGCCA GGGCTCTGCC CTGGACCACT TCCTCGGATT CTCTCAGCCC     240

GACAGTTCGG TGACTCCTTG CGTCCCCGCG GTGTCCATGA ACAGAGATGA GCAGGATGTC     300

CTCTTGGTCC ATCACCCTGA TATGCCTGAG AATTCCCGGG TCCTACGAGT GGTCCTCCTG     360

GGAGCCCCGA ATGCAGGGAA GTCAACACTC TCCAACCAGC TACTGGGCCG AAAGGTGTTC     420

CCTGTTTCCA GGAAGGTGCA TACTACTCGC TGCCAAGCTC TGGGGGTCAT CACAGAGAAG     480

GAGACCCAGG TGATTCTACT TGACACACCT GGCATTATCA GTCCTGGTAA ACAGAAGAGG     540

CATCACCTGG AGCTCTCTTT GTTGGAAGAT CCATGGAAGA GCATGGAATC TGCTGATCTT     600

GTTGTGGTTC TTGTGGATGT CTCAGACAAG TGGACACGGA ACCAGCTCAG CCCCCAGTTG     660

CTCAGGTGCT TGACCAAGTA CTCCCAGATC CCTAGTGTCC TGGTCATGAA CAAGGTAGAT     720

TGTTTGAAGC AGAAGTCAGT TCTCCTGGAG CTCACGGCAG CCCTCACTGA AGGTGTGGTC     780

AATGGCAAAA AGCTCAAGAT GAGGCAGGCC TTCCACTCAC ACCCTGGCAC CCATTGCCCC     840

AGCCCAGCAG TTAAGGACCC AAACACACAA TCTGTGGGAA ATCCTCAGAG GATTGGCTGG     900

CCCCACTTCA AGGAGATCTT CATGTTGTCA GCCCTAAGCC AGGAGGATGT GAAAACACTA     960

AAGCAATACC TTCTGACACA GGCCCAGCCA GGGCCCTGGG AGTACCACAG TGCAGTCCTC    1020

ACTAGCCAGA CACCAGAAGA GATCTGTGCC AACATTATCC GAGAGAAGCT CCTAGAACAC    1080

CTGCCCCAGG AGGTGCCTTA CAATGTACAG CAGAAGACAG CAGTGTGGGA GGAAGGACCA    1140

GGTGGGGAGC TGGTTATCCA ACAGAAGCTT CTGGTGCCCA AGAATCTTA TGTGAAACTC     1200

CTGATTGGTC CGAAGGGCCA CGTGATCTCC CAGATAGCAC AGGAGGCAGG CCATGACCTC    1260

ATGGACATCT TCCTCTGCGA TGTTGACATC CGCCTCTCTG TGAAGCTCCT CAAGTGA      1317
```

(2) INFORMATION FOR SEQ ID NO: 37:

(i) SEQUENCE CHARACTERISTICS:
        (A) LENGTH: 438
        (B) TYPE: amino acid
        (C) STRANDEDNESS: single
        (D) TOPOLOGY: linear (xi) SEQUENCE DESCRIPTION: SEQ ID NO: 37:

```
Glu Val Ala Ala Pro Ser Trp Arg Gly Ala Arg Leu Val Gln Ser Ala
1               5                   10                  15
```

-continued

```
Leu Arg Val Trp Gln Val Gly Pro His Val Ala Arg Glu Arg Val Ile
            20                  25                  30
Pro Phe Ser Ser Leu Leu Gly Phe Gln Arg Arg Cys Val Ser Cys Val
        35                  40                  45
Ala Gly Ser Ala Phe Ser Gly Pro Arg Leu Ala Ser Ala Ser Arg Ser
    50                  55                  60
Asn Gly Gln Gly Ser Ala Leu Asp His Phe Leu Gly Phe Ser Gln Pro
65                  70                  75                  80
Asp Ser Ser Val Thr Pro Cys Val Pro Ala Val Ser Met Asn Arg Asp
                85                  90                  95
Glu Gln Asp Val Leu Leu Val His His Pro Asp Met Pro Glu Asn Ser
            100                 105                 110
Arg Val Leu Arg Val Val Leu Gly Ala Pro Asn Ala Gly Lys Ser
        115                 120                 125
Thr Leu Ser Asn Gln Leu Leu Gly Arg Lys Val Phe Pro Val Ser Arg
    130                 135                 140
Lys Val His Thr Thr Arg Cys Gln Ala Leu Gly Val Ile Thr Glu Lys
145                 150                 155                 160
Glu Thr Gln Val Ile Leu Leu Asp Thr Pro Gly Ile Ile Ser Pro Gly
                165                 170                 175
Lys Gln Lys Arg His His Leu Glu Leu Ser Leu Leu Glu Asp Pro Trp
            180                 185                 190
Lys Ser Met Glu Ser Ala Asp Leu Val Val Val Leu Val Asp Val Ser
        195                 200                 205
Asp Lys Trp Thr Arg Asn Gln Leu Ser Pro Gln Leu Leu Arg Cys Leu
    210                 215                 220
Thr Lys Tyr Ser Gln Ile Pro Ser Val Leu Val Met Asn Lys Val Asp
225                 230                 235                 240
Cys Leu Lys Gln Lys Ser Val Leu Leu Glu Leu Thr Ala Ala Leu Thr
                245                 250                 255
Glu Gly Val Val Asn Gly Lys Lys Leu Lys Met Arg Gln Ala Phe His
            260                 265                 270
Ser His Pro Gly Thr His Cys Pro Ser Pro Ala Val Lys Asp Pro Asn
        275                 280                 285
Thr Gln Ser Val Gly Asn Pro Gln Arg Ile Gly Trp Pro His Phe Lys
    290                 295                 300
Glu Ile Phe Met Leu Ser Ala Leu Ser Gln Glu Asp Val Lys Thr Leu
305                 310                 315                 320
Lys Gln Tyr Leu Leu Thr Gln Ala Gln Pro Gly Pro Trp Glu Tyr His
                325                 330                 335
Ser Ala Val Leu Thr Ser Gln Thr Pro Glu Glu Ile Cys Ala Asn Ile
            340                 345                 350
Ile Arg Glu Lys Leu Leu Glu His Leu Pro Gln Glu Val Pro Tyr Asn
        355                 360                 365
Val Gln Gln Lys Thr Ala Val Trp Glu Glu Gly Pro Gly Gly Glu Leu
    370                 375                 380
Val Ile Gln Gln Lys Leu Leu Val Pro Lys Glu Ser Tyr Val Lys Leu
```

-continued

```
            385                 390                 395                 400

Leu Ile Gly Pro Lys Gly His Val Ile Ser Gln Ile Ala Gln Glu Ala
                405                 410                 415

Gly His Asp Leu Met Asp Ile Phe Leu Cys Asp Val Asp Ile Arg Leu
                420                 425                 430

Ser Val Lys Leu Leu Lys
            435
```